United States Patent [19]

Boden

[11] 4,440,961

[45] Apr. 3, 1984

[54] BRANCHED CHAIN OLEFINIC ALCOHOLS, THIOLS, ESTERS AND ETHERS, ORGANOLEPTIC USES THEREOF, PROCESSES FOR PREPARING SAME AND INTERMEDIATES THEREFOR

[75] Inventor: Richard M. Boden, Monmouth Beach, N.J.

[73] Assignee: International Flavors & Fragrances Inc., New York, N.Y.

[21] Appl. No.: 422,525

[22] Filed: Sep. 23, 1982

Related U.S. Application Data

[60] Division of Ser. No. 322,734, Nov. 19, 1981, Pat. No. 4,375,505, which is a continuation-in-part of Ser. No. 212,887, Dec. 4, 1980, Pat. No. 4,318,934.

[51] Int. Cl.³ .................. C07C 33/025; C07C 69/007; C07C 149/08; C07C 153/09
[52] U.S. Cl. .................. 568/840; 260/455 R; 560/261; 568/59; 568/69; 568/851; 568/687
[58] Field of Search .................. 568/840, 875, 851, 59, 568/69, 687; 560/261; 260/455 R

[56] References Cited

U.S. PATENT DOCUMENTS

| 2,801,266 | 7/1957 | Schinz | 568/840 |
| 3,821,318 | 6/1974 | Brendel et al. | 568/840 |
| 3,959,396 | 5/1976 | Ochsner et al. | 568/840 |
| 4,006,193 | 2/1977 | Ninagawa et al. | 568/840 |

FOREIGN PATENT DOCUMENTS

1414458 11/1975 United Kingdom ................ 568/687

OTHER PUBLICATIONS

Hayashi et al., "Tetrahydron Letters," No. 59, pp. 6241–6243, 1968.

Primary Examiner—J. E. Evans
Attorney, Agent, or Firm—Arthur L. Liberman

[57] ABSTRACT

Described are compounds defined according to the structure:

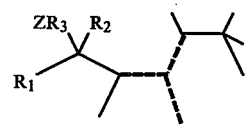

taken alone or in admixture wherein one of the dashed lines is a carbon-carbon double bond and each of the other of the dashed lines are carbon-carbon single bonds; wherein $R_1$ represents $C_1$–$C_4$ alkyl; $R_2$ represents $C_1$–$C_4$ alkyl; Z represents oxygen or sulfur; $R_3$ represents hydrogen, MgX, Li, $C_1$–$C_3$ lower alkyl or $C_1$–$C_3$ lower acyl; and wherein X represents chloro, bromo or iodo and uses thereof in augmenting or enhancing the aroma and/or taste of consumable materials such as perfume compositions, colognes, perfumed articles, e.g., solid or liquid anionic, cationic, nonionic or zwitterionic detergents, fabric softener compositions or dryer-added fabric softener articles, smoking tobaccos, chewing gums, chewing tobaccos, medicinal products or toothpastes. Also described are processes for preparing such compounds hereinafter described as branched chain olefinic alcohols, thiols, esters and ethers.

7 Claims, 48 Drawing Figures

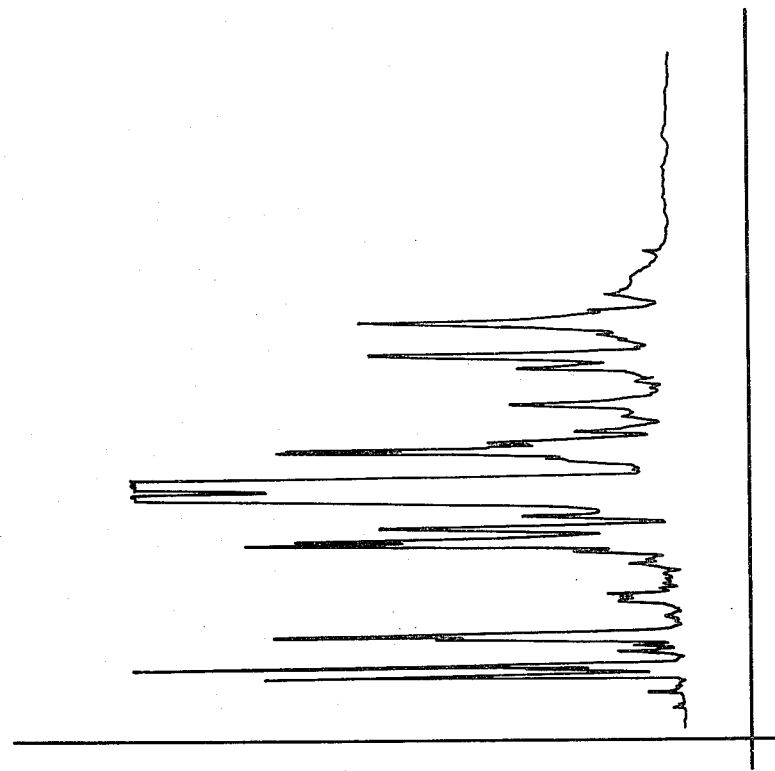
FIG.AC
GLC PROFILE FOR EXAMPLE A.
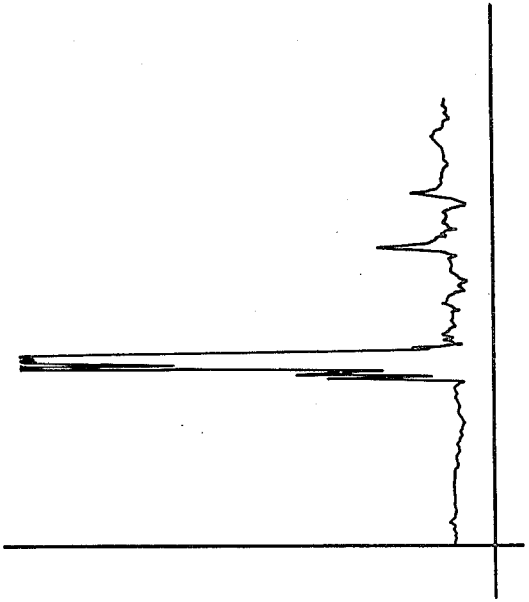
FIG.AA
GLC PROFILE FOR EXAMPLE A.
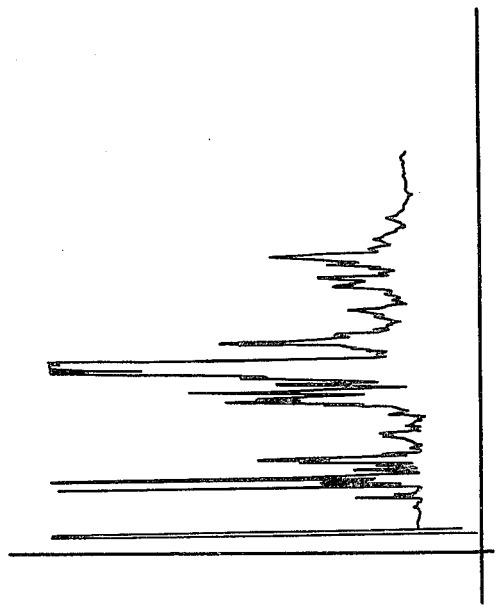
FIG.AB
GLC PROFILE FOR EXAMPLE A.

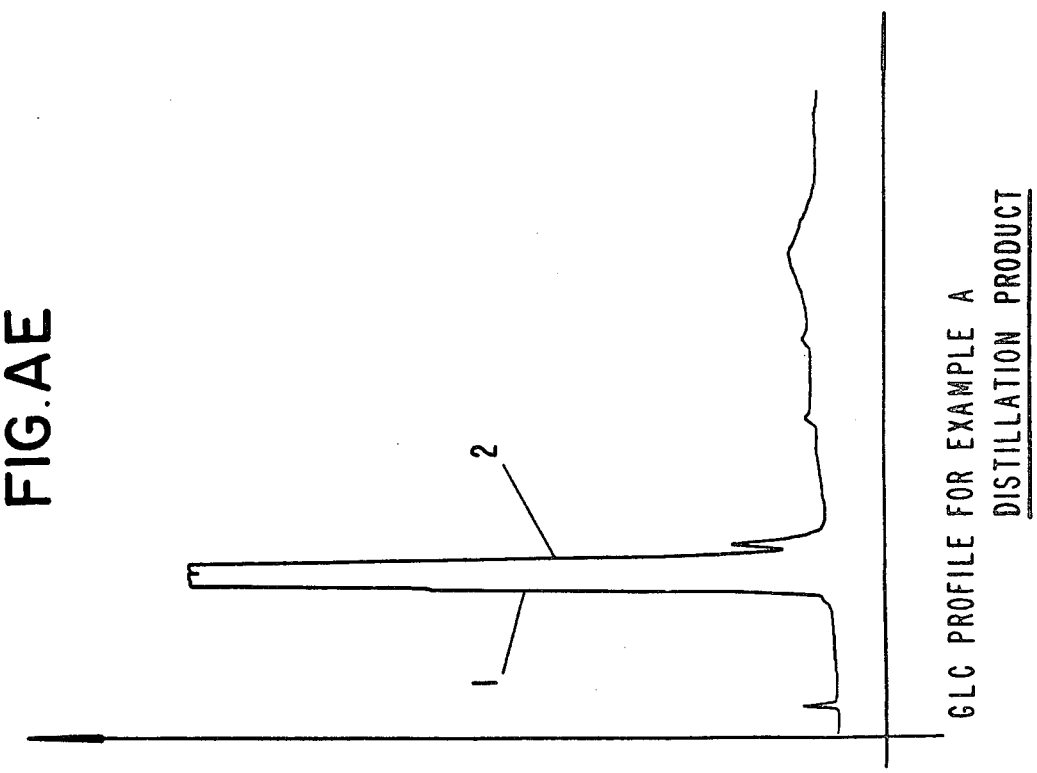
FIG.AE
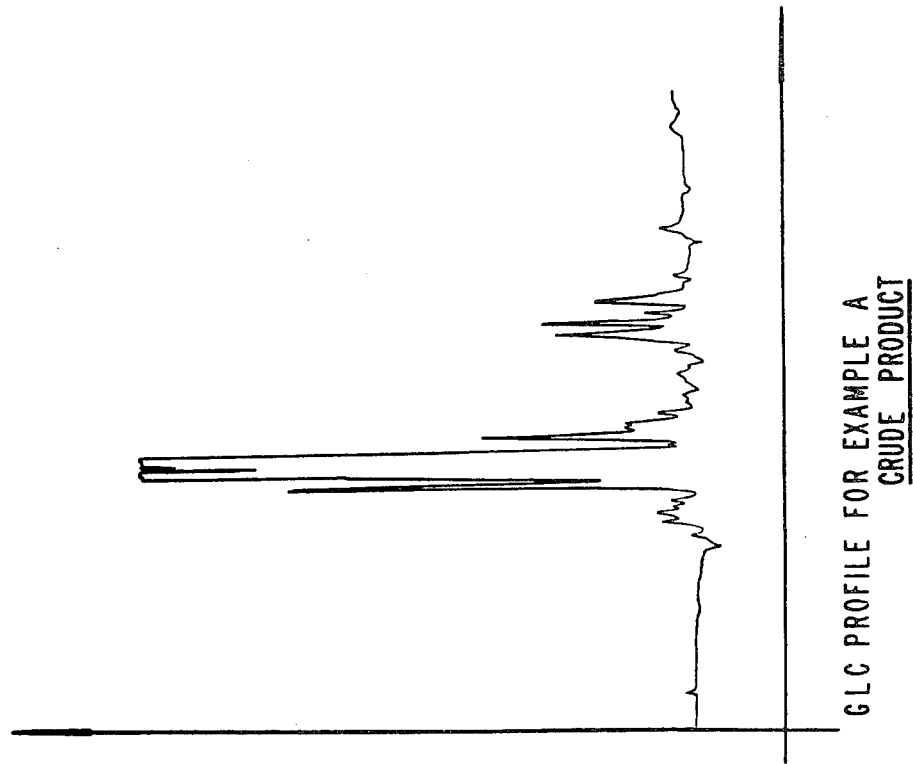
FIG.AD

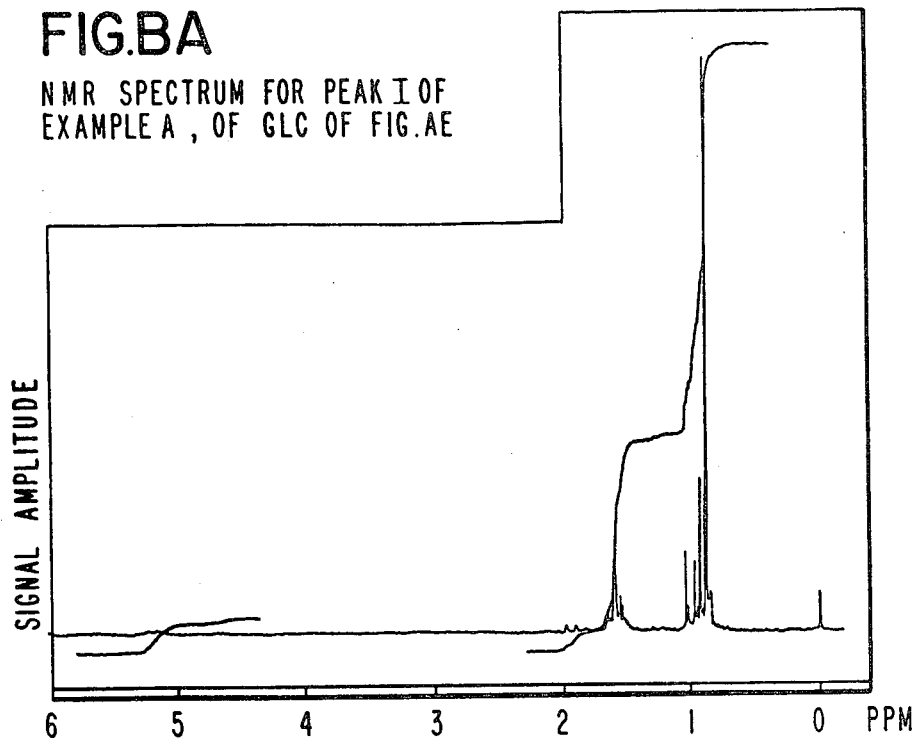
FIG.BA
NMR SPECTRUM FOR PEAK I OF EXAMPLE A, OF GLC OF FIG.AE
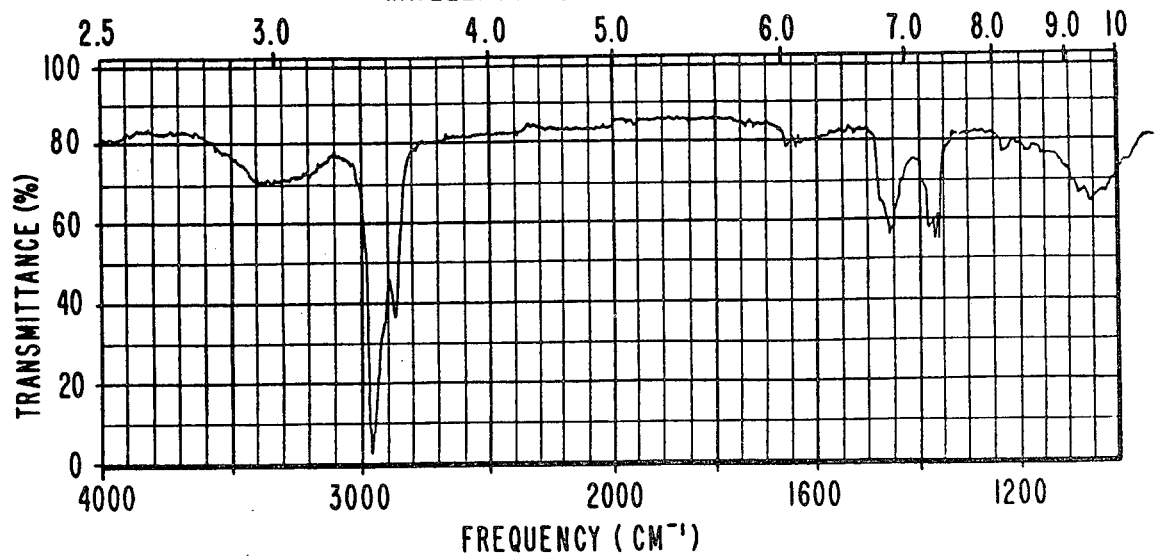
IR SPECTRUM FOR EXAMPLE A, PEAK I, OF GLC OF FIG.AE.
FIG.BB

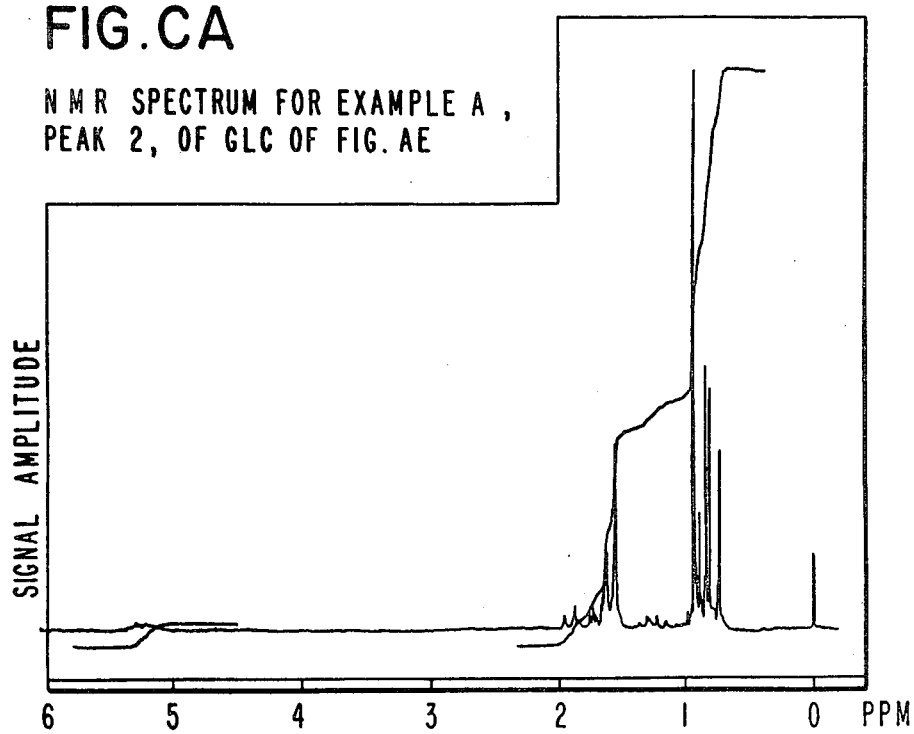
FIG.CA
NMR SPECTRUM FOR EXAMPLE A, PEAK 2, OF GLC OF FIG.AE
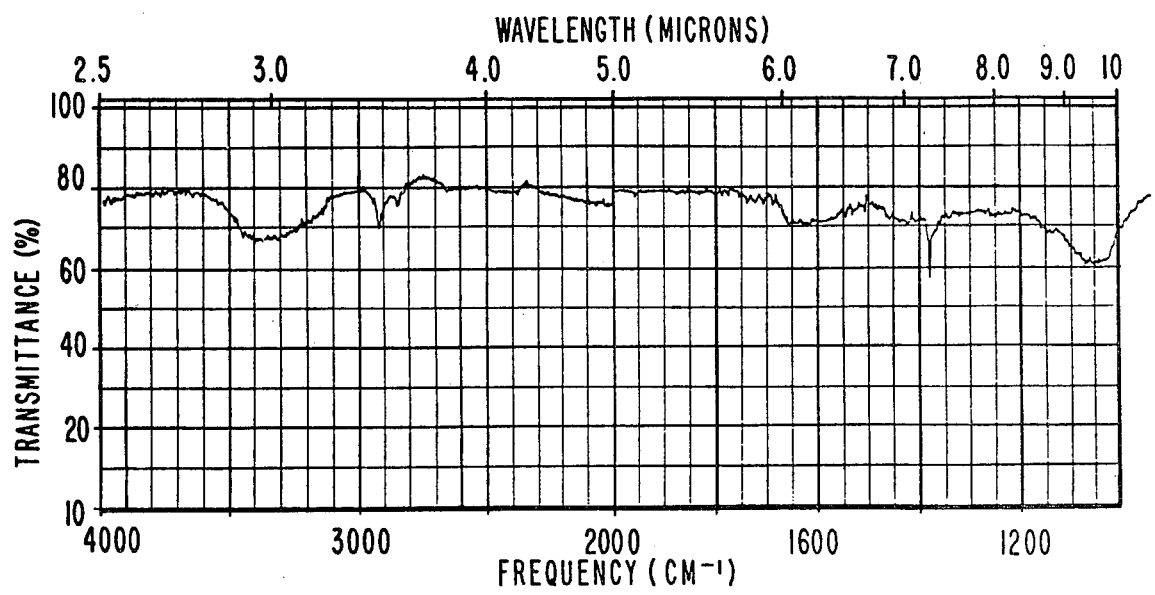
IR SPECTRUM FOR EXAMPLE I, PEAK 2 OF GLC OF FIG.AE
FIG.CB

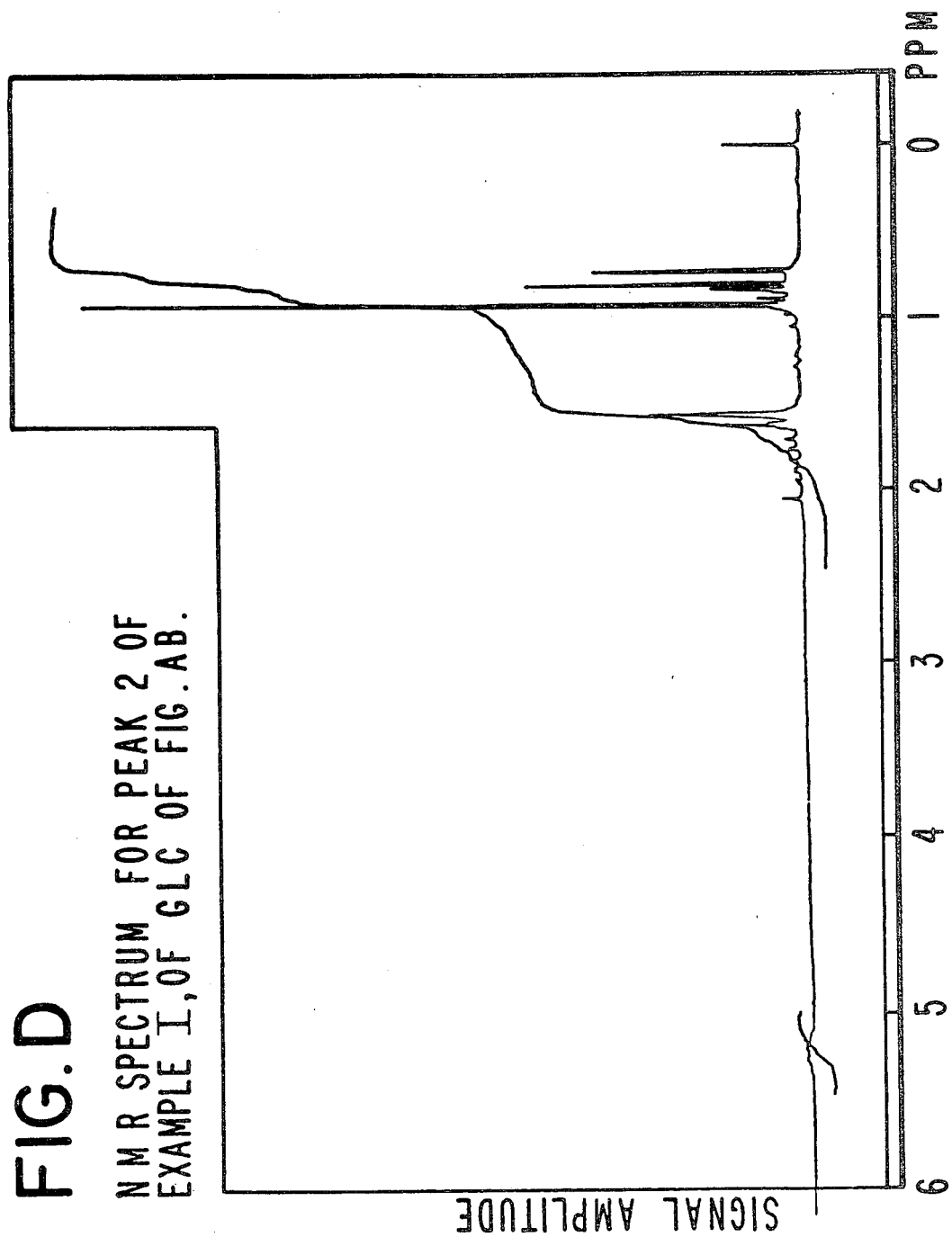
FIG. D
NMR SPECTRUM FOR PEAK 2 OF EXAMPLE I, OF GLC OF FIG. AB.

GLC PROFILE FOR EXAMPLE I.

IR SPECTRUM FOR PEAK 3 OF EXAMPLE I.

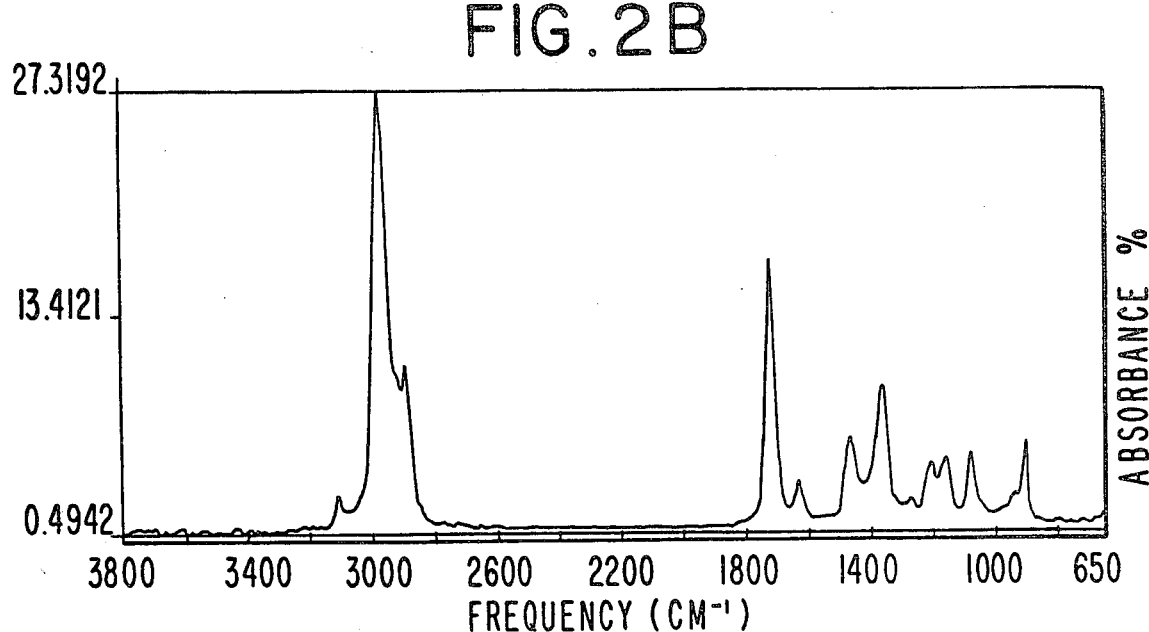
IR SPECTRUM FOR PEAK 4 OF EXAMPLE I.
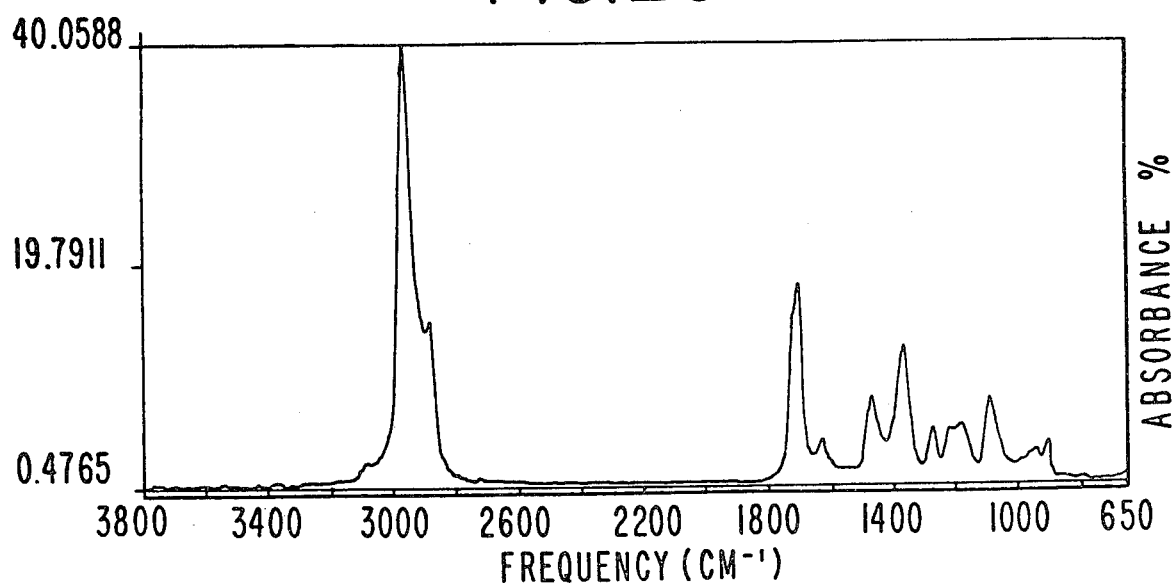
IR SPECTRUM FOR PEAK 5 OF EXAMPLE I.

IR SPECTRUM FOR PEAK 6 OF EXAMPLE I.

IR SPECTRUM FOR PEAK 7 OF EXAMPLE I.

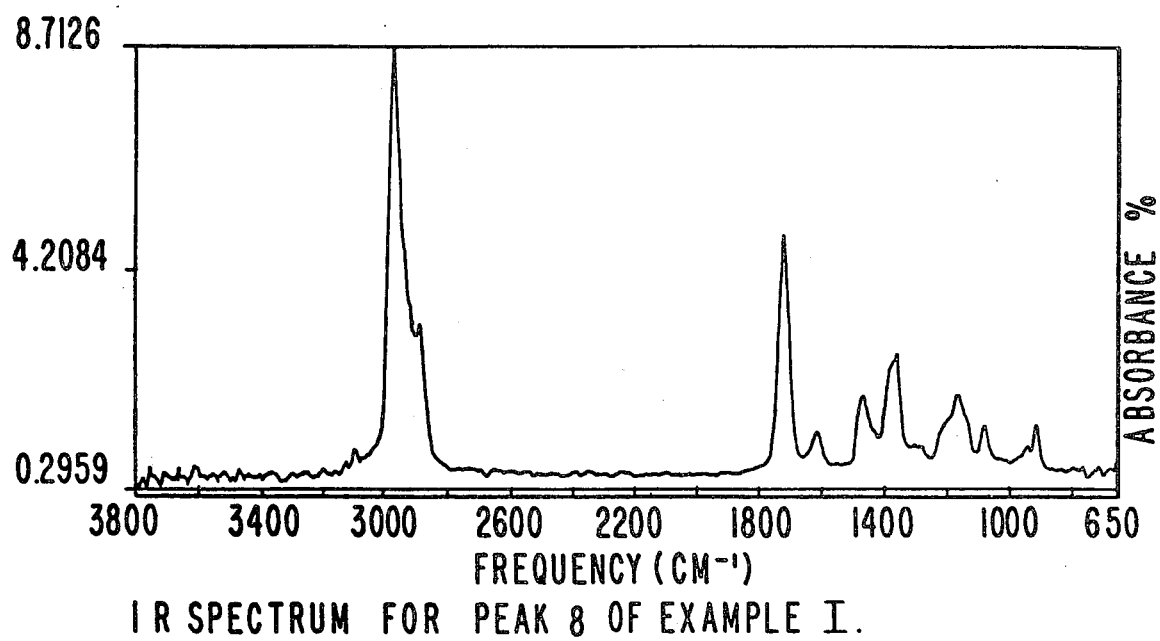
IR SPECTRUM FOR PEAK 8 OF EXAMPLE I.
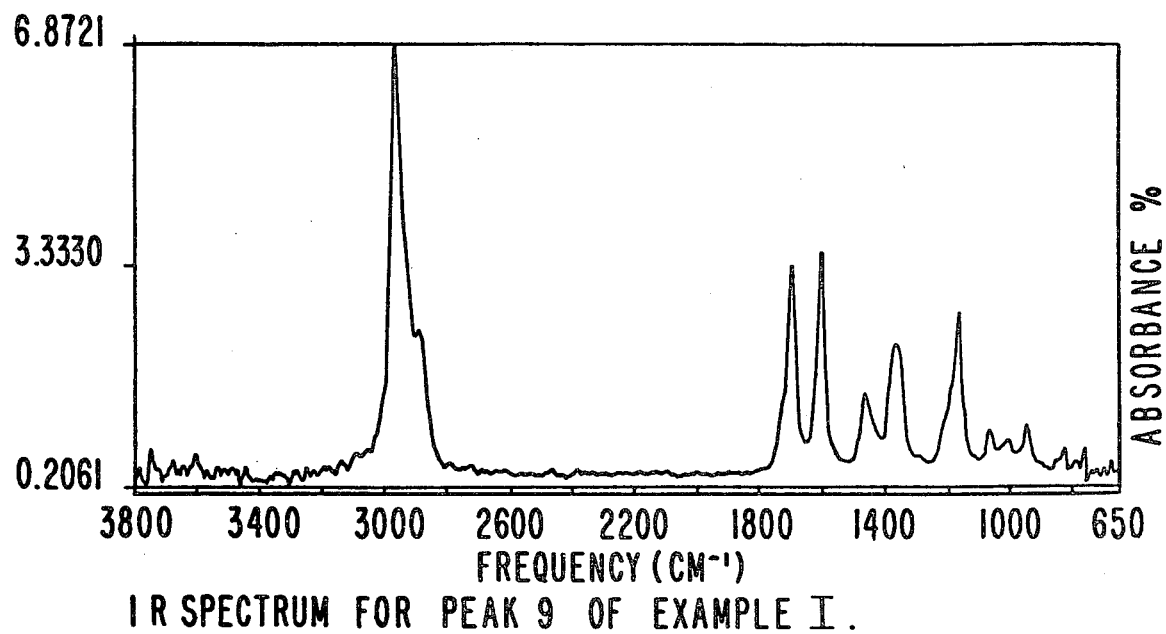
IR SPECTRUM FOR PEAK 9 OF EXAMPLE I.

IR SPECTRUM FOR PEAK 10 OF EXAMPLE I.

NMR SPECTRUM FOR EXAMPLE I.

NMR SPECTRUM FOR EXAMPLE I.

NMR SPECTRUM FOR EXAMPLE I

GLC PROFILE FOR EXAMPLE II.

IR SPECTRUM FOR EXAMPLE II.

MASS SPECTRUM FOR EXAMPLE II.

GLC PROFILE FOR EXAMPLE III.

MASS SPECTRUM FOR EXAMPLE III.

GLC PROFILE FOR EXAMPLE IV.

FIG. 7
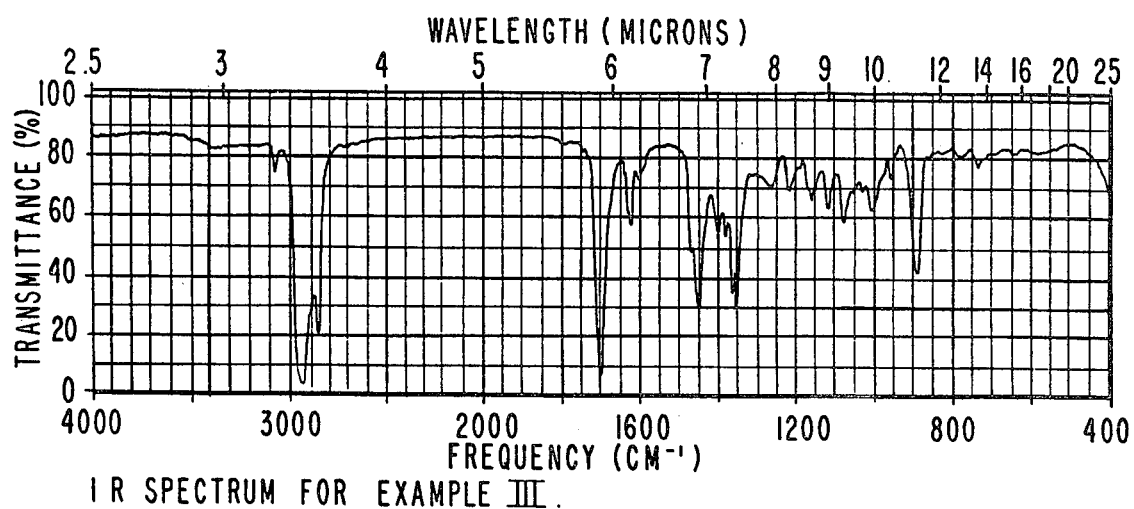
IR SPECTRUM FOR EXAMPLE III.
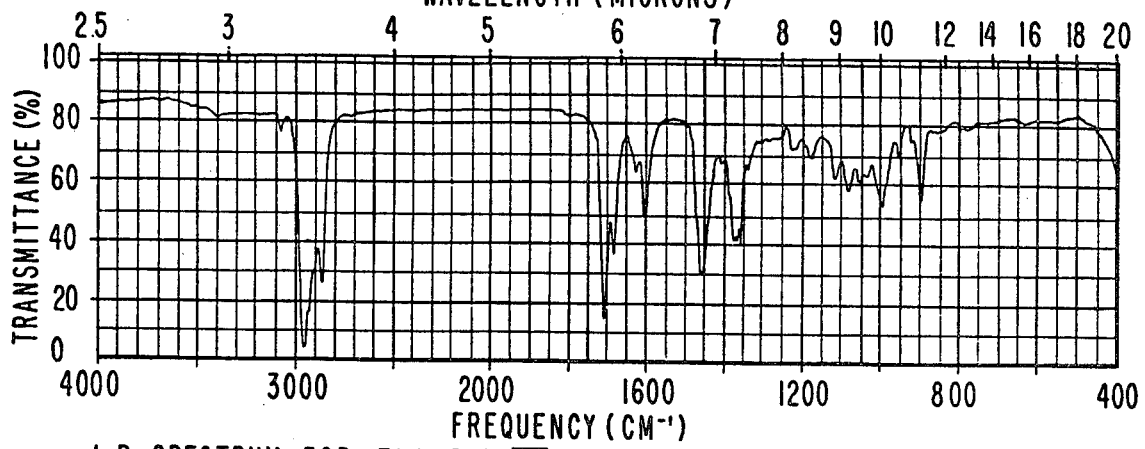
IR SPECTRUM FOR EXAMPLE IV.
FIG. 10

FIG.11
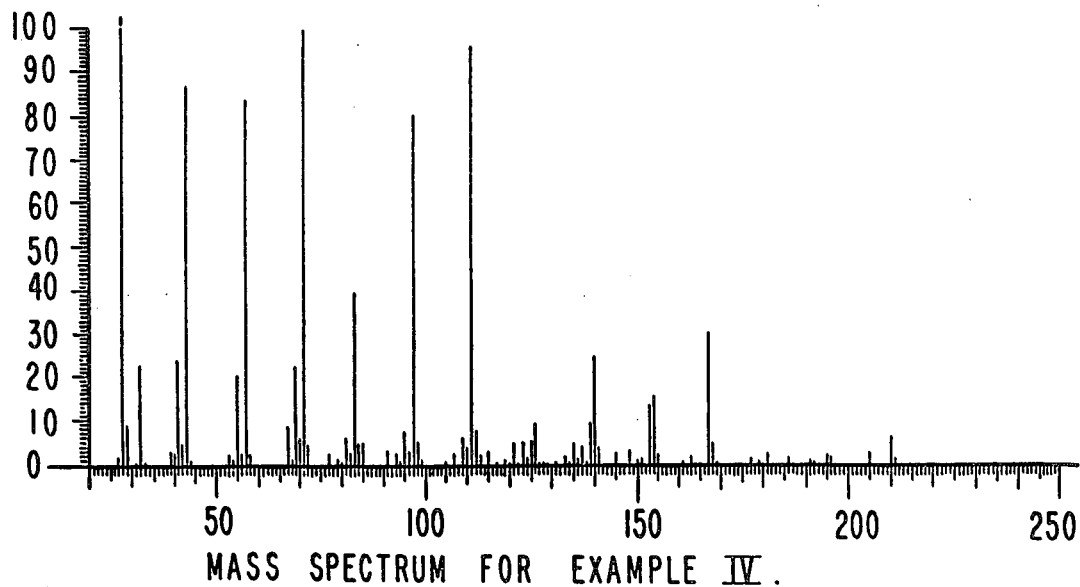
MASS SPECTRUM FOR EXAMPLE IV.
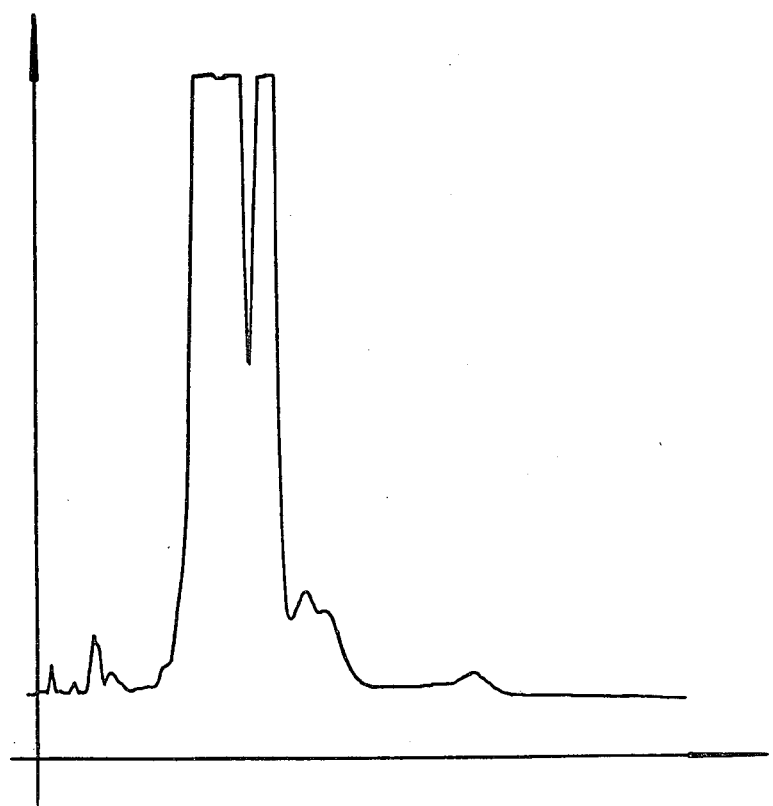
GLC PROFILE FOR EXAMPLE VA.
FIG.12

GLC PROFILE FOR EXAMPLE VB

GLC PROFILE FOR EXAMPLE VIIA.

GLC PROFILE FOR EXAMPLE IX.

IR SPECTRUM FOR EXAMPLE IX.

NMR SPECTRUM FOR EXAMPLE IX.

GLC PROFILE FOR EXAMPLE X.
CRUDE PRODUCT

GLC PROFILE FOR FRACTION 4, OF EXAMPLE X.

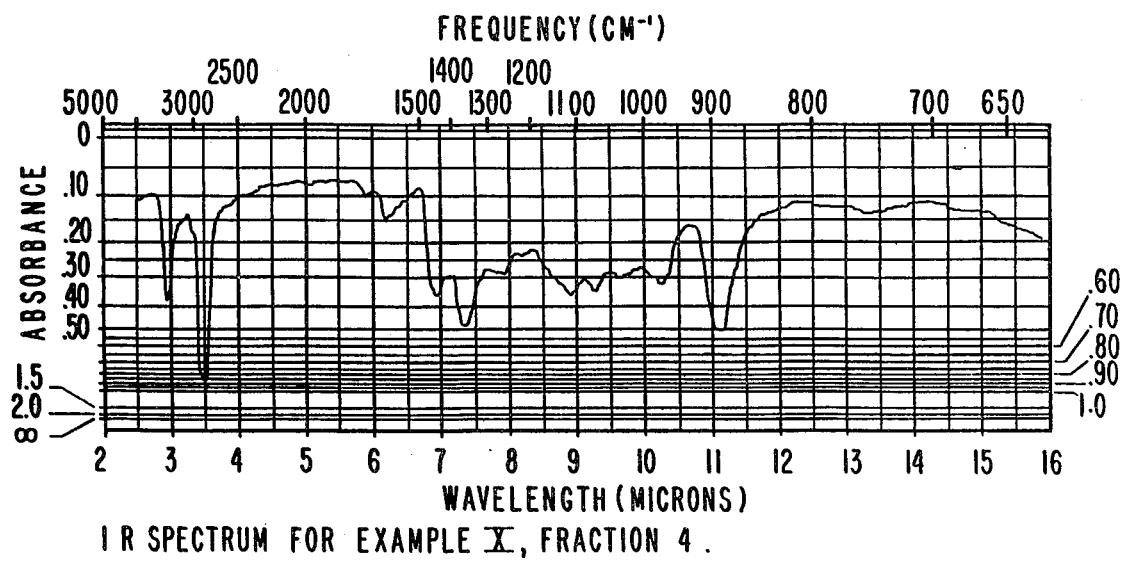

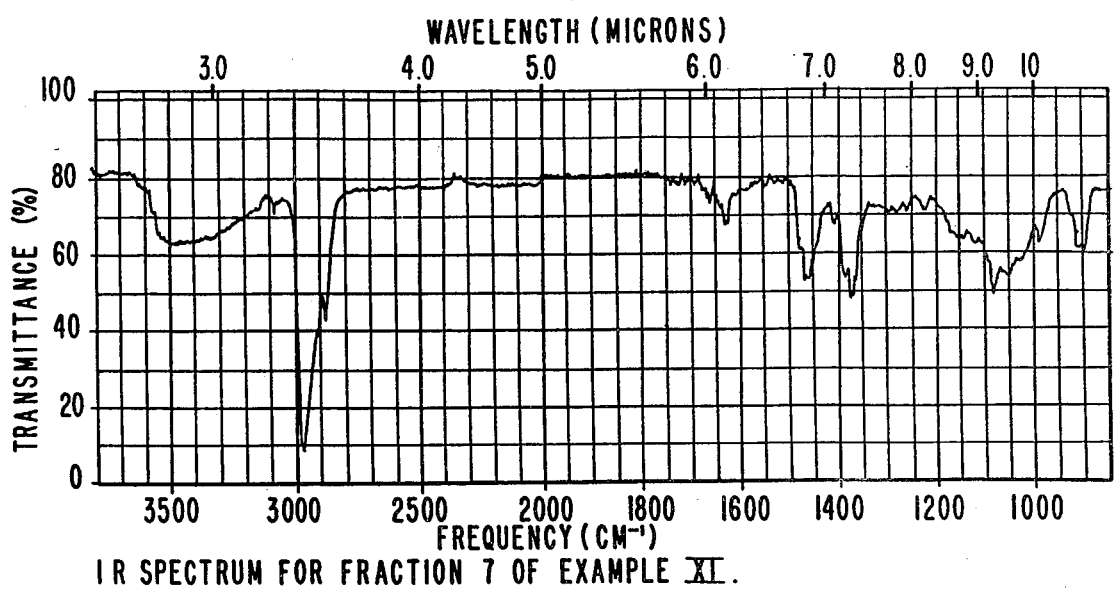
FIG.23 IR SPECTRUM FOR FRACTION 7 OF EXAMPLE XI.
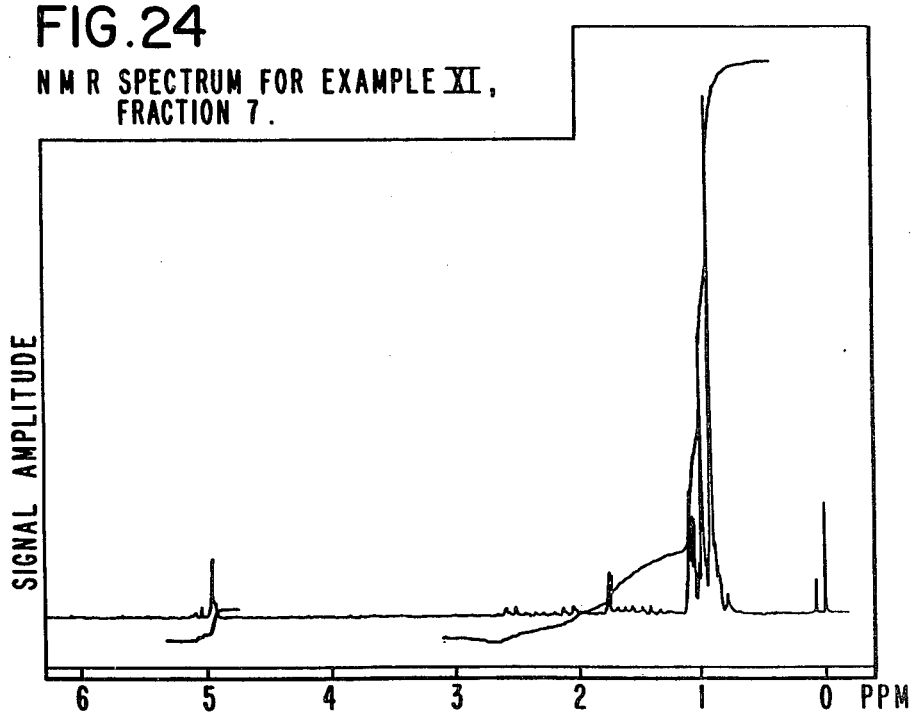
FIG.24 NMR SPECTRUM FOR EXAMPLE XI, FRACTION 7.

GLC PROFILE FOR FRACTION 8 EXAMPLE XII.

GLC PROFILE FOR EXAMPLE XII.
CRUDE PRODUCT

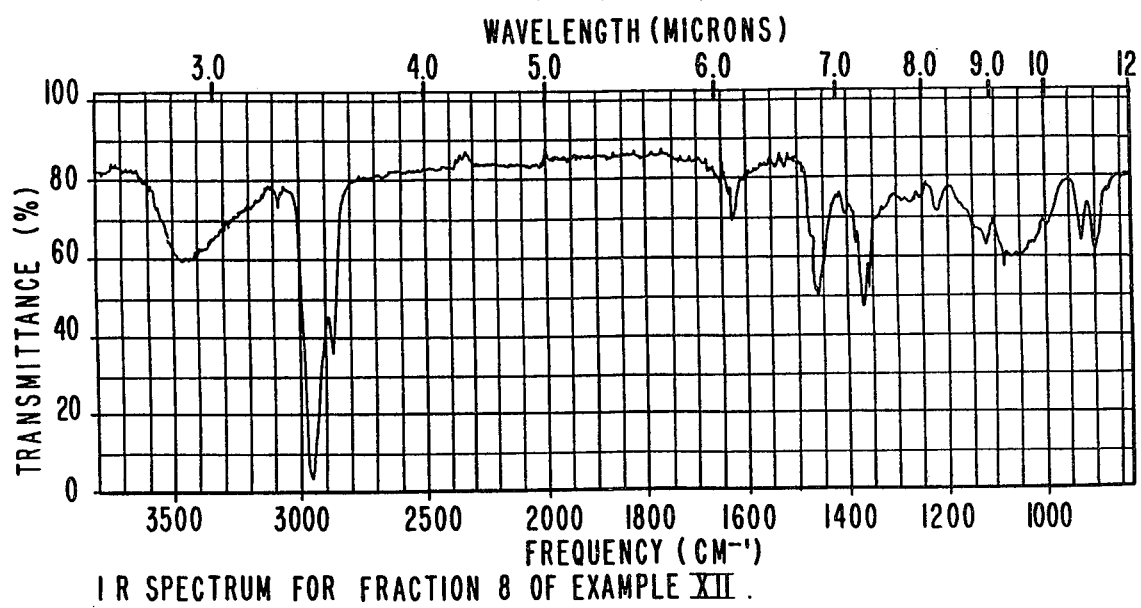
IR SPECTRUM FOR FRACTION 8 OF EXAMPLE XII.
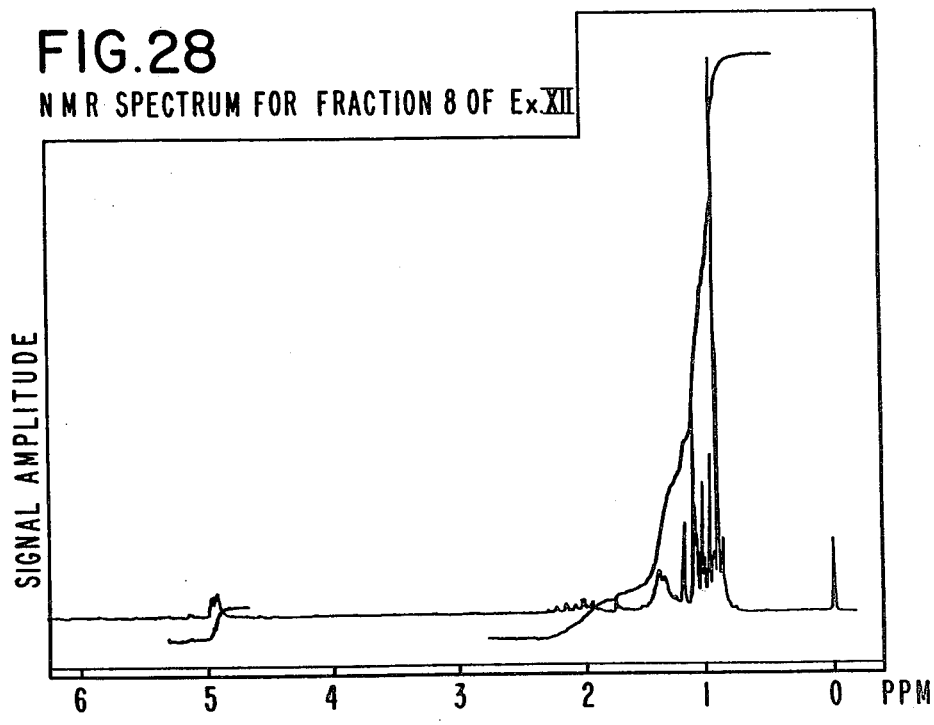

BRANCHED CHAIN OLEFINIC ALCOHOLS, THIOLS, ESTERS AND ETHERS, ORGANOLEPTIC USES THEREOF, PROCESSES FOR PREPARING SAME AND INTERMEDIATES THEREFOR

This is a divisional of application Ser. No. 322,734, filed Nov. 19, 1981, now U.S. Pat. No. 4,375,005, which, in turn, is a continuation-in-part of application for U.S. Patent, Ser. No. 212,887 filed on Dec. 4, 1980, now U.S. Pat. No. 4,318,934 issued Mar. 9, 1982.

BACKGROUND OF THE INVENTION

Materials which can provide amber, woody, camphoraceous, floral, orris-like and fruity aroma profiles with patchouli-like topnotes particularly those materials which are relatively inexpensive are highly sought after in the art of perfumery. Many of the natural materials which provide such fragrance profiles and contribute desired nuances to perfumery compositions and perfumed article substances are high in cost, vary in quality from one batch to another and/or are generally subject to the usual variations of natural products.

There is, accordingly, a continuing effort to find synthetic materials which will replace the essential fragrance notes provided by natural essential oils or compositions thereof. Unfortunately, many of these synthetic materials either have the desired nuances only to a relatively small degree or else contribute undesirable or unwanted odor to the composition. The search for materials which can provide a more refined amber, woody, camphoraceous, orris-like, fruity and patchouli-like aroma have been difficult and relatively costly in the areas of both natural products and synthetic products.

In addition, artificial flavoring agents for foodstuffs have received increasing attention in recent years. In many years, such food flavoring agents have been preferred over natural flavoring agents at least in part due to their diminished cost and their reproducible flavor qualities. For example, natural food flavoring agents such as extracts, concentrates and the like are often subject to wide variations due to changes in the quality, type and treatment of the raw materials. Such variations can be reflected in the end product and result in unfavorable flavor characteristics in said end product. Additionally, the presence of the natural product in the ultimate food may be undesirable because of increased tendency to spoil. This is particularly troublesome in food and food uses where such products as dips, soups, chips, sausages, gravies and the like are apt to be stored prior to use.

The fundamental problem in creating artificial flavor agents is that the artificial flavor to be achieved be as natural as possible. This generally proves to be a difficult task since the mechanism for flavor development in many foods is not completely known. This is noticeable in products having nutty, earthy, woody-balsamic, fresh walnut kernel and walnut skin flavor characteristics.

Reproduction of nutty, earthy, woody-balsamic, fresh walnut kernel and walnut skin flavor and aroma has been the subject of long and continuing searches by those engaged in production of foodstuffs and beverages. The severe shortage of food in many parts of the world has given rise to the development of previously unused sources of protein which are unpalatable. Accordingly, the need has arisen for the use of flavoring materials which will make such sources of protein palatable to human sensory organs.

Even more desirable is a product that can serve to substitute for difficult-to-obtain natural perfumery oils and at the same time substitute for natural flavoring ingredients in both foodstuffs as well as in tobacco.

Perfumery materials which are inexpensive such as dihydro linalool(3,7-Dimethyl-6-octen-3-ol), and dihydro myrcenol (3-Methylene-7-methyloctanol-7) do not provide the patchouli-like orris-like fragrance profiles that are provided by the more expensive, more complex molecules such as patchouli alcohol having the structure:

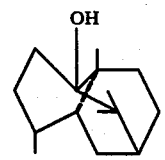

Dihydro linalool according to "Perfume and Flavor Chemicals (Aroma Chemicals)" by Steffen Arctander (1969) having the structure:

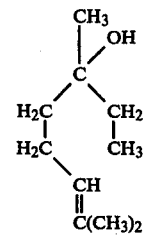

at Monograph 960 is indicated to have a fresh, floral, citrusy aroma which is less woody than linalool and more powerful and more lime-like than tetrahydro linalool. On the other hand, dihydro myrcenol having the structure:

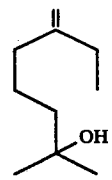

(at number 964 of Arctander) is described as being powerful, fresh lime-like overall citrusy, floral and sweet with little or no terpenic undertones. Dihydro myrcenyl acetate described at Monograph 965 of Arctander having the structure:

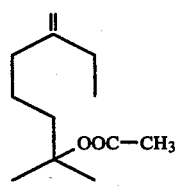

is described as sweet, spicy, herbaceous, fresh and somewhat fruity with a bergamot-lime character but poor tenacity.

No chemicals described in a prior art such as dihydro myrcenyl acetate, dihydro myrcenol or dihydro linalool have aroma profiles or chemical structures even remotely similar to the compounds of our invention.

BRIEF DESCRIPTION OF THE DRAWINGS

FIG. AA represents the GLC profile for the reaction product of Example A using a 70% sulfuric acid catalyst at 35%C.

FIG. AB represents the GLC profile for the reaction product of Example A using an Amberlyst® 15 acidic ion exchange resin catalyst at a temperature of 150° C.

FIG. AC represents the GLC profile for the reaction product of Example A, using an Amberlyst® 15 catalyst at 100° C.

FIG. AD represents the GLC profile for the reaction product of Example A, using a sulfuric acid catalyst and an alpha-methylstyrene diluent at 35°

FIG. AE represents the GLC profile for the reaction product of Example I, using a sulfuric acid catalyst, at 35° C. and an alpha-methyl styrene diluent according to the conditions of United Kingdom Patent Specification No. 796,130 (distilled reaction product). Distillation range: vapor temperature 36°–40° C.; liquid temperature 74°–94° C.; pressure 4–5 mm/Hg.

FIG. BA represents the NMR spectrum for Peak 1 of the GLC profile of FIG. AE.

FIG. BB represents the infra-red spectrum for Peak 1 of the GLC profile of FIG. AE.

FIG. CA represents the NMR spectrum fir Peak 2 of the GLC profile of FIG. AE.

FIG. CB represents the infra-red spectrum for Peak 2 of the GLC profile of FIG. AE.

FIG. D represents the NMR spectrum for Peak 2 of the GLC profile of FIG. AB.

Figure 1:
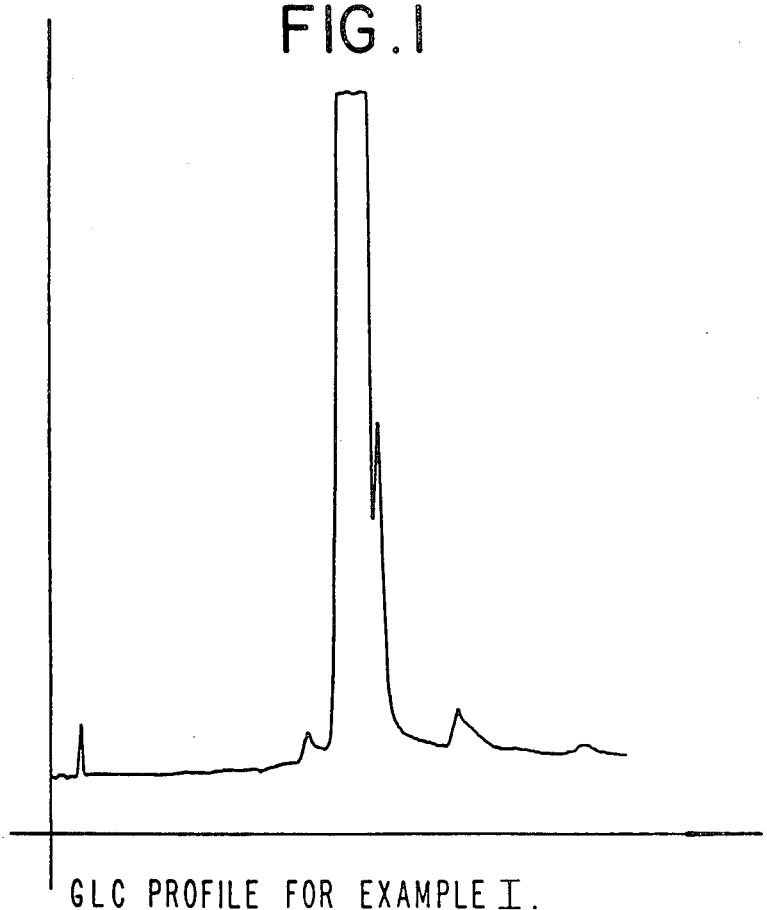

FIG. 1 sets forth the GLC profile for the reaction product of Example I, containing compounds defined according to the structure:

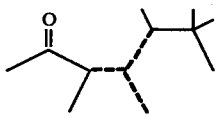

wherein in each molecule of the mixture, one of the dashed lines is a carbon-carbon double bond and the other of the dashed lines are carbon-carbon single bonds.

Figure 2A:
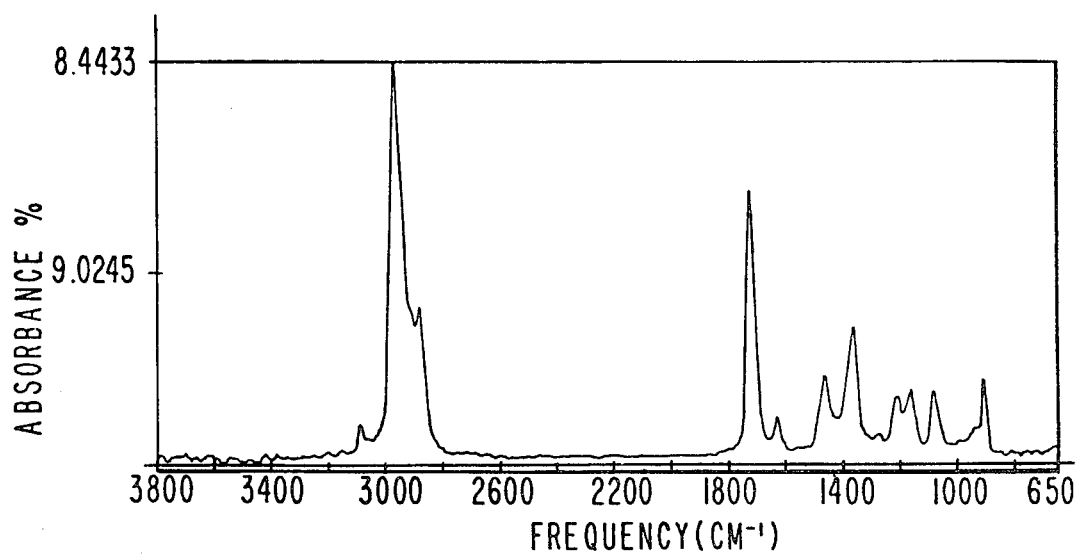

FIG. 2A represents the infra-red spectrum of Peak 3 of the GLC profile of FIG. 1.

FIG. 2B represents the infra-red spectrum of Peak 4 of the GLC profile of FIG. 1.

FIG. 2C represents the infra-red spectrum for Peak 5 of the GLC profile of FIG. 1.

Figure 2D:
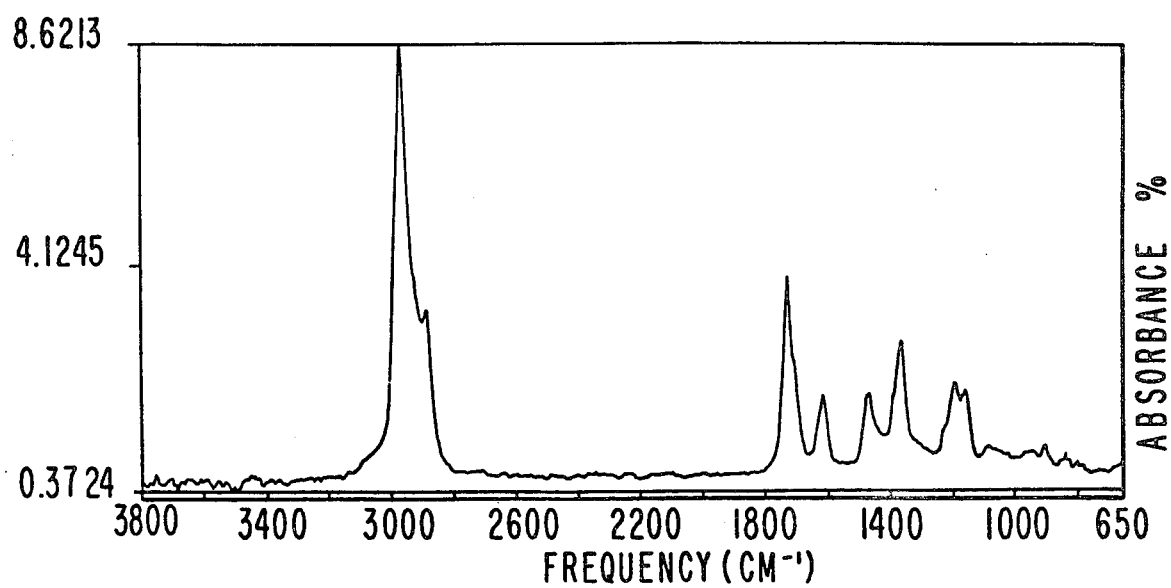

FIG. 2D represents the infra-red spectrum for Peak 6 of the GLC profile of FIG. 1.

Figure 2E:
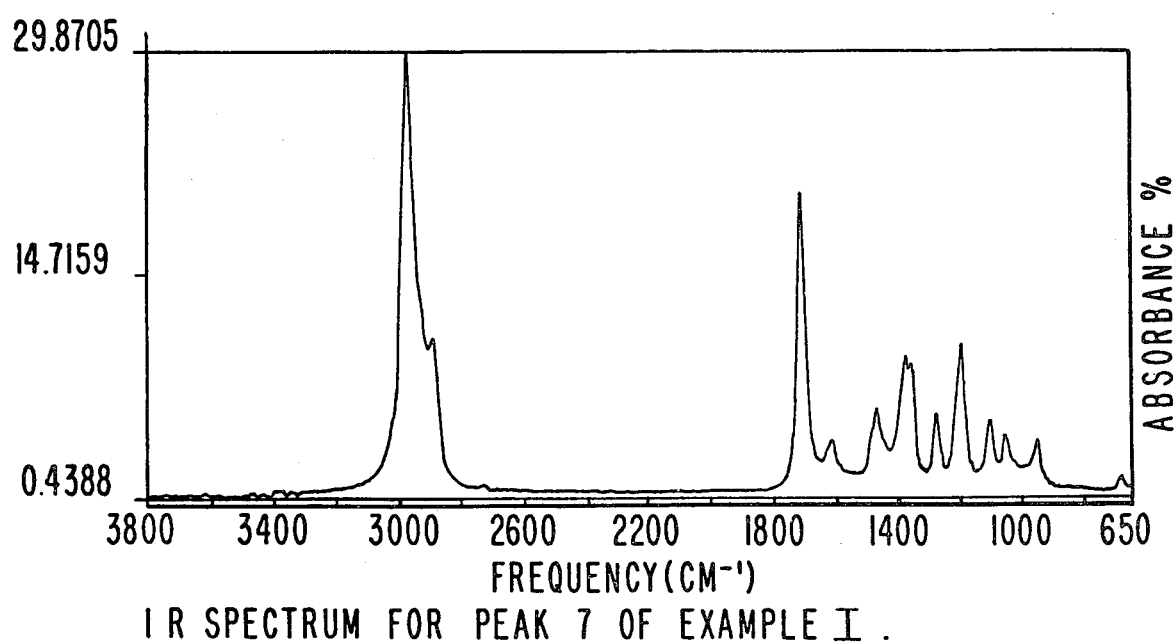

FIG. 2E represents the infra-red spectrum for Peak 7 of the GLC profile of FIG. 1.

FIG. 2F represents the infra-red spectrum for Peak 8 of the GLC profile of FIG. 1.

FIG. 2G represents the infra-red spectrum for Peak 9 of the GLC profile of FIG. 1.

Figure 2H:
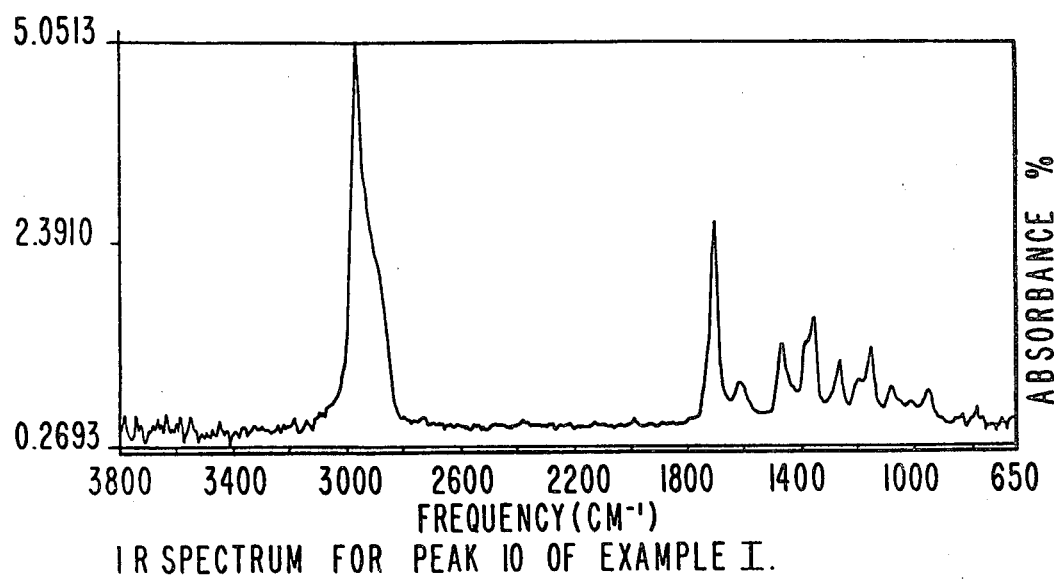

FIG. 2H represents the infra-red spectrum for Peak 10 of the GLC profile of FIG. 1.

Figure 2J:
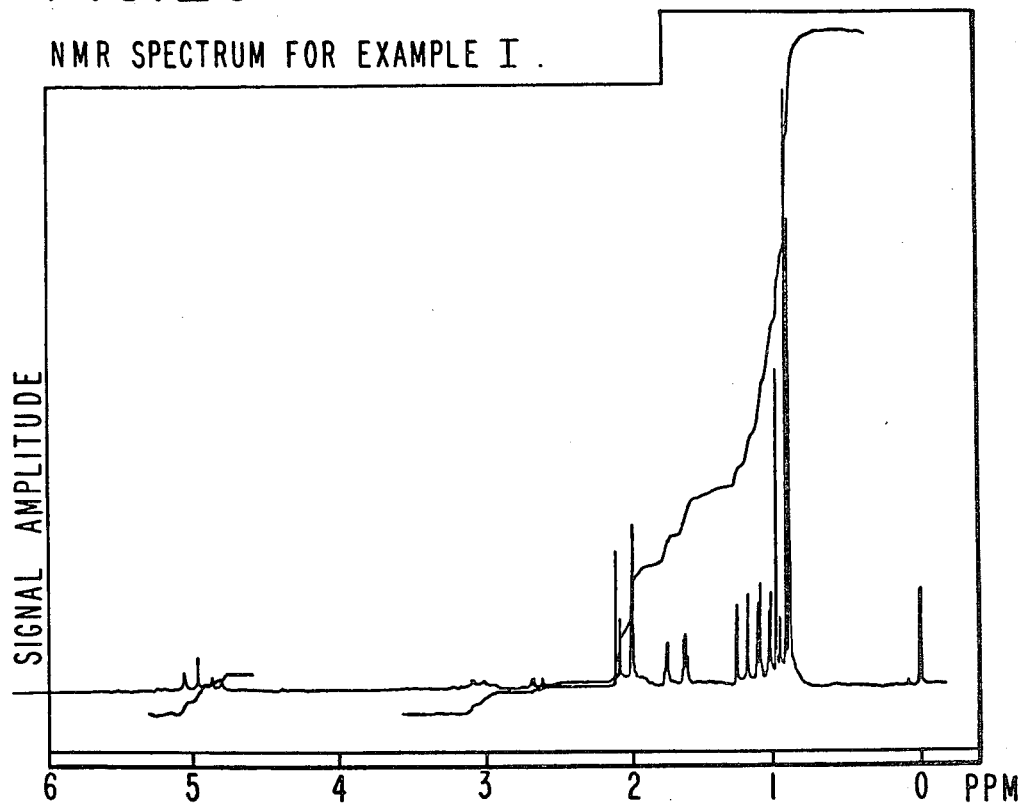

FIG. 2J represents the NMR spectrum for a mixture of compounds having the structures:

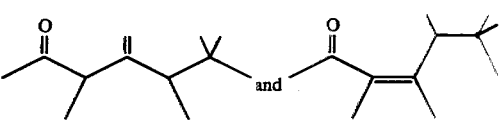

produced according to Example I.

Figure 2K:
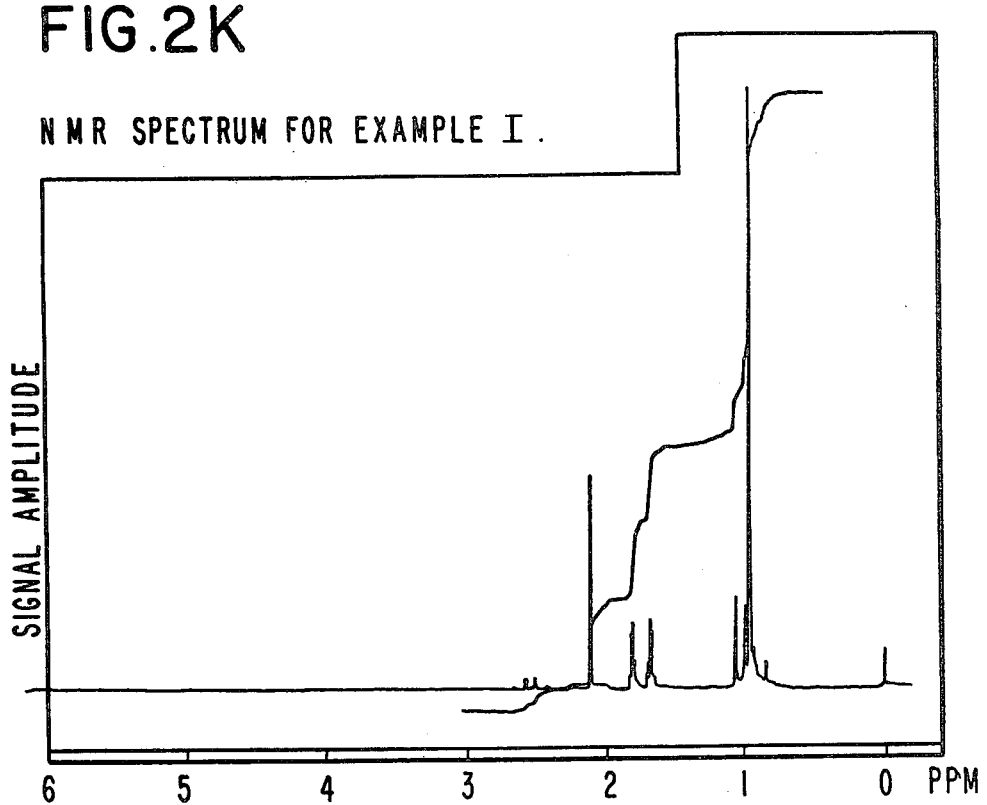

FIG. 2K represents the NMR spectrum for the compound having the structure:

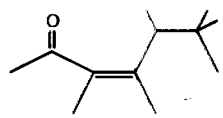

produced according to Example I.

Figure 2L:
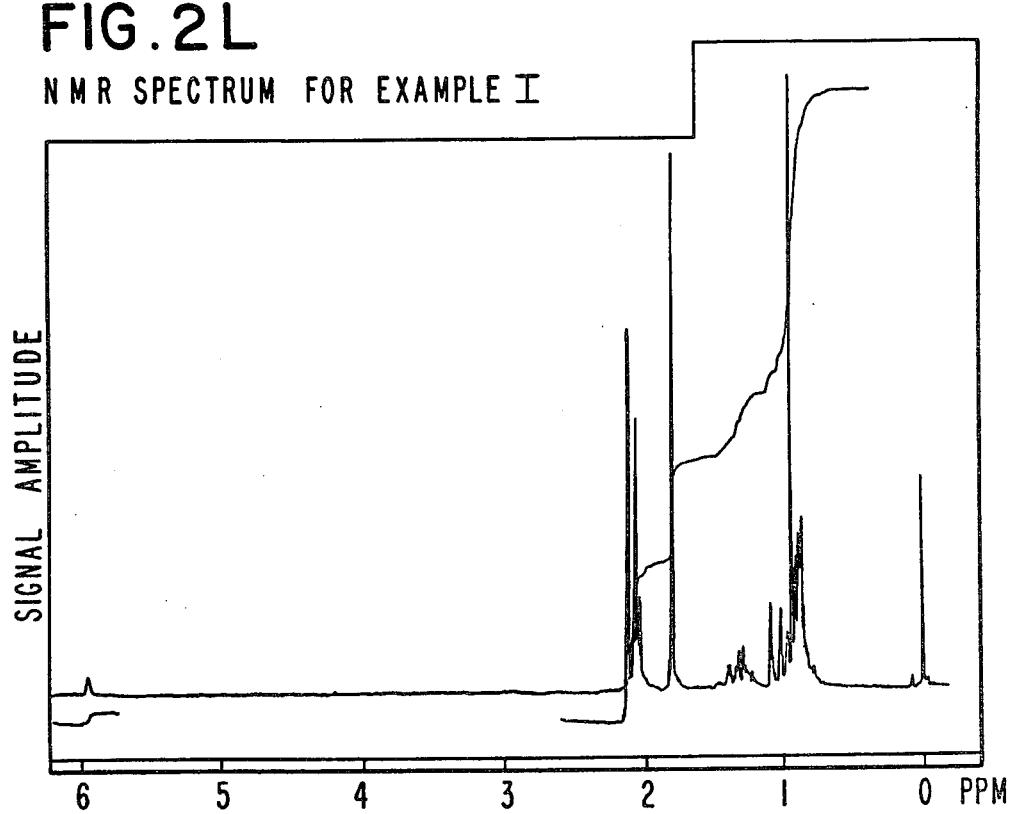

FIG. 2L represents the NMR spectrum for the compound containing the structure:

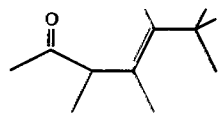

produced according to Example 1.

Figure 3:
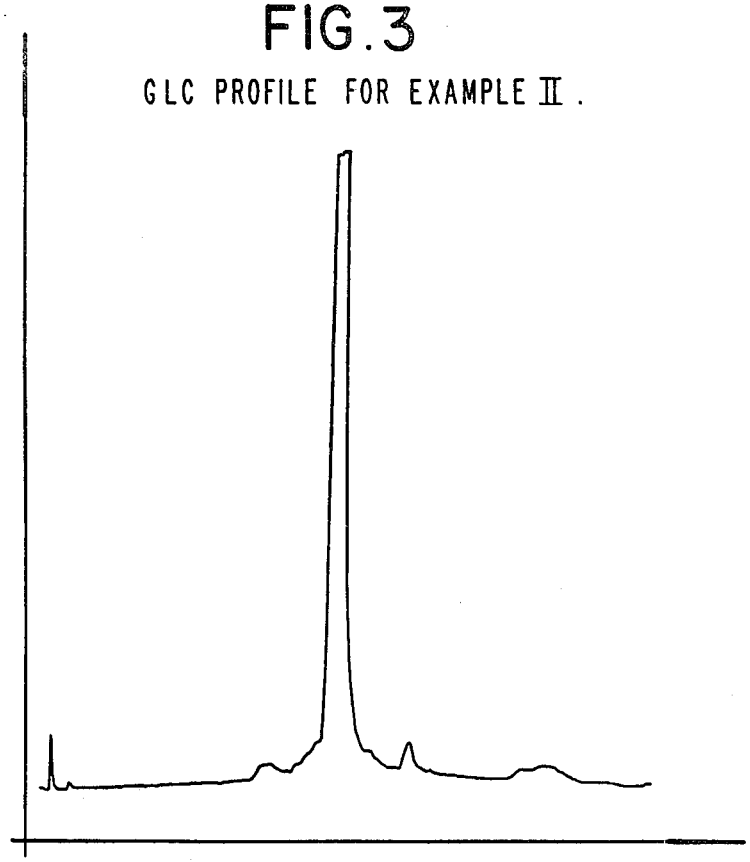

FIG. 3 represents the GLC profile for the reaction product of Example II containing a mixture of compounds, each of which is defined according to the generic structure:

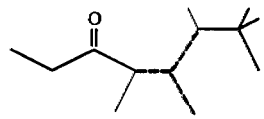

wherein in each molecule one of the dashed lines is a carbon-carbon double bond and each of the other of the dashed lines are carbon-carbon single bonds.

Figure 4:
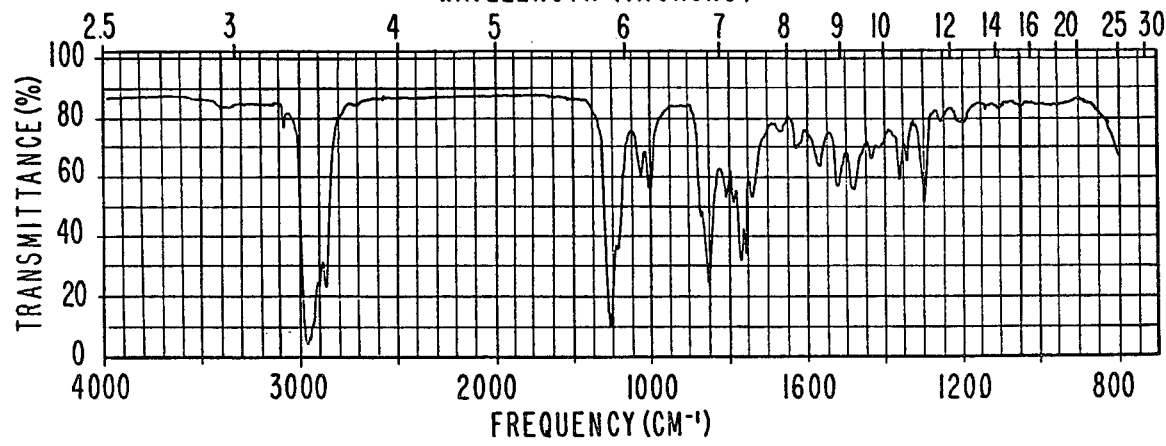

FIG. 4 represents the infra-red spectrum for the product produced according to Example II containing the compounds having the structures:

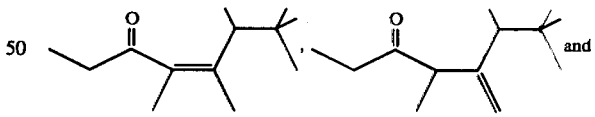

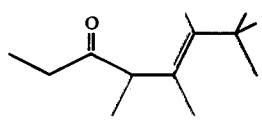

Figure 5:
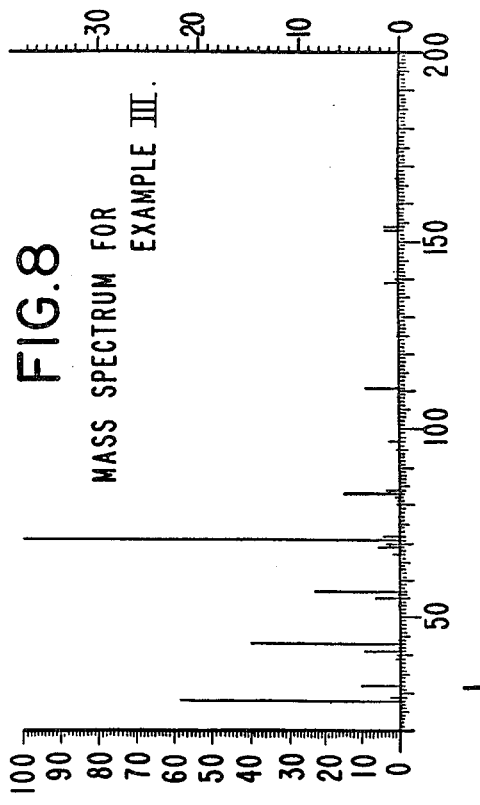

FIG. 5 represents the mass spectrum for the reaction product of Example II, containing the compounds having the structures:

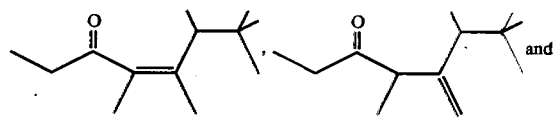

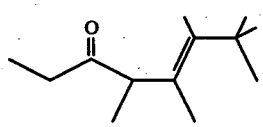

Figure 6:
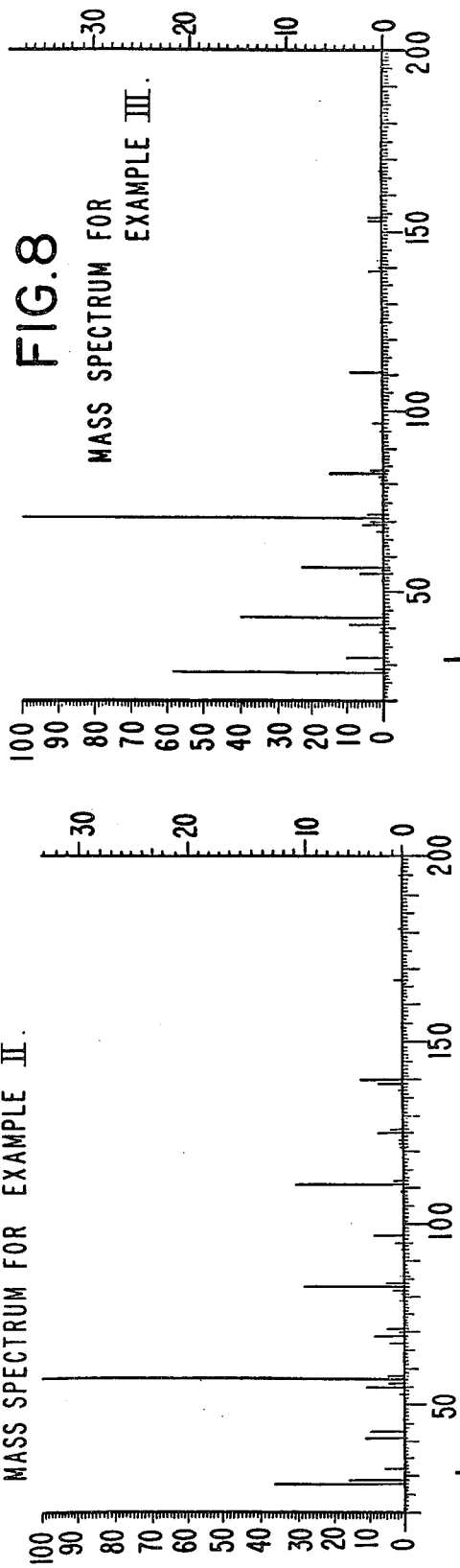

FIG. 6 represents the GLC profile for the reaction product of Example III containing compounds defined according to the generic structure:

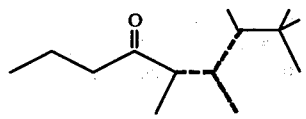

wherein in each of the molecules of the mixture, one of the dashed lines represents a carbon-carbon double bond and the other of the dashed lines represent carbon-carbon single bonds.

FIG. 7 represents the infra-red spectrum for the reaction product of Example III containing the compounds having the structures:

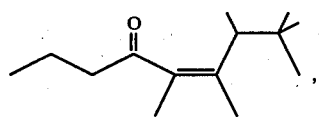

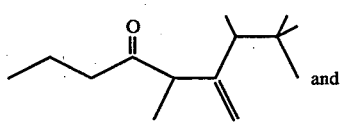
and

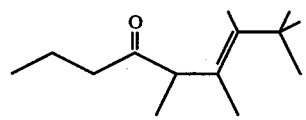

Figure 8:
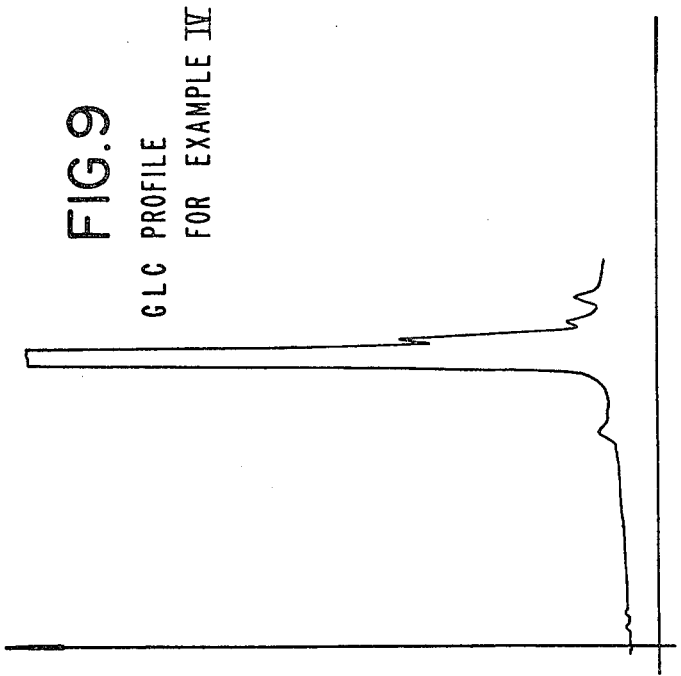

FIG. 8 represents the mass spectrum for the reaction product of Example III containing the compounds having the structures:

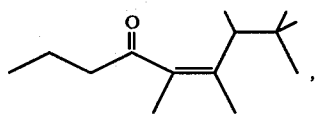

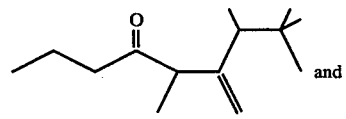
and

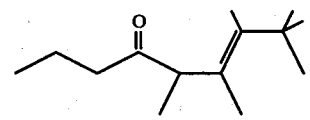

Figure 9:
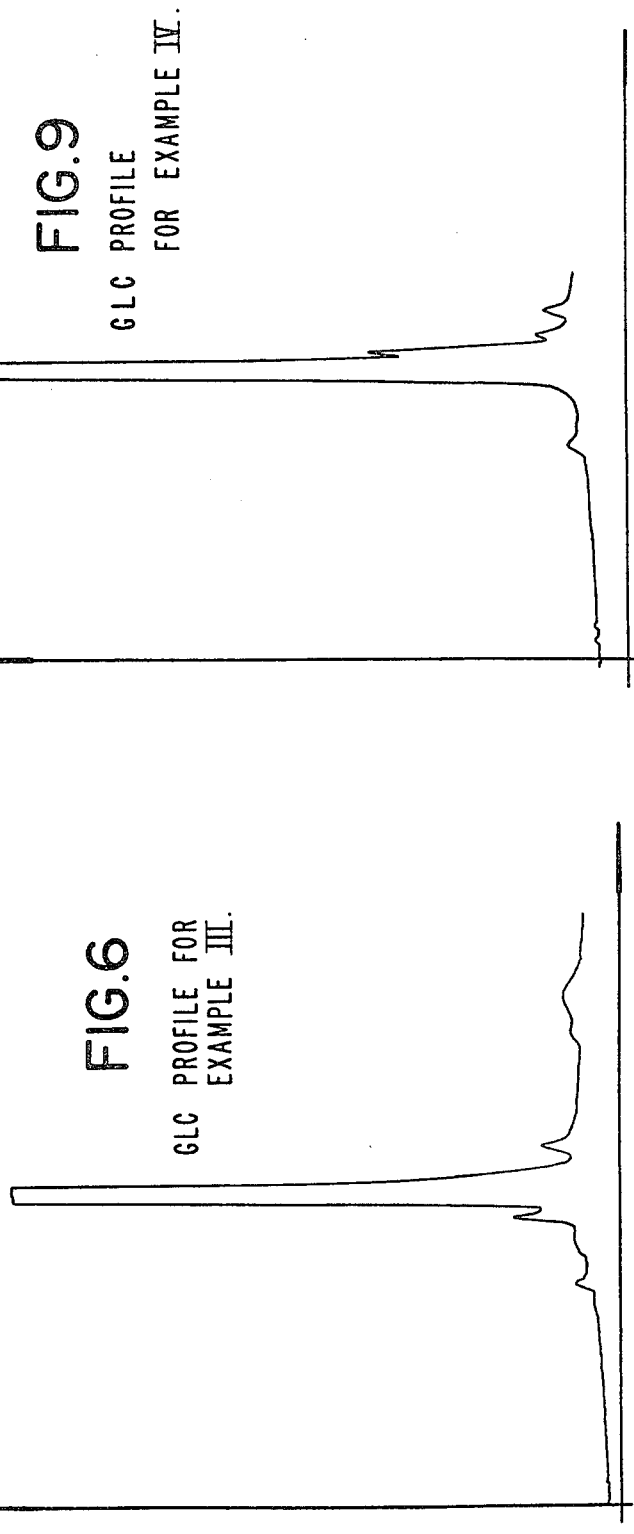

FIG. 9 represents the GLC profile for the reaction product of Example IV, containing a mixture of compounds, each of which is defined according to the generic structure:

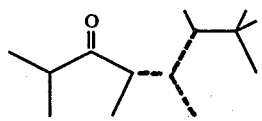

wherein in each of the molecules, one of the dashed lines represents a carbon-carbon double bond and each of the other of the dashed lines represent carbon-carbon single bonds.

FIG. 10 represents the infra-red spectrum for the reaction product of Example IV containing the compounds having the structures:

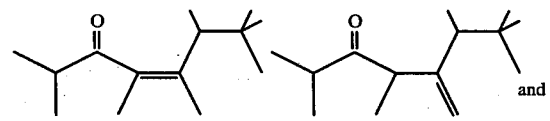

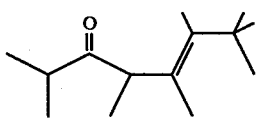

FIG. 11 represents the mass spectrum for the reaction product of Example IV containing the compounds having the structures:

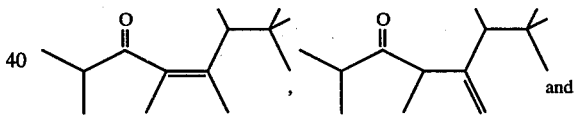

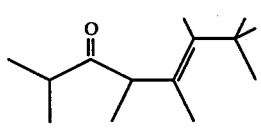

FIG. 12 represents the GLC profile for the reaction product of Example VA containing structures defined according to the genus having the structure:

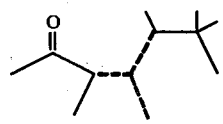

wherein in each of the molecules of the mixture, one of the dashed lines represents a carbon-carbon double bond and each of the other of the dashed lines represent carbon-carbon single bonds.

Figure 13:
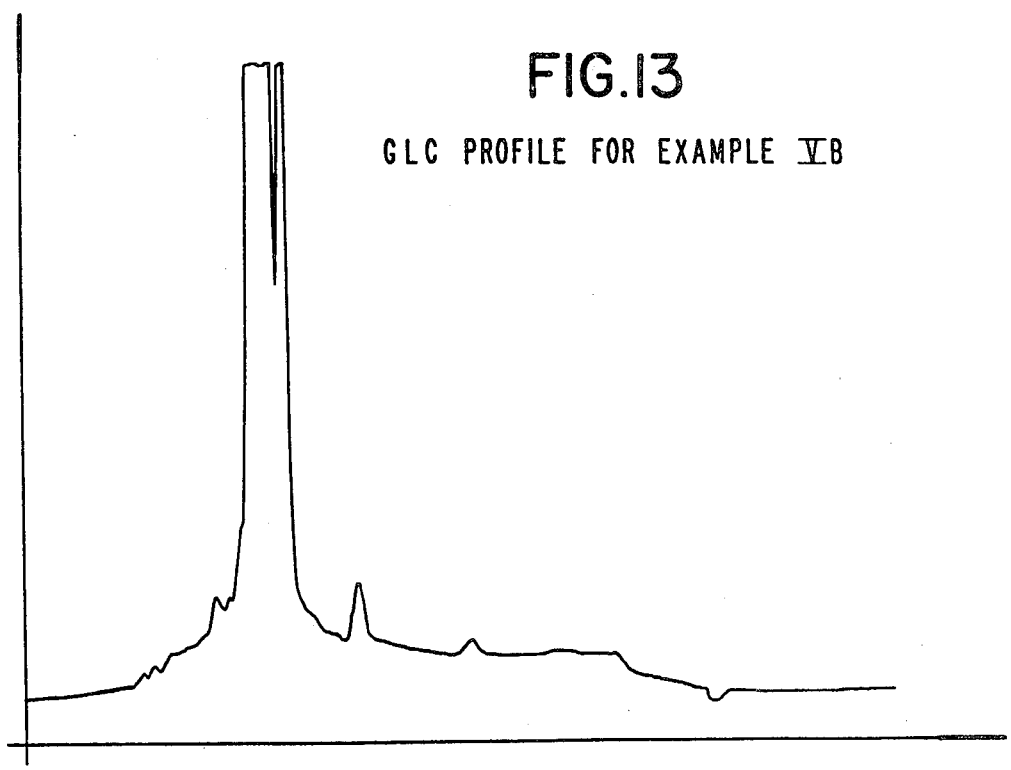

FIG. 13 represents the GLC profile for the reaction product of Example VB containing a mixture of compounds defined according to the structure:

wherein in each of the molecules of the mixture, one of the dashed lines represents a carbon-carbon double bond and each of the other of the dashed lines represent carbon-carbon single bonds.

Figure 14:
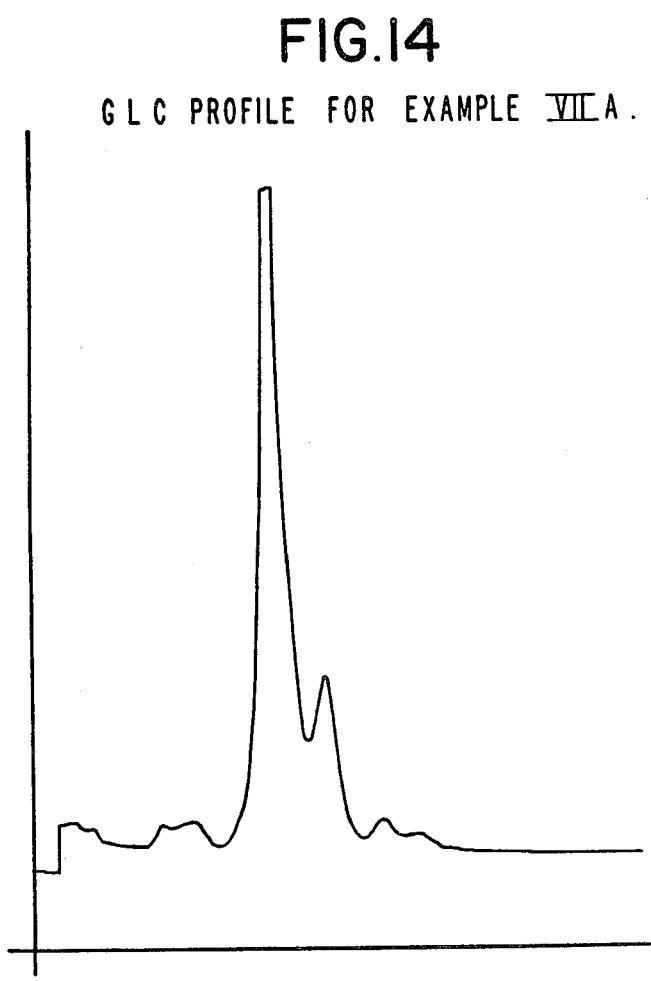

FIG. 14 represents the GLC profile for the reaction product of Example VIIA containing a mixture of compounds defined according to the genus having the structure:

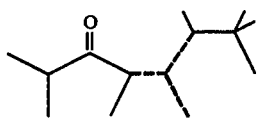

wherein in each of the molecules of the mixture, one of the dashed lines represents a carbon-carbon double bond and each of the other of the dashed lines represents carbon-carbon single bonds.

Figure 15:
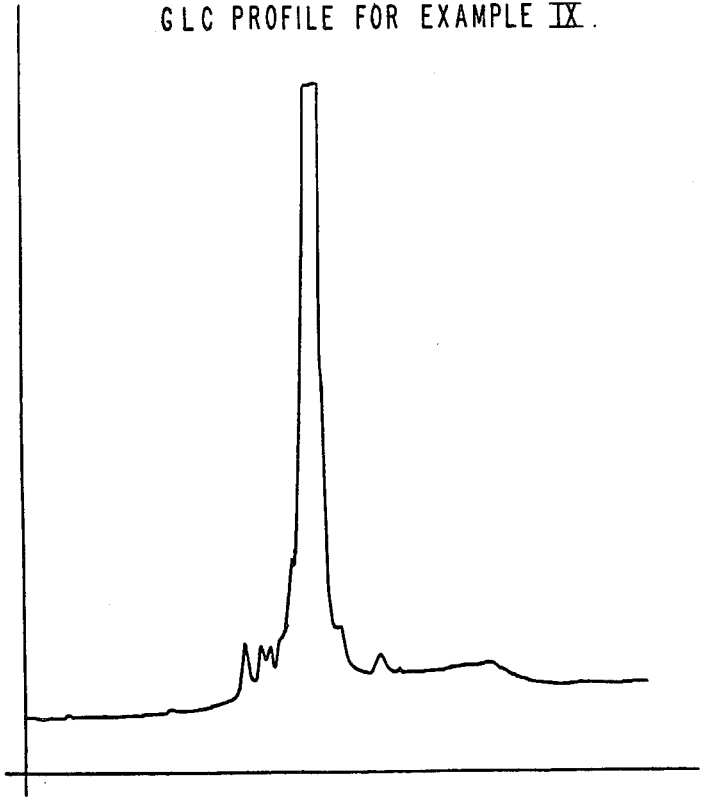

FIG. 15 represents the GLC profile for the reaction product of Example IX containing a mixture of compounds defined according to the structure:

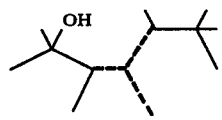

wherein in each of the molecules one of the dashed lines represents a carbon-carbon double bond and each of the other of the dashed lines represent carbon-carbon single bonds.

Figure 16:
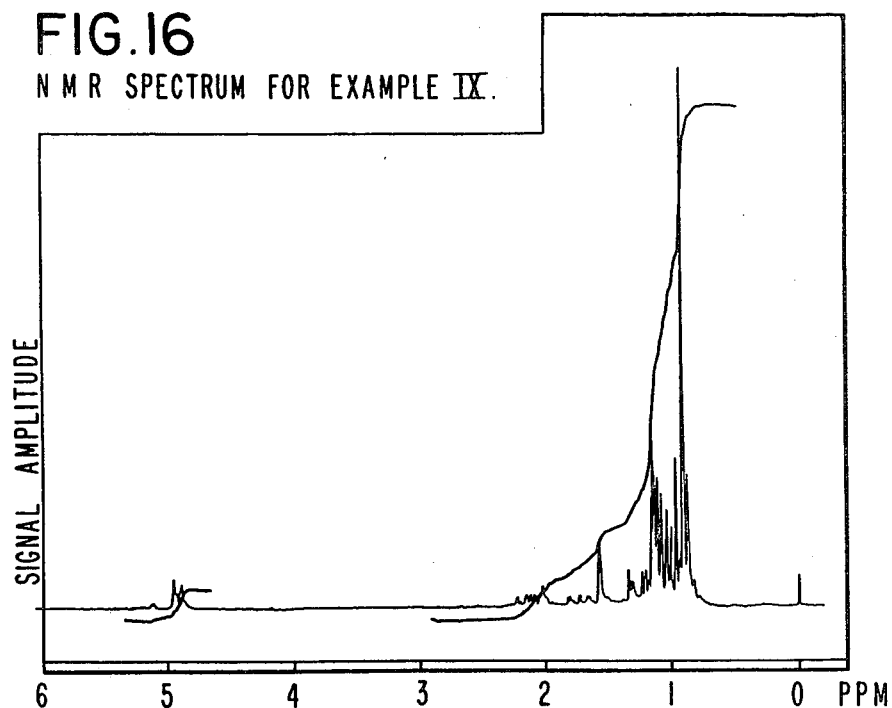

FIG. 16 is the NMR spectrum for the reaction product of Example IX containing a mixture of compounds having the structures defined according to the following structure:

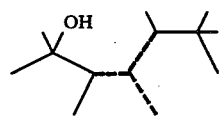

wherein in each of the molecules of the mixture one of the dashed lines represents a carbon-carbon double bond and each of the other of the dashed lines represent carbon-carbon single bonds.

Figure 17:
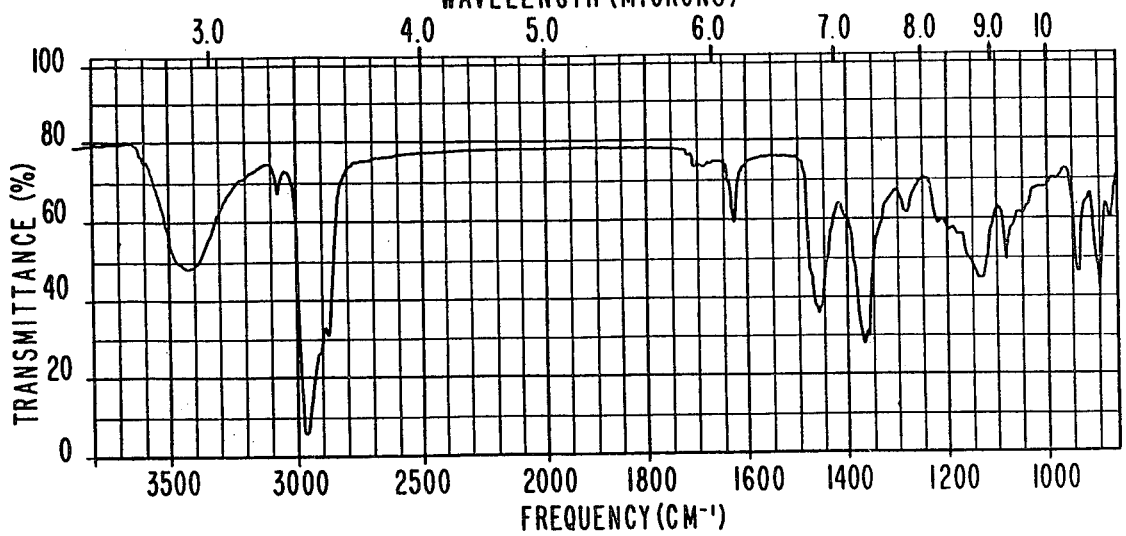

FIG. 17 is the infra-red spectrum for the reaction product of Example IX containing the compounds defined according to the structure:

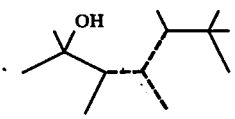

wherein in each of the molecules in the resulting mixture one of the dashed lines represents a carbon-carbon doble bond and each of the other of the dashed lines represent carbon-carbon single bonds.

Figure 18:
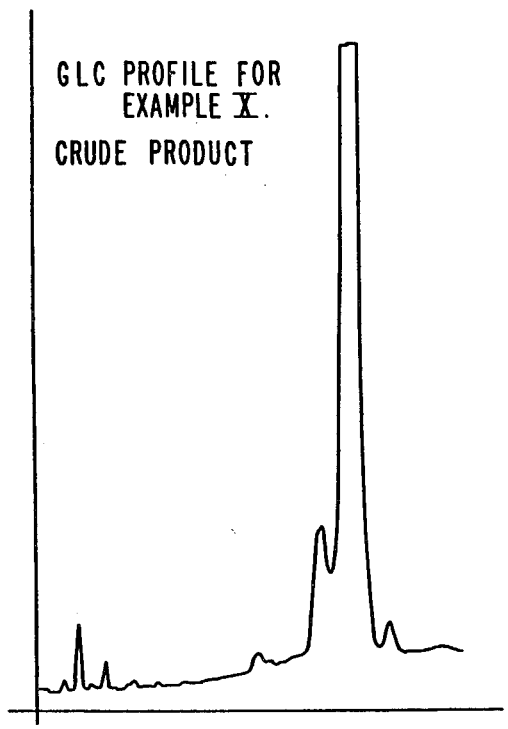

FIG. 18 is the GLC profile of the crude reaction product of Example X containing the compounds defined according to the structure:

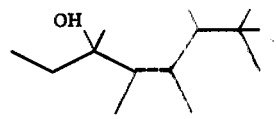

wherein in each of the molecules, one of the dashed lines represents a carbon-carbon single bond and each of the other of the dashed lines represent carbon-carbon double bonds.

Figure 19:
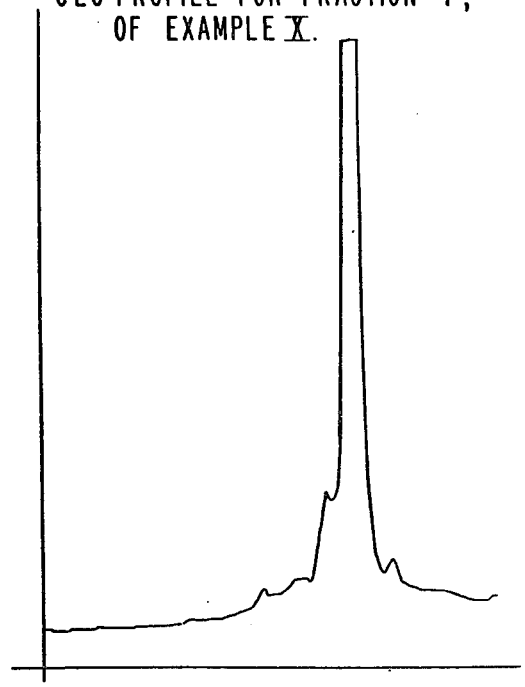

FIG. 19 is the GLC profile for fraction 4 of the distillation product of the reaction product of Example X containing the compounds having the structure:

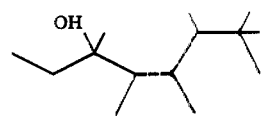

wherein in each of the molecules one of the dashed lines represents a carbon-carbon double bond and each of the other of the dashed lines represent carbon-carbon single bonds.

FIG. 20 is the infra-red spectrum for fraction 4 of the distillation product of the reaction product of Example X containing a mixture of compounds defined according to the structure:

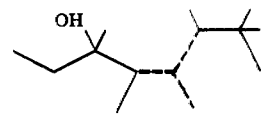

wherein in each of the molecules one of the dashed lines represents a carbon-carbon double bond and each of the other of the dashed lines represent carbon-carbon single bonds.

FIG. 21 is the GLC profile of the crude reaction product of Example XI containing a mixture of compounds defined according to the structure:

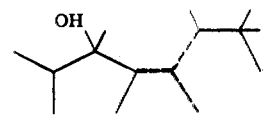

wherein in each of the molecules one of the dashed lines represents a carbon-carbon double bond and each of the other of the dashed lines represent carbon-carbon single bonds.

FIG. 22 is the GLC profile for fraction 7 of the distillation product of the reaction product of Example XI containing a mixture of compounds defined according to the structure:

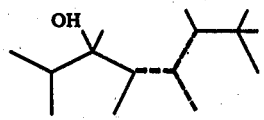

wherein in each of the molecules one of the dashed lines represents a carbon-carbon double bond and each of the other of the dashed lines represent carbon-carbon single bonds.

FIG. 23 is the infra-red spectrum for fraction 7 of the distillation product of the reaction product of Example XI containing a mixture of compounds defined according to the structure:

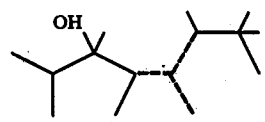

wherein in each of the molecules one of the dashed lines is a carbon-carbon double bond and each of the other of the dashed lines represent carbon-carbon single bonds.

FIG. 24 is the NMR spectrum for fraction 7 of the distillation product of the reaction product of Example XI containing a mixture of compounds defined according to the structure:

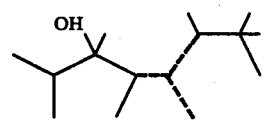

wherein in each of the molecules one of the dashed lines represents a carbon-carbon double bond and each of the other of the dashed lines represent carbon-carbon single bonds.

Figure 25:
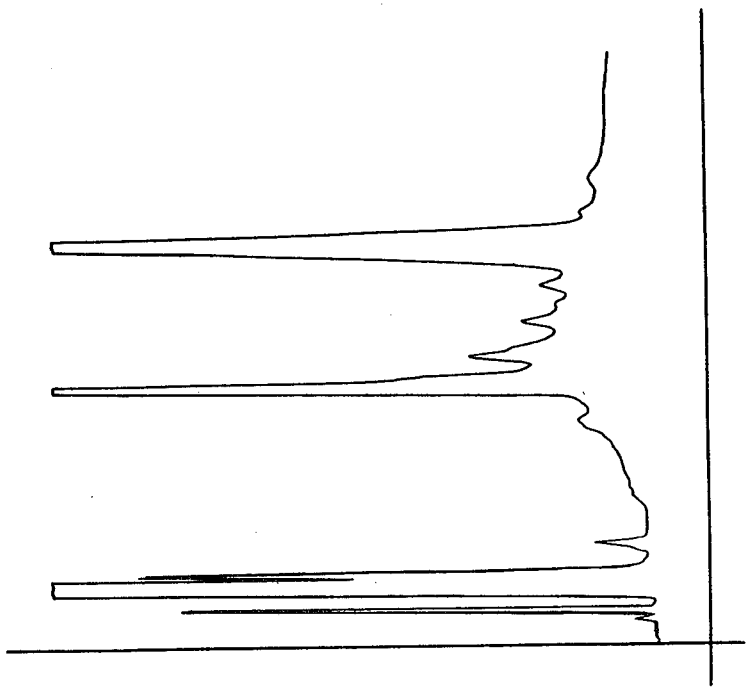

FIG. 25 is the GLC profile for the crude reaction product produced according to the procedure of Example XII containing a mixture of compounds defined according to the structure:

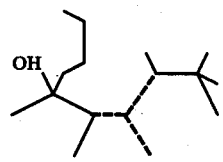

wherein in each of the molecules one of the dashed lines represents a carbon-carbon double bond and each of the other of the dashed lines represent carbon-carbon single bonds.

Figure 26:
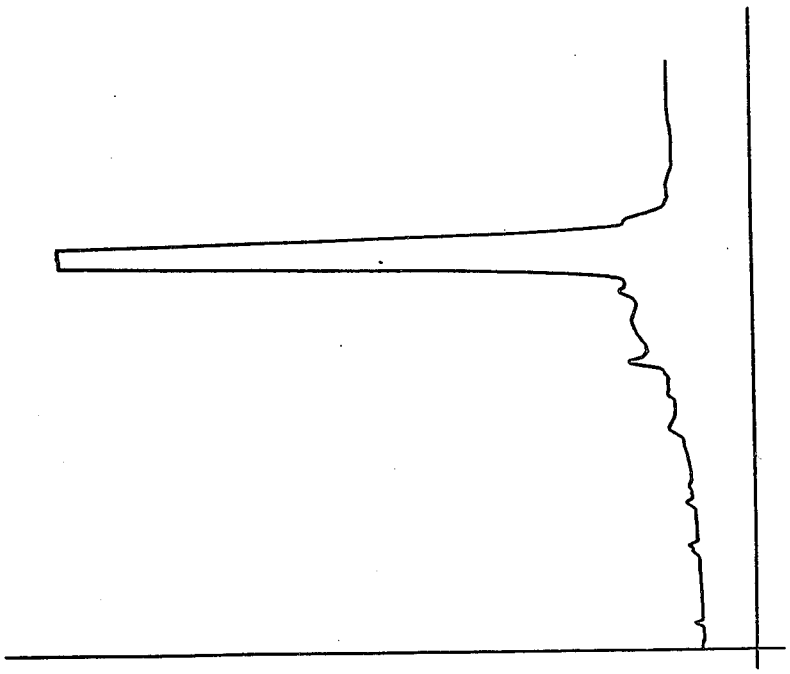

FIG. 26 is the GLC profile for fraction 8 of the distillation product of the reaction product of Example XII containing a mixture of compounds defined according to the structure:

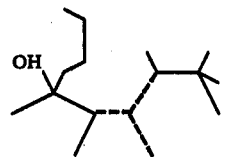

wherein in each of the molecules one of the dashed lines represents a carbon-carbon double bond and each of the other of the dashed lines represent carbon-carbon single bonds.

FIG. 27 is the infra-red spectrum for fraction 8 of the distillation product of the reaction product of Example XII containing a mixture of compounds defined according to the structure:

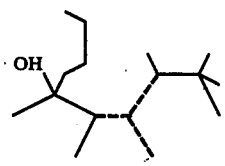

wherein one of the dashed lines is a carbon-carbon double bond and each of the other of the dashed lines represent carbon-carbon single bonds.

FIG. 28 is the NMR spectrum for fraction 8 of the distillation product of the reaction product of Example XII containing the compounds defined according to the structure:

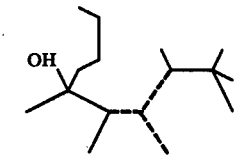

wherein in each of the molecules one of the dashed lines represents a carbon-carbon double bond and each of the other of the dashed lines represent carbon-carbon single bonds.

DISCLOSURES INCORPORATED BY REFERENCE HEREIN

U.S. application for letters patent Ser. No. 160,788 filed on June 19, 1980, now U.S. Pat. No. 4,287,084 (entitled: Use of Mixture of Aliphatic $C_{10}$ Branched Olefins in Augmenting or Enhancing the Aroma of Perfumes and/or Perfumed Articles) setting forth the use of the compounds having the structures:

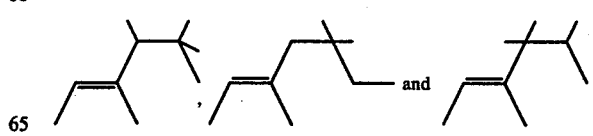

or generically the compounds defined according to the structure:

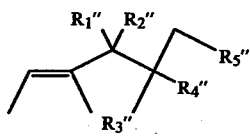

wherein $R_1''$, $R_2''$, $R_3''$, $R_4''$ and $R_5''$ represents hydrogen or methyl with three of $R_1''$, $R_2''$, $R_3''$, $R_4''$ and $R_5''$ representing methyl and the other two of $R_1''$, $R_2''$, $R_3''$, $R_4''$ and $R_5''$ representing hydrogen; application for U.S. letters patent Ser. No. 188,576 filed on Sept. 18, 1980, now U.S. Pat. No. 4,303,555, a continuation-in-part of Ser. No. 160,788 filed on June 19, 1980; and application for U.S. letters patent Ser. No. 184,132 filed on Sept. 4, 1980, now U.S. Pat. No. 4,321,255, entitled "Branched Ketones, Organoleptic Uses Thereof and Process for Preparing Same" disclosing the reaction:

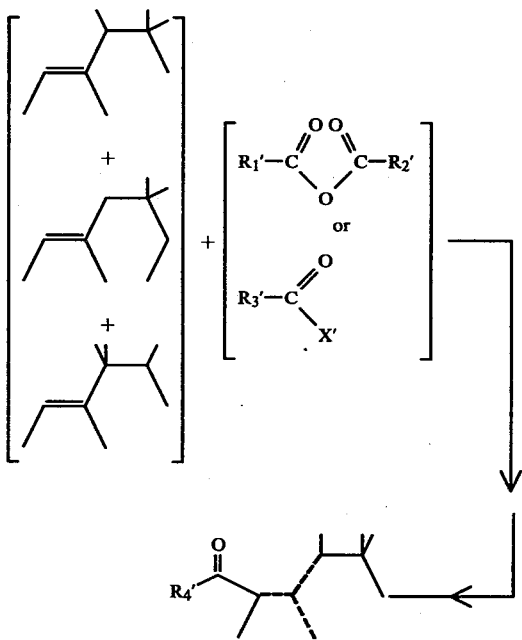

wherein $R_1'$, $R_2'$ and $R_3'$ represent $C_1$–$C_3$ lower alkyl and $R_4'$ is either of $R_1'$, $R_2'$ or $R_3'$ and wherein $X'$ is chloro or bromo.

The instant application relies on the compounds defined according to the generic structure:

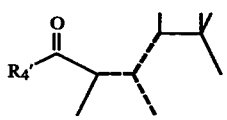

as a starting material wherein $R_4'$ is $C_1$–$C_3$ lower alkyl and wherein one of the dashed lines represents a carbon-carbon double bond and each of the other of the dashed lines represent carbon-carbon single bonds produced according to the process of application for U.S. letters patent Ser. No. 184,132 filed on Sept. 4, 1980 entitled "Branched Ketones, Organoleptic Uses Thereof and Process for Preparing Same."

THE INVENTION

It has now been determined that certain branched chain olefinic tertiary alcohols are capable of imparting a variety of flavors and fragrances to various consumable materials. Briefly, our invention contemplates branched chain unsaturated tertiary alcohols, thio alcohols, esters, ethers, thio esters, and thio ethers defined according to the generic structure:

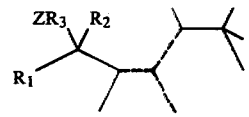

wherein Z represents oxygen or sulfur; wherein $R_1$ represents $C_1$–$C_4$ alkyl; wherein $R_2$ represents $C_1$–$C_4$ alkyl; wherein $R_3$ represents hydrogen, MgX, Li, $C_1$–$C_3$ lower alkyl and $C_1$–$C_3$ lower acyl; wherein one of the dashed lines represents a carbon-carbon double bond and each of the other of the dashed lines represent carbon-carbon single bonds and wherein X represents chloro, bromo or iodo. Thus, the compounds contemplated within the scope of our invention are either oxygenated compounds defined according to the structure:

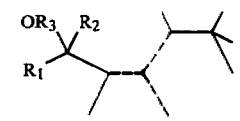

or sulfur containing compounds defined according to the structure:

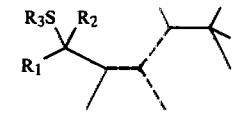

wherein $R_1$, $R_2$, $R_3$ and the dashed lines are defined as above.

The branched chain olefinic alcohols, thiols, esters and ethers, thio esters and thio ethers of our invention are either usable in admixture with one another, or the isomers are usable in admixture with one another such as mixtures of compounds defined according to the structure:

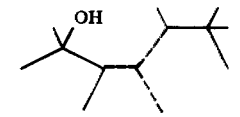

wherein one of the dashed lines of each of the molecules of the mixture represents a carbon-carbon double bond and each of the other of the dashed lines of each of the molecules of the mixture represent carbon-carbon single bonds or they may be used as individual compounds which are, for example, defined according to structures such as:

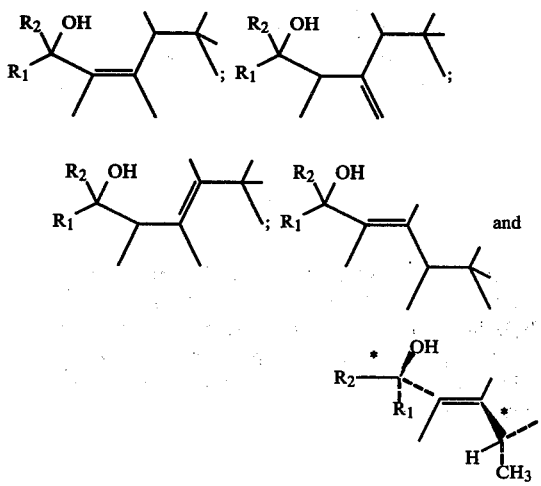

wherein the compound having the structure:

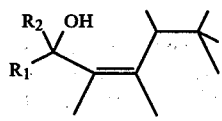

differs from the compound having the structure:

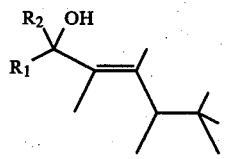

and that one is "cis" with respect to the methyl groups on the carbon atoms which make up the carbon-carbon double bond and wherein the structure:

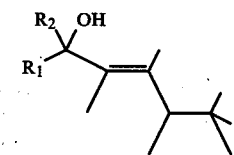

represents a "trans" isomer with respect to the methyl moieties bonded to the carbon atoms making up the carbon-carbon double bond and wherein the structure:

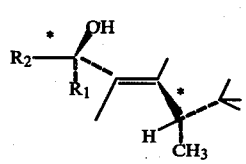

represents a stereo isomeric configuration wherein the carbon atoms having the "*" are asymetric carbon atoms in the molecule and wherein the compound is a "trans" isomer with respect to the methyl moieties bonded to the carbon atoms which make up the carbon-carbon double bond.

The branched chain olefinic alcohols, thiols, esters, ethers, thio esters and thio ethers of our invention are obtained by means of reaction of the ketones produced according to application for U.S. letters patent Ser. No. 184,132 filed on Sept. 4, 1980 entitled "BRANCHED KETONES, ORGANOLEPTIC USES THEREOF AND PROCESS FOR PREPARING SAME" with alkyl lithium compounds or alkyl magnesium halide compounds to form organometallic intermediates defined according to the structures:

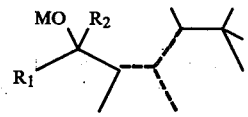

wherein M represents MgX or Li; wherein $R_1$ and $R_2$ each represent $C_1$–$C_4$ lower alkyl; wherein one of the dashed lines represents a carbon-carbon double bond and each of the other of the dashed lines represent carbon-carbon single bonds and wherein X represents chloro, bromo or iodo. This organometallic intermediate may be isolated or retained in situ in the reaction medium and then hydrolyzed to form the alcohols of our invention defined according to the structures:

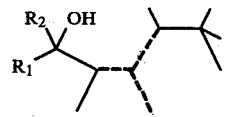

These alcohols may then be reacted with $P_2S_5$ to form the thiols of our invention according to the reaction:

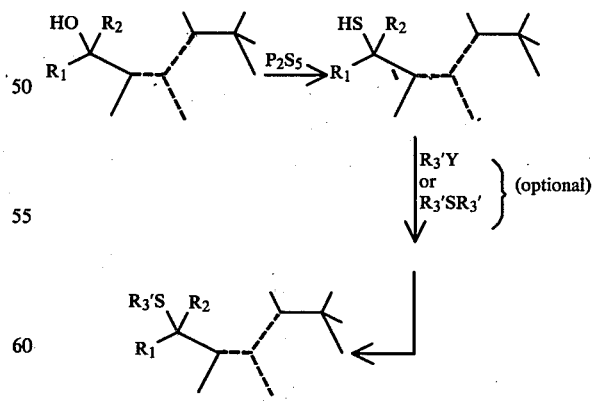

and these thiols may either be used as is or may optionally be reacted with $R_3'Y$ or $R_3'SR_3'$ to form the thio ethers or thio esters of our invention according to the reaction sequence:

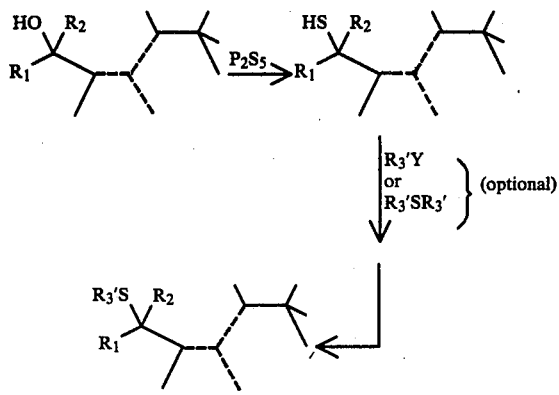 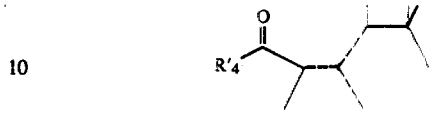

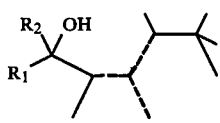

wherein R₃' represents $C_1$-$C_3$ lower alkyl or $C_1$-$C_3$ acyl. Optionally, the alcohols of our invention having the structure:

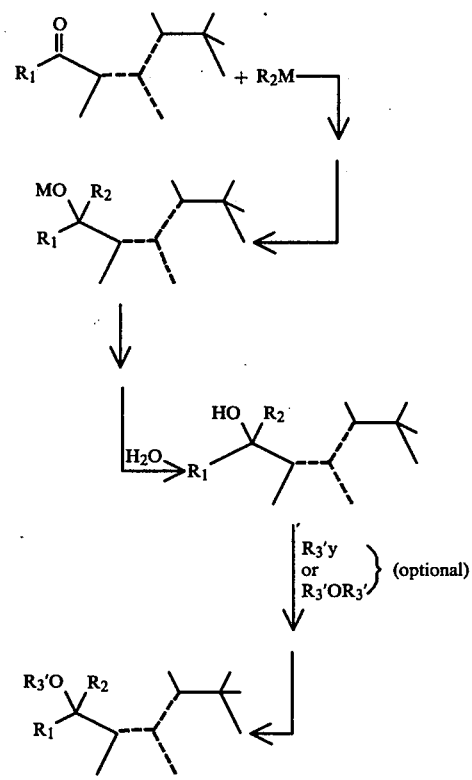

may be reacted with R₃'Y or R₃'OR₃' to form the esters or ethers of our invention and the reaction forming the alcohols, esters and ethers of our invention is illustrated by the reaction:

The foregoing reaction also shows the formation of the organometallic compounds contemplated by our invention. In the foregoing reaction sequences R₃' represents $C_1$-$C_3$ alkyl or acyl and Y represents chloro, bromo or iodo.

The reaction temperature for reacting the alkyl lithium derivative or the Grignard reagent with the ketone having the structure:

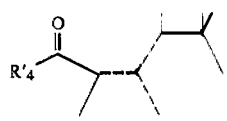

may vary from 25° C. up to 50° C. The reaction is carried out in an inert solvent such as tetrahydrofuran or diethylether and may be carried out at atmospheric pressure, super atmospheric pressures or sub atmospheric pressures. The preferred mole ratio of ketone having the structure:

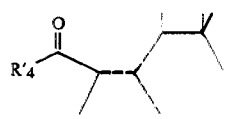

to organometallic compound, that is, alkyl lithium or alkyl magnesium halide is preferably 1:1 and if any material is used in excess, it is the ketone having the structure:

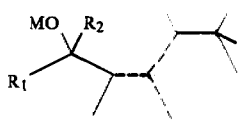

The hydrolysis of the organometallic compound thus formed, having the structure:

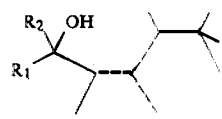

is carried out in dilute aqueous mineral acid such as aqueous sulfuric acid at concentrations of 0.05 molar up to about 1 motemperature of hydrolysis may vary from 0° C. up to about 50° C. with ambient temperatures being most convenient and preferred.

The reaction of the phosphorous pentasulfide with the alcohol having the structure:

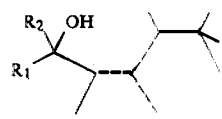

may be carried out at temperatures of from 0° C. up to 50° C., again with ambient temperatures being preferred. This reaction also takes place in the presence of solvent which is inert to the reaction ingredients, such as benzene, toluene or xylene.

The reaction to form the ethers, esters, thio ethers and thio esters by reacting the corresponding alcohol having the structure:

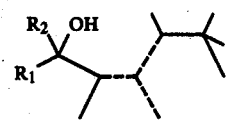

or the corresponding thiol having the structure:

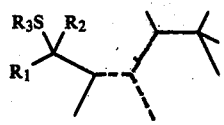

wherein $R_3$ is hydrogen may be carried out with standard etherifying or esterification reagents such as acetyl chloride, acetyl bromide, n-propenyl chloride, n-propenyl bromide, acetic anhydride, acetic-propionic anhydride, and n-butyric anhydride in the presence of an acid catalyst such as sulfuric acid (in the case of the esterification) and methyl iodide, ethyl iodide, and propyl iodide (in the case of the etherification) at temperatures of between 0° C. and 50° C. also in the presence of a solvent. In producing the ethers, it is preferable to first react the alcohol or thiol with sodium hydride thereby forming the sodium salt and then reacting the resulting sodium salt with methyl iodide, ethyl iodide or the like via a "Williamson" synthesis. In the alternative, the ethers may be formed by reaction with alcohol dialkyl sulfates such as dimethyl sulfate or diethyl sulfate.

Examples of branched chain unsaturated tertiary alcohols and their perfumery properties according to our invention are as follows:

TABLE I

| Structure | Organoleptic Properties (in Perfumery and in Perfumed Articles) |
|---|---|
| 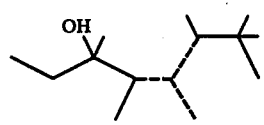<br>Mixture prepared according to Example IX supra wherein in each of the molecules of the mixture one of the dashed lines represents a carbon-carbon double bond and each of the other of the dashed lines represent carbon-carbon single bonds (bulked distillation fractions 2–7). | An amber, woody, camphoraceous aroma with patchouli topnotes. |
| OH (structure)<br>Prepared according to Example X, a mixture wherein in each of the molecules of the mixture one of the dashed lines represents a carbon-carbon double bond and each of the other of the dashed lines represent carbon-carbon single bonds (bulked distillation fractions 2–6). | An ambery, woody, fruity aroma. |

TABLE I-continued

| Structure | Organoleptic Properties (in Perfumery and in Perfumed Articles) |
|---|---|
| OH (structure)<br>A mixture produced according to Example XI wherein in each of the molecules of the mixture one of the dashed lines is a carbon-carbon double bond and each of the other of the dashed lines represent carbon-carbon single bonds (bulked distillation fractions 2–6). | An orris-like aroma. |
| OH (structure)<br>A mixture produced according to Example XII wherein in each of the molecules of the mixture one of the dashed lines is a carbon-carbon double bond and each of the other of the dashed lines represent carbon-carbon single bonds (bulked distillation fractions 4–8). | A floral, woody aroma. |

The individual branched chain tertiary alcohols, ethers, esters, thiol, thio ethers and thio esters of our invention can be obtained in purer form or in substantially pure form by conventional purification techniques. Thus, the products can be purified and/or acylated by distillation, extraction, crystallization, preparative chromatographic techniques and the like. It has been found desirable to purity the branched chain unsaturated tertiary alcohols, ethers, esters, thiols, thio ethers and thio esters of our invention by fractional distillation under vacuum.

It will be appreciated from the present disclosure that the branched chain tertiary alcohols, ethers, esters, thiol, thiol ethers and thio esters and mixtures thereof according to the present invention can be used to alter, vary, fortify, modify, enhance or otherwise improve the flavor of a wide variety of materials which are ingested, consumed or otherwise organoleptically sensed.

The term "alter" in its various forms will be understood herein to mean the supplying or imparting of a flavor character or note to an otherwise bland, relatively tasteless substance, or augmenting an existing flavor characteristic where the natural flavor is deficient in some regard or supplementing the existing flavor impression to modify the organoleptic character.

Such compounds are accordingly useful in flavoring compositions. A flavoring composition is taken to mean one which contributes a part of the overall flavor impression by supplementing or fortifying a natural or artificial flavor in a material or one which supplies substantially all the flavor and/or aroma character to a consumable article.

The term "enhance" is intended herein to mean the intensification of a particular aroma or taste nuance without changing the quality or nature of said nuance and without adding an additional aroma or taste nuance to the consumable material, the organoleptic properties of which are enhanced.

The term "foodstuff" as used herein includes both solid and liquid ingestible materials for man or animals, which materials usually do, but need not, have nutritional value. Thus, foodstuffs includes meats, gravies, soups, convenience foods, malt, alcoholic and other beverages, milk and dairy products, seafoods including fish, crustaceans, mollusks, and the like, candies, vegetables, cereals, soft drinks, snacks, dog and cat food, other veterinary products, and the like.

The branched chain unsaturated tertiary alcohols, ethers, esters, thiols, thio esters and thio ethers of our invention are useful tobacco flavorants and flavor enhancers.

The term "tobacco" will be understood herein to mean natural products such as, for example, burley, Turkish tobacco, Maryland tobacco, flue-cured tobacco and the like including tobacco-like or tobacco-based products such as reconstituted or homogenized leaf and the like, as well as tobacco substitutes intended to replace natural tobacco, such as lettuce and cabbage leaves and the like. The tobaccos and tobacco products in which the branched chain unsaturated tertiary alcohols, ethers, esters, tiols, thio esters and thio ethers of our invention are useful include those designed or used for smoking such as in cigarette, cigar and pipe tobacco, as well as products such as snuff, chewing tobacco and the like.

When the branched chain unsaturated tertiary alcohols, ethers, esters, thiols, thio esters and thio ethers of our invention are used in a flavoring composition, they can be combined with conventional flavoring materials or adjuvants. Such co-ingredients or flavoring adjuvants are well known in the art for such use and have been extensively described in the literature. Apart from the requirement that any such adjuvant material be ingestibly acceptable, and thus non-toxic or otherwise non-deleterious, conventional materials can be used and broadly include other flavor materials, vehicles, stabilizers, thickeners, surface active agents, conditioners, and flavor intensifiers.

Such conventional flavoring materials include saturated fatty acids, unsaturated fatty acids and amino acids; alcohols, including primary and secondary alcohols; esters; carbonyl compounds including ketones and aldehydes; lactones; other cyclic organic materials including benzene derivatives, alicyclic compounds, heterocyclics such as furans, pyrazines and the like; sulfur-containing materials including thiols, sulfides, disulfides and the like; proteins, lipids, carbohydrates; so-called flavor potentiators such as monosodium glutamate, guanylates and inosinates; natural flavoring materials such as cocoa, vanilla and caramel; essential oils and extracts such as anise oil; clove oil; and the like; and artificial flavoring materials such as vanillin; and the like.

Specific flavor adjuvants are as follows:
Ethyl-2-methyl butyrate;
Vanillin;
Butyl valerate;
2,3-Diethyl pyrazine;
Methyl cyclopentenolone;
Benzaldehyde;
Valerian Oil Indian; and
Propylene glycol.

The branched chain unsaturated tertiary alcohols, ethers, esters, thiols, thio esters and thio ethers of our invention can be used to contribute warm, patchouli-like, earthy, woody and camphoraceous aromas. As olfactory agents the branched chain unsaturated tertiary alcohols, ethers, esters, thiols, thio esters and thio ethers of this invention can be formulated into or used as components of a "perfume composition."

The term "perfume composition" is used herein to mean a mixture of organic compounds, including, for example, alcohols, aldehydes, ketones, nitriles, esters, and frequently hydrocarbons which are admixed so that the combined odors of the individual components produce a pleasant or desired fragrance. Such perfume compositions usually contain: (a) the main note of the "bouquet" or foundation-stone of the composition; (b) modifiers which round off and accompany the main note; (c) fixatives which include odorous substances which lend a particular note to the perfume throughout all stages of evaporation, and substances which retard evaporation; and (d) topnotes which are usually low-boiling fresh-smelling materials.

In perfume compositions, the individual component will contribute its particular olfactory characteristics but the overall effect of the perfume composition will be the sum of the effect of each ingredient. Thus, the individual compounds of this invention, or mixtures thereof, can be used to alter the aroma characteristics of a perfume composition, for example, by highlighting or moderating the olfactory reaction contributed by another ingredient in the composition.

The amount of branched chain unsaturated tertiary alcohols, ethers, esters, thiols, thio esters and thio ethers of this invention which will be effective in perfume compositions depends on many factors, including the other ingredients, their amounts and the effects which are desired. It has been found that perfume compositions containing as little as 0.05% and as much as 5% of the branched chain unsaturated tertiary alcohols, ethers, esters, thiols, thio ethers and thio esters of this invention can be used to impart, augment or enhance warm, intense, amber, woody, fruity, floral, orris-like and camphoraceous aroma profiles with patchouli undertones to soaps, cosmetics, solid or liquid anionic, cationic, nonionic and zwitterionic detergents and other products. The amount employed can range up to 50% of the fragrance and can be as low as 1% of the original fragrance and will depend on considerations of cost, nature of the end product, the effect desired in the finished product and the particular fragrance sought.

The branched chain unsaturated tertiary alcohols, ethers, esters, thiols, thio esters and thio ethers of this invention can be used alone or in a perfume composition as an olfactory component in detergents, and soaps, space odorants and deodorants, perfumes, colognes, toilet waters, bath salts, hair preparations such as lacquers, brilliantines, pomades, and shampoos, cosmetic preparations such as creams, deodorants, hand lotions and sun screens, powders such as talcs, dusting powders, face powder, and the like. When used in an olfactory component of a perfumed article, as little as 0.05% of one or more of the branched chain unsaturated tertiary alcohols, ethers, esters, thiols, thio esters and thio ethers will suffice to impart warm patchouli aroma with earthy, woody and camphoraceous notes. Generally no more than 5.0% is required.

In addition, the perfume composition can contain a vehicle or carrier for the branched chain unsaturated tertiary alcohols, ethers, esters, thiols, thio esters and thio ethers alone or with other ingredients. The vehicle can be a liquid such as an alcohol such as ethanol, a glycol such as propylene glycol, or the like. The carrier can be an absorbent solid such as a gum or components for encapsulating the composition.

The following examples A-XIII are given to illustrate techniques for producing the precursors for the compounds of our invention as it is presently preferred to practice it. Examples IX and onwards are given to illustrate embodiments of our invention as it is presently preferred to practice it. It will be understood that these examples are illustrative and the invention is not to be considered restricted thereto except as indicated in the appended claims.

EXAMPLE A

Preparation of Di-isoamylene Derivatives

Reaction:

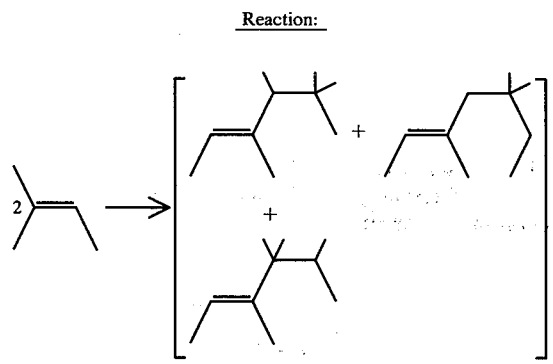

(wherein in each of the molecules indicated, one of the dashed lines is a carbon-carbon double bond and the other of the dashed lines are carbon-carbon single bonds).

Di-isoamylene is prepared according to one of the procedures set forth in the following references:
- i—Murphy & Lane, Ind. Eng. Chem., Prod. Res. Dev., Vol. 14, No. 3, 1975 p. 167 (Title: Oligomerization of 2-Methyl-2-Butene in Sulfuric and Sulfuric-Phosphoric Acid Mixtures).
- ii—Whitmore & Mosher, Vol. 68, J. Am. Chem. Soc., February, 1946, p. 281 (Title: The Depolymerization of 3,4,5,5-Tetramethyl-2-hexene and 3,5,5-Trimethyl-2-heptene in Relation to the Dimerization of Isoamylenes)
- iii—Whitmore & Stahly, Vol. 67, J. Am. Chem. Soc., December, 1945, p. 2158 (Title: The Polymerization of Olefins. VIII The Depolymerization of Olefins in Relation to Intramolecular Rearrangements. II)
- iv—U.S. Pat. No. 3,627,700, issued on Dec. 14, 1971, (Zuech)
- v—U.S. Pat. No. 3,538,181, issued on Nov. 3, 1970, (Banks)
- vi—U.S. Pat. No. 3,461,184, issued on Aug. 12, 1969 (Hay, et al)
- vii—Gurwitsch, Chemische Berichte, 1912, Vol. 2, p. 796 (Production of Di-isoamylene From Isoamylene Using Mercury Acetate Catalyst)

As an illustration, and not by way of limitation, the following example sets forth the preparation of diisoamylenes useful in producing the unsaturated branched-chain ketones which are useful in producing the fragrances, foodstuff flavor formulations, other flavor formulations and aromatized tobaccos of our invention.

EXAMPLE A-1

Over a period of ten hours, 2-methyl-2-butene is pumped through a 5'×⅝ (0.625 inch) tube packed with 15.0 g of polystyrene sulfonic acid catalyst, at a temperature of 100° C. and at a pressure of 400 psig.

The resulting material was distilled in a fractionation column in order to separate the diisoamylene from the higher molecular weight polymers which are formed during the reaction as by products. This material distills at 36°-40° C. vapor temperature; 74°-94° C. liquid temperature and 4-5 mm/Hg pressure. This material will be used in the syntheses in the following examples.

FIG. AA represents the GLC profile for the reaction product of Example A using a 70% sulfuric acid catalyst at 35%C.

FIG. AB represents the GLC profile for the reaction product of Example A using an Amberlyst ® 15 acidic ion exchange resin catalyst at a temperature of 150° C.

FIG. AC represents the GLC profile for the reaction product of Example A, using an Amberlyst ® 15 catalyst at 100° C.

FIG. AD represents the GLC profile for the reaction product of Example A, using a sulfuric acid catalyst and an alpha-methylstyrene diluent at 35° C. according to the conditions of United Kingdom Patent Specification No. 796,130 (crude reaction product).

FIG. AE represents the GLC profile for the reaction product of Example I, using a sulfuric acid catalyst, at 35° C. and an alpha-methyl styrene diluent according to the conditions of United Kingdom Patent Specification No. 796,130 (distilled reaction product). Distillation range: 36°-40° C. vapor temperature; 74°-94° C. liquid temperature and 4-5 mm/Hg pressure.

FIG. BA represents the NMR spectrum for Peak 1 of the GLC profile of FIG. AE.

FIG. BB represents the infra-red spectrum for Peak 1 of the GLC profile of FIG. AE.

FIG. CA represents the NMR spectrum for Peak 2 of the GLC profile of FIG. AE.

FIG. CB represents the infra-red spectrum for Peak 2 of the GLC profile of FIG. AE.

FIG. D represents the NMR spectrum for Peak 2 of the GLC profile of FIG. AB.

EXAMPLE I

Preparation of Acetyl Derivative of Diisoamylene

Reaction:

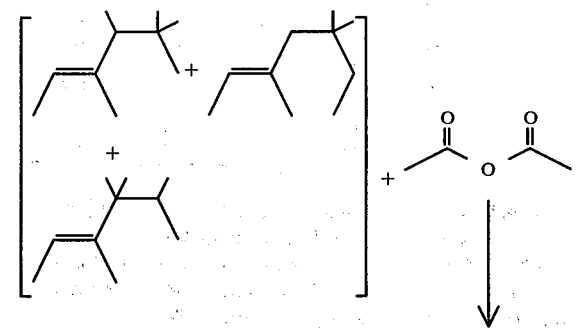

-continued
Reaction:

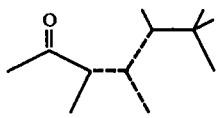

wherein in each of the structures containing dashed lines, these structures represent mixtures of molecules wherein in each of the molecules, one of the dashed lines respresents a carbon-carbon double bond and each of the other of the dashed lines respresent carbon-carbon single bonds.

Into a 2-liter reaction flask equipped with stirrer, thermometer, reflex condenser and heating mantle, is placed 1000 g of acetic anhydride and 80 g of boron trifluoride diethyl etherate. The resulting mixture is heated to 80° C. and, over a period of 40 minutes, 690 g of diisoamylene prepared according to the illustration in Example A-1, supra is added. The reaction mass is maintained at 82°–85° C. for a period of 5.5 hours, whereupon it is cooled to room temperature. The reaction mass is then added to one liter of water and the resulting mixture is stirrer thereby yielding two phases; an organic phase and an aqueous phase. The organic phase is separated from the aqueous phase and neutralized with two liters of 12.5% sodium hydroxide followed by one liter of saturated sodium chloride solution. The resulting organic phase is then dried over anhydrous sodium sulfate and distilled in a one plate distillation column, yielding the following fractions:

| Fraction No. | Vapor Temp. (°C.) | Liquid Temp. (°C.) | mm/Hg Pressure | Weight of Fraction (g.) |
|---|---|---|---|---|
| 1 | 33/68 | 62/77 | 8/8 | 161 |
| 2 | 69 | 79 | 4 | 100 |
| 3 | 72 | 86 | 3.0 | 191 |
| 4 | 88 | 134 | 3.0 | 189 |

The resulting material is then distilled on a multi-plate fractionation column, yielding the following fractions at the following reflux ratios:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 30/65 | 62/83 | 5/5 | 9:1 | 30.8 |
| 2 | 68 | 84 | 5 | 9:1 | 52.8 |
| 3 | 68 | 85 | 5 | 9:1 | 34 |
| 4 | 69 | 87 | 5 | 9:1 | 43 |
| 5 | 69 | 87 | 5 | 9:1 | 34 |
| 6 | 71 | 88 | 4 | 4:1 | 41 |
| 7 | 70 | 88 | 5 | 4:1 | 36.5 |
| 8 | 71 | 91 | 5 | 4:1 | 42 |
| 9 | 73 | 95 | 3 | 4:1 | 42.5 |
| 10 | 80 | 106 | 3 | 4:1 | 39 |
| 11 | 80 | 142 | 3 | 4:1 | 50.8 |
| 12 | 80 | 220 | 3 | 4:1 | 24 |

Fractions 5–9 of the above distillation are bulked and used as reactants in the following examples.

GLC, NMR, IR and mass spectral analyses yield the information that the resulting material is a mixture of cis and trans isomers having a generic structure:

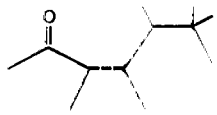

wherein in each of the molecules, one of the dashed lines is a carbon-carbon double bond and the other of the dashed lines is a carbon-carbon single bond and, primarily, this mixture contains the molecular species (cis and trans isomers) as follows:

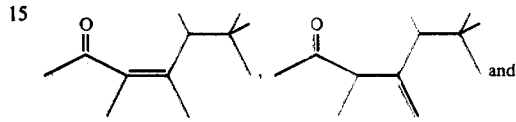

FIG. 1 sets forth the GLC profile for the reaction product of Example I, containing compounds defined according to the structure:

wherein in each molecule of the mixture, one of the dashed lines is a carbon-carbon double bond and the other of the dashed lines are carbon-carbon single bonds.

FIG. 2A represents the infra-red spectrum of Peak 3 of the GLC profile of FIG. 1.

FIG. 2B represents the infra-red spectrum of Peak 4 of the GLC profile of FIG. 1.

FIG. 2C represents the infra-red spectrum for Peak 5 of the GLC profile of FIG. 1.

FIG. 2D represents the infra-red spectrum for Peak 7 of the GLC profile of FIG. 1.

FIG. 2E represents the infra-red spectrum for Peak 7 of the GLC profile of FIG. 1.

FIG. 2F represents the infra-red spectrum for Peak 8 of the GLC profile of FIG. 1.

FIG. 2G represents the infra-red spectrum for Peak 9 of the GLC profile of FIG. 1. produced according to Example I.

FIG. 2K represents the NMR spectrum for the compound having the structure:

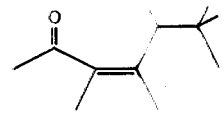

produced according to Example I.

FIG. 2L represents the NMR spectrum for the compound containing the structure:

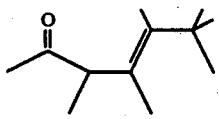

produced according to Example 1.

EXAMPLE II

Preparation of Propionyl Derivative of Diisoamylenes

Reaction:

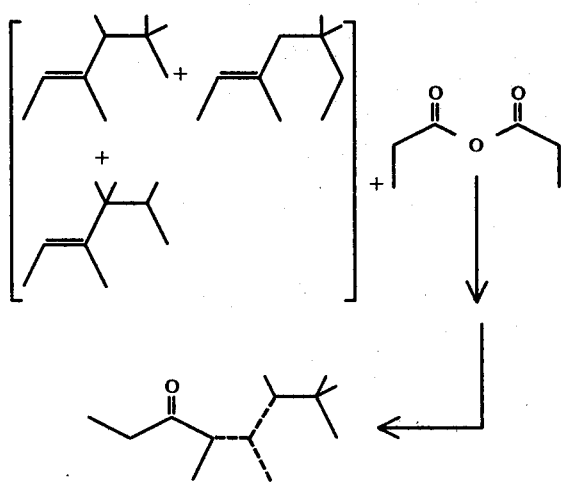

wherein in each of the structures containing dashed lines, these structures represent mixtures of molecules wherein in each of the molecules, one of the dashed lines represents a carbon-carbon double bond and each of the other of the dashed lines represent carbon-carbon single bonds.

Into a 5-liter reaction flask equipped with reflux condenser, addition funnel, thermometer, "Thermowatch," heating mantle and nitrogen purge accessory is placed 1000 g (7.45 moles) of propionic anhydride, 94% and 91.4 ml (0.745 moles) of boron trifluoride etherate. The resulting mixture is heated to 65° C. Over a twenty-five minute period, 1,501 ml (7.45 moles) of the diisoamylene prepared according to the illustration of Example A-1 is added while maintaining the reaction mass at 65°-70° C. The reaction mass is then stirred for a period of thirty minutes at 65° C. whereupon it is cooled and poured into a 3 liter separatory funnel. 75 ml water is then added, followed by 75 ml 50% aqueous sodium hydroxide and another 25 ml water. The reaction mass is then poured into a 4 liter beaker and cooled to room temperature using a dry ice-isopropyl alcohol bath. The reaction mass is then added to a 5-liter separatory funnel and the lower aqueous layer is removed. The upper organic phase is washed with 500 cc of saturated sodium chloride. The organic phase is then washed with 500 cc 5% sodium hydroxide followed by 500 cc saturated sodium chloride, followed by 500 cc of 5% sodium hydroxide. The pH of the oil is now in a range of 6-7. The oil is then again washed with 500 cc saturated sodium chloride.

The aqueous phase is extracted with 400 ml diethyl ether. The resulting material is then distilled on a two inch splash column yielding the following fractions:

| Fraction No. | Vapor Temp. (°C.) | Liquid Temp. (°C.) | mm/Hg Pressure | Weight of Fraction (g.) |
|---|---|---|---|---|
| 1 | 25/75 | 60/85 | 50/50 | 144 |
| 2 | 74 | 87 | 38 | 184 |
| 3 | 34 | 40 | 4 | 186 |
| 4 | 55 | 78 | 3 | 212 |
| 5 | 87 | 94 | 3 | 181 |
| 6 | 95 | 114 | 3 | 210 |
| 7 | 170 | 155 | 3 | 80 |
| 8 | 160 | 225 | 3 | 42 |

Fractions 5, 6 and 7 are then bulked for redistillation and the bulked material is distilled on a one-inch Goodloe Silver Mirror Column, yielding the following fractions:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 17/60 | 81/90 | 3/1.4 | 1:4 | 42 |
| 2 | 58 | 89 | 1.0 | 4:1 | 48 |
| 3 | 63 | 93 | 1.0 | 4:1 | 37 |
| 4 | 68 | 94 | 1.0 | 4:1 | 48 |
| 5 | 70 | 94 | 1.0 | 4:1 | 43 |
| 6 | 72 | 95 | 1.8 | 2:1 | 39 |
| 7 | 72 | 94 | 1.7 | 2:1 | 87 |
| 8 | 74 | 108 | 1.6 | 2:1 | 48 |
| 9 | 82 | 135 | 1.6 | 2:1 | 48 |
| 10 | 110 | 220 | 1.0 | 2:1 | 37 |

Fractions 2-10 are then bulked and redistilled on a 1-foot Goodloe Silver Mirror Column, again yielding the following fractions:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 52/58 | 83/85 | 1.4/1.2 | 4:1 | 46 |
| 2 | 59 | 86 | 1.1 | 4:1 | 50 |
| 3 | 61 | 89 | 1.1 | 4:1 | 53 |
| 4 | 61 | 89 | .9 | 4:1 | 57 |
| 5 | 61 | 91 | .8 | 4:1 | 44 |
| 6 | 61 | 91 | .8 | 4:1 | 41 |
| 7 | 65 | 101 | .8 | 4:1 | 42 |
| 8 | 68 | 115 | .8 | 4:1 | 49 |
| 9 | 74 | 135 | .8 | 4:1 | 17 |
| 10 | 88 | 230 | .8 | 4:1 | 17 |

Fractions 3-7 of the foregoing distillation are bulked and utilized as a reactant for the following examples.

The resulting material is analyzed using GLC, IR, mass spectral and NMR analyses yielding information that the resulting material is a mixture of compounds defined according to the generic structure:

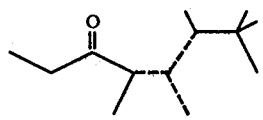

wherein in each molecule of the mixture, one of the dashed lines is a carbon-carbon double bond and each of the other of the dashed lines are carbon-carbon single bonds.

FIG. 3 represents the GLC profile for the reaction product of Example II containing a mixture of compounds, each of which is defined according to the generic structure:

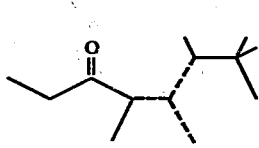

wherein in each molecule one of the dashed lines is a carbon-carbon double bond and each of the other of the dashed lines are carbon-carbon single bonds.

FIG. 4 represents the infra-red spectrum for the product produced according to Example II containing the compounds having the structures:

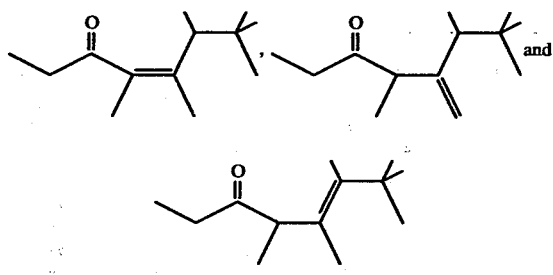

FIG. 5 represents the mass spectrum for the reaction product of Example II, containing the compounds having the structures:

EXAMPLE III

Preparation of n-Butyryl Derivative of Diisoamylene

Reaction:

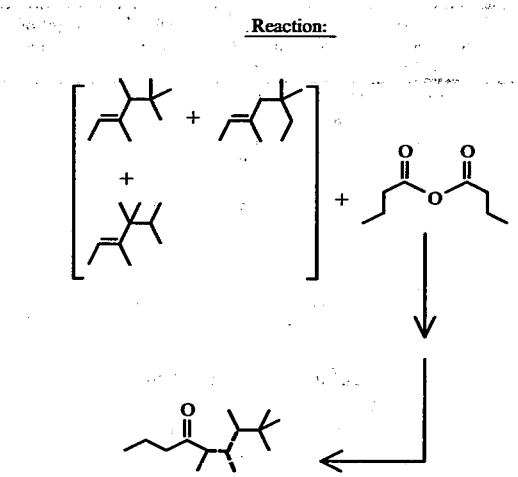

wherein in each of the structures containing dashed lines, these structures represent mixtures of molecules wherein in each of the molecules, one of the dashed lines represents a carbon-carbon double bond and each of the other of the dashed lines represent carbon-carbon single bonds.

Into a 5-liter reaction flask equipped with electric stirrer, heating mantle, thermometer, 24/40 "Y" joint, addition funnel and reflux condenser is added 960 g of n-butyric anhydride, followed by 105 ml boron trifluoride. The resulting mixture is heated to 65° C. and a Thermowatch is attached (reaction must not exceed a pot temperature of 65° C.).

The reaction mass is heated to 65° C. and dropwise addition of 1,725 ml of diisoamylene, prepared according to the illustration of Example A-1 is added over a period of 3.5 hours while maintaining the reaction mass at a temperature of 65° C.

At the end of the addition, the reaction mass is cooled to 38° C. and then transferred to a 5-liter separatory funnel. 75 ml of 50% aqueous sodium hydroxide and 100 ml water are then added to the reaction mass. The reaction mass now exists in two phases; an aqueous phase and an organic phase. The organic phase is washed with one liter of saturated sodium chloride solution thereby creating a pH of 4–5. The reaction mass is then washed with 1-liter of 12.5% sodium hydroxide, stirred for fifteen minutes, and then separated. The resulting organic phase is then dried over anhydrous magnesium sulfate and distilled on a 1-inch Stone column yielding the following fractions:

| Fraction No. | Vapor Temp. (°C.) | Liquid Temp. (°C.) | mm/Hg Pressure |
|---|---|---|---|
| 1 | 40/46 | 63/65 | 30/20 |
| 2 | 66 | 77 | 40 |
| 3 | 66 | 77 | 35 |
| 4 | 66 | 87 | 33 |
| 5 | 69 | 90 | 20 |
| 6 | 64 | 100 | 5 |
| 7 | 95 | 110 | 2 |
| 8 | 97 | 110 | 2 |
| 9 | 125 | 160 | 2 |

The resulting fractions 7, 8 and 9 are bulked and redistilled on a 2 foot stainless steel column yielding the following fractions:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 47/74 | | 1.8 | 4:1 | 53 |
| 2 | 74 | 105 | 1.4 | 4:1 | 15 |
| 3 | 74 | 107 | 1.4 | 4:1 | 96 |
| 4 | 74 | 107 | 1.4 | 4:1 | 39 |
| 5 | 70 | 105 | 1.0 | 4:1 | 16 |
| 6 | 75 | 110 | 1.0 | 4:1 | 44 |
| 7 | 84 | 165 | 1.0 | 4:1 | 16 |
| 8 | 80 | 220 | 1.0 | 4:1 | 12 |

Fractions 3 and 4 of the foregoing distillation are bulked for use in subsequent examples.

FIG. 6 represents the GLC profile for the reaction product of Example III containing compounds defined according to the generic structure:

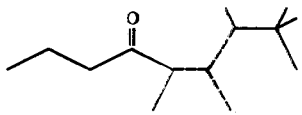

wherein in each of the molecule of the mixture, one of the dashed lines represents a carbon-carbon double bond and the other of the dashed lines represents carbon-carbon single bonds.

FIG. 7 represents the infra-red spectrum for the reaction product of Example III containing the compounds having the structures:

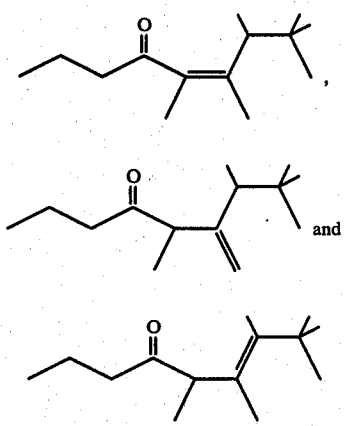

FIG. 8 represents the mass spectrum for the reaction product of Example III containing the compound having the structures:

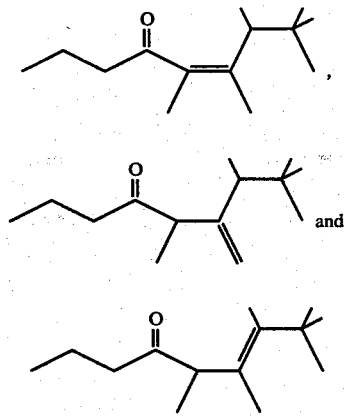

EXAMPLE IV

Preparation of Isobutyryl Derivative of Diisoamylene

Reaction:

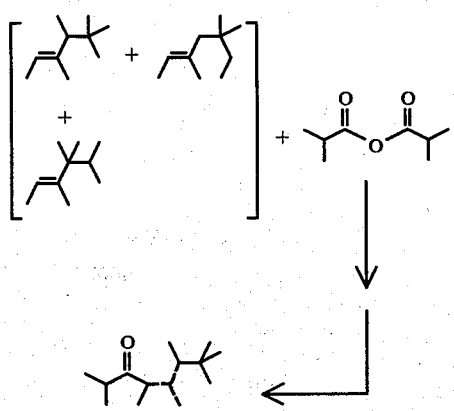

wherein in each of the structures containing dashed lines, these structures represent mixtures of molecules wherein in each of the molecules, one of the dashed lines represents a carbon-carbon double bond and each of the other of the dashed lines represent carbon-carbon single bonds.

Into a 5-liter reaction flask, equipped with reflux condenser, addition funnel, thermometer, Thermowatch, heating mantle and nitrogen purge accessory is placed 1361 g (8.6 moles) of isobutyric anhydride. 105 ml (0.86 moles) of boron trifluoride etherate is then added to the isobutyric anhydride. The resulting mixture is then heated to 65° C. Over a period of 4 hours, 1725 g (8.6 moles) of diisoamylene prepared according to the illustration of Example A-1 is added to the reaction mass, while maintaining the reaction mass at a temperature of 83°–85° C.

The reaction mass is then cooled to room temperature and is added to a 5-liter separatory funnel. 75 ml of 50% sodium hydroxide (aqueous) and 100 ml water is then added to the reaction mass thus yielding two phases, an aqueous phase and an organic phase. The lower aqueous phase is removed and the organic phase is washed as follows:

A—1 liter saturated sodium chloride
B—1 liter 5% aqueous sodium hydroxide
C—1 liter saturated sodium chloride
D—1 liter 12.5% sodium hydroxide
E—1 liter 12.5% sodium hydroxide The reaction mass is then distilled on a two inch splash column packed with stones yielding the following fractions:

| Fraction No. | Vapor Temp. (°C.) | Liquid Temp. (°C.) | mm/Hg Pressure | Weight of Fraction (g.) |
|---|---|---|---|---|
| 1 | 29/54 | 54/68 | 29/24 | Starting Material |
| 2 | 51 | 68 | 14 | " |
| 3 | 90 | 68 | 11 | " |
| 4 | 64 | 98 | 11 | " |
| 5 | 92/94 | 102/108 | 7/5 | 378 |
| 6 | 135 | 165 | 5 | 257 |

Fractions 5 and 6 of the resulting distillate are then bulked and redistilled yielding the following fractions:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 15/45 | 88/92 | 3/2.5 | 4:1 | 21 |
| 2 | 60 | 99 | 2.4 | 4:1 | 13 |
| 3 | 67 | 98 | 2.4 | 4:1 | 35 |
| 4 | 69 | 97 | 2.2 | 4:1 | 49 |
| 5 | 70 | 99 | 2.2 | 4:1 | 59 |
| 6 | 70 | 101 | 2.2 | 4:1 | 50 |
| 7 | 70 | 101 | 2.0 | 4:1 | 37 |
| 8 | 84 | 112 | 1.7 | 4:1 | 33 |
| 9 | 84 | 112 | 1.7 | 4:1 | 63 |
| 10 | 78 | 119 | 1.8 | 4:1 | 37 |
| 11 | 84 | 122 | 1.7 | 4:1 | 51 |
| 12 | 92 | 121 | 1.7 | 4:1 | 43 |
| 13 | 101 | 156 | 1.6 | 4:1 | 27 |
| 14 | 121 | 178 | 1.6 | 4:1 | 85 |
| 15 | 110 | 220 | 1.6 | 4:1 | 33 |

Fractions 3–9 of this distillation are then rebulked and redistilled on a 12 inch Goodloe Silver Mirror column yielding the following fractions:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 47/60 | 84/92 | 1.6/1.2 | 4:1 | |

-continued

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 2 | 67 | 93 | 1.2 | 4:1 | 50 |
| 3 | 67 | 94 | 1.2 | 4:1 | 50 |
| 4 | 67 | 95 | 1.2 | 4:1 | 52 |
| 5 | 67 | 95 | 1.2 | 4:1 | 50 |
| 6 | 67 | 98 | 1.2 | 4:1 | 57 |
| 7 | 67 | 101 | 1.2 | 4:1 | 57 |
| 8 | 72 | 212 | 1.2 | 4:1 | 42 |

Fractions 4–7 of the foregoing distillation are bulked for subsequent reaction as described in subsequent examples.

The resulting reaction product is analyzed by means of GLC, NMR, IR and mass spectral analyses and this confirms that the reaction product is a mixture of compounds defined according to the generic structure:

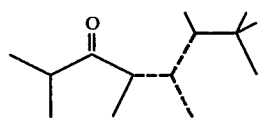

wherein in each of the molecules, one of the dashed lines is a carbon-carbon double bond and the other two of the dashed lines represent carbon-carbon single bonds. The major components of this mixture are compounds having the structures:

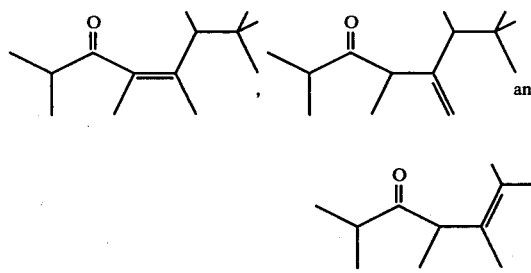

FIG. 9 represents the GLC profile for the reaction product of Example IV, containing a mixture of compounds, each of which is defined according to the generic structure:

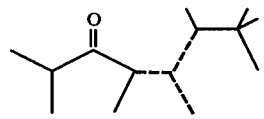

wherein in each of the molecules, one of the dashed lines represents a carbon-carbon double bond and each of the other of the dashed lines represent carbon-carbon single bonds.

FIG. 10 represents the infra-red spectrum for the reaction product of Example IV containing the compounds having the structures:

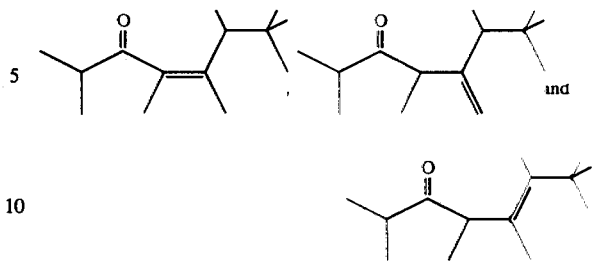

FIG. 11 represents the mass spectrum for the reaction product of Example IV containing the compounds having the structures:

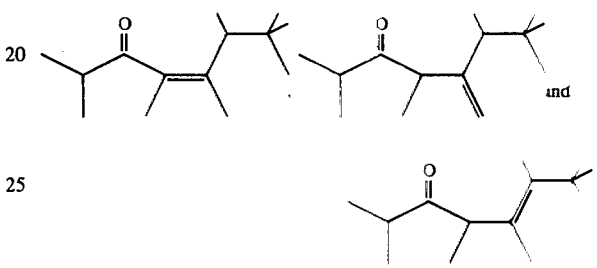

EXAMPLE V

Preparation of Acetyl Derivative of Diisoamylene

Reaction:

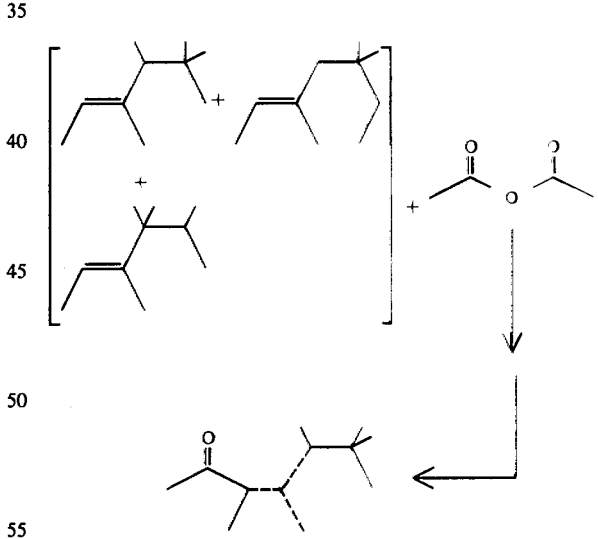

EXAMPLE VA

Into a 5-liter reaction flask equipped with electric stirrer, thermometer, addition funnel, 24/42 y-tube, condenser, heating mantle and nitrogen purge accessories are added 41 ml of 70% methane sulfonic acid followed by 30 g of phosphorus pentoxide. The resulting mixture exotherms to 60° C.

Over a period of 7 minutes, 235 ml acetic anhydride is added to the reaction mass while maintaining the same at a temperature of 65° C. Over a period of 30 minutes while maintaining the reaction temperature at 80° C., 516 ml of diisoamylene prepared according to the illustration of Example A-1 is added dropwise to the reaction mass. At the end of the addition of the diisoamylene, GLC analysis indicates 42% product.

The reaction mass is added to a 5 gallon open head separatory flask containing 1 liter of water.

The resulting mixture is washed with 1 liter of 12% sodium hydroxide followed by 1 liter of saturated sodium chloride solution. 100 ml toluene is added to help separation.

GLC, NMR, IR and mass spectral analyses yield the information that the resulting organic phase is a mixture of compounds defined according to the generic structure:

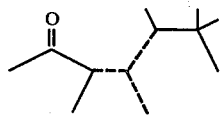

wherein in each of the molecules one of the dashed lines is a carbon-carbon double bond and the other two of the dashed lines represent carbon-carbon single bonds.

The resulting reaction product is then dried over anhydrous magnesium sulfate and distilled on a 3-inch stone column yielding the following fractions:

| Fraction No. | Vapor Temp. (°C.) | Liquid Temp. (°C.) | mm/Hg Pressure |
|---|---|---|---|
| 1 | 65/65 | 103/92 | 113/35 |
| 2 | 60 | 80 | 1 |
| 3 | 52 | 89 | 1 |
| 4 | 61 | 134 | 1 |
| 5 | 73 | 140 | 1 |

Fraction 2, 3 and 4 are bulked and utilized as reactants in the following examples.

FIG. 12 represents the GLC profile for the reaction product of Example VA containing structures defined according to the genus having the structure:

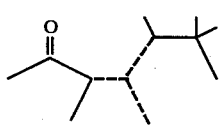

wherein in each of the molecules of the mixture, one of the dashed lines represents a carbon-carbon double bond and each of the other of the dashed lines represent carbon-carbon single bonds.

EXAMPLE VB

To a 500 ml reaction flask equipped with reflux condenser, addition funnel, thermometer, Thermowatch, heating mantle, cooling bath and nitrogen purge accessories, is added 406 ml of acetic anhydride and 30 ml boron trifluoride etherate. The reaction mass is heated to 60° C. and while maintaining the reaction mass at 60° over a period of 30 minutes, diisoamylene, prepared according to the illustration of Example A-1 is added. The resulting reaction mass is then heated, with stirring at 60° C. for a period of 12 hours. At the end of the 12 hour period, the reaction mass is distilled yielding the following fractions:

| Fraction No. | Vapor Temp. (°C.) | Liquid Temp. (°C.) | mm/Hg pressure | Weight of Fraction (g.) |
|---|---|---|---|---|
| 1 | 50/58 | 60/70 | 2.5 | 330 |
| 2 | 67 | 87 | 1.4 | 329 |
| 3 | 71 | 88 | 3.0 | 65 |
| 4 | 90 | 115 | 3.0 | 195 |

Fractions 2 and 3 are bulked for subsequent reaction.

The resulting mass, by GLC, IR, NMR and mass spectral analyses consist of compounds defined according to the generic structure:

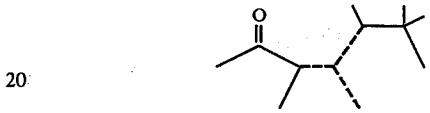

wherein in each of the molecules one of the dashed lines is a carbon-carbon double bond and the other two of the dashed lines represent carbon-carbon single bonds.

FIG. 13 sets forth the GLC profile for the reaction product of this Example VB.

EXAMPLE VI

Preparation of Propionyl Derivative of Diisoamylene

Reaction:

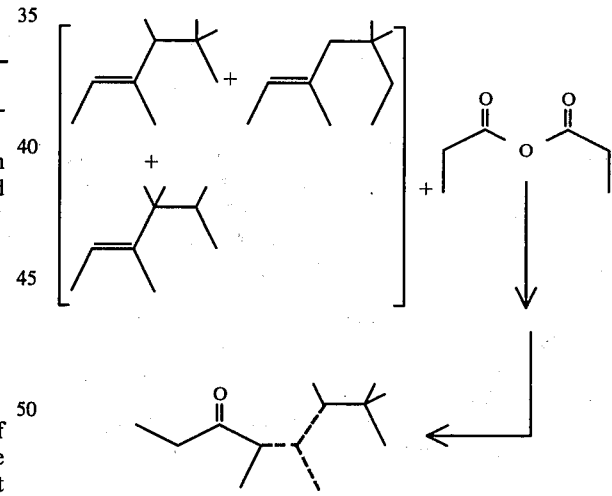

Into 5000 ml reaction flask equipped with reflux condenser, addition funnel, thermometer, Thermowatch, heating mantle, cooling bath and nitrogen purge accessory, is added 415 ml propionic anhydride, 11 g of methane sulfonic acid and 35 ml of boron trifluoride etherate. The reaction mass is heated to 60° C. and over a period of 30 minutes, 1850 ml of diisoamylene prepared according to the illustration of Example A-1 is added. The reaction mass is then stirred at 60° C. for a period of 12 hours. At the end of the 12 hour period, the reaction mass is distilled on a Goodloe fractionation column to yield a mixture of compounds having the generic structure:

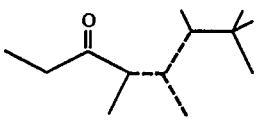

wherein in each of the molecules therein one of the dashed lines represents a carbon-carbon double bond and each of the other of the dashed lines represents a carbon-carbon single bond. The reaction structures are confirmed by GLC, NMR, IR and mass spectral analyses.

The product distills at a vapor temperature of 68°-70° C. and a pressure of 1.0 mm/Hg. This product is utilized for subsequent reaction in subsequent examples.

EXAMPLE VIIA

Preparation of Isobutyro Derivative of Diisoamylene

Reaction:

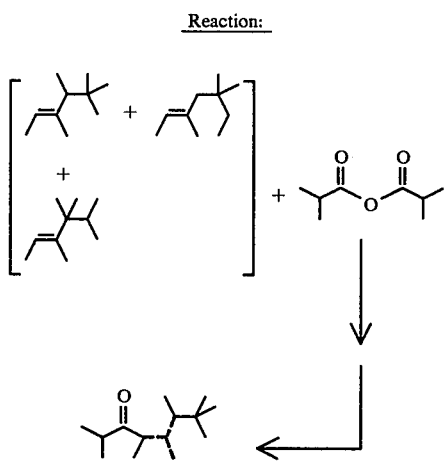

wherein in each of the structures containing dashed lines, these structures represent mixtures of molecules wherein in each of the molecules, one of the dashed lines represents a carbon-carbon double bond and each of the other of the dashed lines represents carbon-carbon single bonds.

Into a 5000 ml reaction flask equipped with reflux condenser, addition funnel, thermometer, Thermowatch, heating mantle, cooling bath and nitrogen gas purge accessory, is added 953 ml (6.0 moles) of isobutyric anhydride; 183 g of polyphosphoric acid and 135 ml 70% methane sulfonic acid. The reaction mass exotherms to 65° C.

Over a period of 20 minutes, while maintaining the reaction mass at 65° C. 1725 g (8.6 moles) of diisoamylene prepared according to the illustration of Example A-1 is added to the reaction mass. The reaction mass is then heated to 85° C. and maintained at that temperature for a period of 10 hours. At the end of the 10 hour period, the reaction mass is cooled and 100 g of sodium acetate and 1 liter of water are added thereto. The resulting mixture is added to a 5 liter separatory funnel and the organic layer is then washed as follows:

A—1 liter 12.5% sodium hydroxide
B—2 liter 12.5% sodium hydroxide
C—1 liter of saturated sodium chloride The reaction mass is then distilled on a 1 foot Goodloe column yielding the following fractions:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 35/50 | 88/93 | 1.8/.08 | 4:1 | 41 |
| 2 | 63 | 100 | 0.8 | 4:1 | 48 |
| 3 | 63 | 105 | 0.6 | 4:1 | 73 |
| 4 | 66 | 114 | 0.6 | 4:1 | 44 |
| 5 | 100 | 145 | 0.6 | 4:1 | 42 |
| 6 | 101 | 225 | 0.6 | 4:1 | 29 |

Fractions 3-5 are bulked and the bulking is utilized for subsequent reaction in subsequent examples.

GLC, NMR, IR and mass spectral analyses confirm the information that the resulting product is a mixture of compounds defined according to the generic structure:

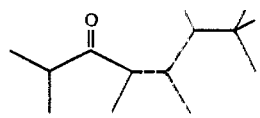

wherein in each molecule of the mixture, one of the dashed lines is a carbon-carbon double bond and the other two of the dashed lines represent carbon-carbon single bonds.

FIG. 14 sets forth the GLC profile for the reaction product of this Example VIIA. (Conditions: SF 96 column, six foot × ¼ inch; operated at 180° C. isothermal).

EXAMPLE VIIB

Into a 5000 ml reaction flask equipped with reflux condenser, addition funnel, thermometer, Thermowatch, heating mantle, cooling bath and nitrogen gas purge accessory, is added 953 g (6.0 moles) of isobutyric anhydride and 105 ml (0.86 moles) of boron trifluoride etherate. The reaction mass is heated to 65° C. and over a period of 30 minutes 1725 ml (8.6 moles) of diisoamylene prepared according to the illustration of Example A-1 is added. The reaction mass is then heated to 63°-65° C. and maintained with stirring at that temperature for a period of 12 hours.

The reaction mass is then cooled to room temperature and 82 g of sodium acetate are added. The reaction mass is then poured into a 5 liter separatory funnel and washed as follows:

A—1 liter water
B—1 liter 12.5% aqueous sodium hydroxide
C—1 liter 12.5% aqueous sodium hydroxide
D—1 liter 12.5% aqueous sodium hydroxide
E—1 liter saturated sodium chloride The organic layer is then dried over anhydrous sodium sulfate and distilled on a 12 inch Goodloe column yielding the following fractions:

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 1 | 55/67 | 85/92 | 2.4/1.5 | 4:1 | 50 |
| 2 | 72 | 95 | 1.5 | 4:1 | 72 |
| 3 | 73 | 98 | 1.5 | 4:1 | 83 |
| 4 | 75 | 104 | 1.4 | 4:1 | 69 |
| 5 | 80 | 112 | 1.4 | 4:1 | 69 |
| 6 | 80 | 112 | 1.4 | 4:1 | 12 |
| 7 | 108 | 140 | 1.4 | 2:3 | 69 |
| 8 | 116 | 180 | 1.4 | 2:3 | 61 |

-continued

| Fraction No. | Vapor Temp. (°C.) | Liquid Temp. (°C.) | mm/Hg Pressure | Reflux Ratio R/D | Weight of Fraction (g.) |
|---|---|---|---|---|---|
| 9 | 110 | 225 | 1.4 | 2:3 | 9 |

Fractions 4–7 are bulked and the resulting bulked product is utilized for subsequent reaction in subsequent examples.

GLC, NMR, IR and mass spectral analyses confirm that the resulting product is a mixture of compounds defined according to the generic structure:

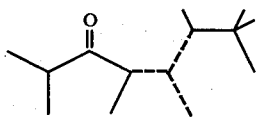

wherein in each of the molecules in the mixture one of the dashed lines represents a carbon-carbon double bond and the other of the dashed lines represent carbon-carbon single bonds.

EXAMPLE VIII

Preparation of n-Butyro Diisoamylene and Derivatives

Reaction:

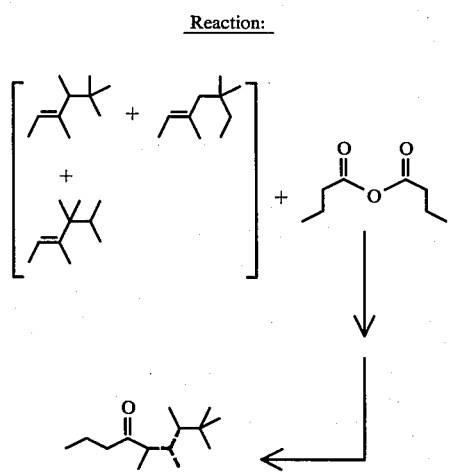

wherein in each of the structures containing dashed lines, these structures represent mixtures of molecules wherein in each of the molecules, one of the dashed lines represents a carbon-carbon double bond and each of the other of the dashed lines represent carbon-carbon single bonds.

Into a 5 liter reaction flask equipped with electric stirrer, thermometer, addition funnel "y" tube, condenser, heating mantle and nitrogen purge accessory are added 55 ml of 70% methane sulfonic acid and 30 g of phosphorous pentoxide. The reaction mass exotherms to 60° C. while maintaining the reaction mass at 65° C. over a period of 10 minutes, 400 ml n-butyric anhydride is added to the reaction mass. Over a period of 40 minutes while maintaining the reaction mass at 84° C., 400 ml of diisoamylene prepared according to the illustration of Example A-1 is added to the reaction mass. The reaction mass is stirred for a period of 4 hours at 84° C.

The reaction mass is then transferred to a 5 gallon open head separatory flask containing 2 liters water. The reaction mass is washed as follows:

A—1 liter 12% aqueous sodium hydroxide

B—1 liter saturated sodium chloride solution

The reaction mass is then distilled on a 12 inch Goodloe Silver Mirror column to yield a mixture of compounds defined according to the generic structure:

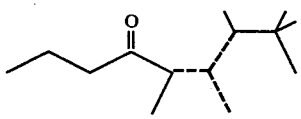

wherein in each of the molecules of the mixture, one of the dashed lines represents carbon-carbon double bond and the other of the dashed lines represent carbon-carbon single bonds. The foregoing is confirmed by GLC, NMR, IR and mass spectral analyses.

The resulting material distills at a vapor temperature of 70°–75° C. and a pressure of 1.0 mm/Hg. The resulting material is utilized for subsequent reaction in subsequent examples.

EXAMPLE IX

Hydrolysis Product of Reaction Product of Methyl Lithium and Acetyl Diisoamylene Reaction:

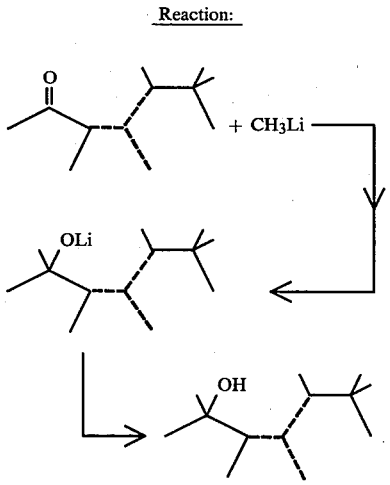

(wherein the reactant and product are mixtures and the mixtures contain molecules wherein one of the dashed lines represents a carbon-carbon double bond and each of the other of the dashed lines represent carbon-carbon single bonds).

Into a 2 liter reaction flask equipped with reflux condenser addition funnel, thermometer, cooling bath and nitrogen blanket provision apparatus, is placed 1 mole of methyl lithium and 1000 cc of anhydrous diethylether. Over a period of 30 minutes while maintaining the reaction mass at 18°–29° C., 142 grams (0.8 moles) of acetyl diisoamylene produced according to Example I is added dropwise. The reaction mass is then maintained at 29°–41° C. over a period of 8 hours.

To the reaction mass 300 ml water is added with exotherming. The resulting aqueous solution is poured into a 2 liter separatory funnel and the lower aqueous is removed. The organic phase is washed with 2 portions of 500 ml of aqueous sodium chloride. The solvent (diethylether) is then evaporated from the reaction mass and the reaction mass is distilled on a microdistillation apparatus yielding the following fractions:

| Fraction Number | Vapor Temp. °C. | Liquid Temp. °C. | Head Vac. mm. Hg | Reflux Ratio R/D | Weight of Fraction |
|---|---|---|---|---|---|
| 1 | 71/72 | 75/74 | 3/3 | RO | 19 |
| 2 | 71 | 75 | 3 | 50% | 17 |
| 3 | 74 | 78 | 3 | 50% | 24 |
| 4 | 74 | 78 | 3 | 50% | 7 |
| 5 | 75 | 78 | 3 | 50% | 16 |
| 6 | 74 | 78 | 3 | 50% | 21 |
| 7 | 75 | 78 | 3 | 50% | 19 |
| 8 | 83 | 89 | 2.8 | 50% | 25 |
| 9 | 155 | 195 | 3 | 50% | 9 |

Fractions 2-8 are bulked and utilized for their organoseptic properties in the utility examples, infra.

FIG. 15 represents the GLC profile for the reaction product of Example IX containing a mixture of compounds defined according to the structure:

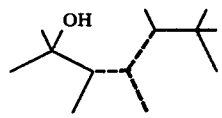

wherein in each of the molecules one of the dashed lines represents a carbon-carbon double bond and each of the other of the dashed lines represent carbon-carbon single bonds.

FIG. 16 is the NMR spectrum for the reaction product of Example IX containing a mixture of compounds having the structures defined according to the following structure:

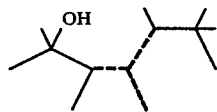

wherein in each of the molecules of the mixture one of the dashed lines represents a carbon-carbon double bond and each of the other of the dashed lines represent carbon-carbon single bonds.

FIG. 17 is the infra-red spectrum for the reaction product of Example IX containing the compounds defined according to the structure:

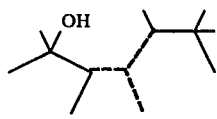

wherein in each of the molecules in the resulting mixture one of the dashed lines represents a carbon-carbon double bond and each of the other of the dashed lines represent carbon-carbon single bonds.

EXAMPLE X

Hydrolysis Product of Reaction Product of Propianyl Diisoamylene and Methyl Lithium Reaction:

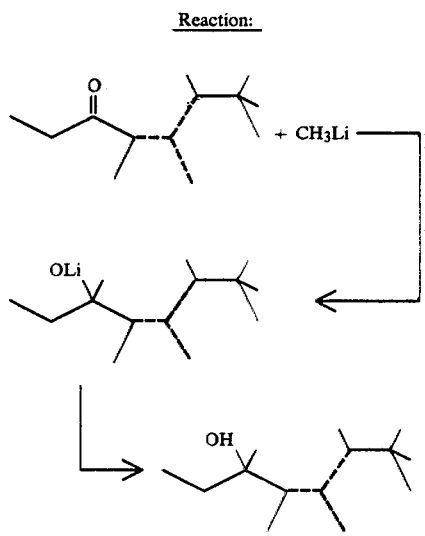

(wherein the reactant and product are mixtures and the mixtures contain molecules wherein one of the dashed lines represents a carbon-carbon double bond and each of the other of the dashed lines represent carbon-carbon single bonds).

Into a two liter reaction flask equipped with reflux condenser, addition funnel, thermometer, cooling bath and apparatus for provision of a nitrogen atmosphere is placed 1 mole of methyl lithium in 1000 ml anhydrous diethylether. Over a period of 45 minutes while maintaining the reaction mass at 20°-25° C., 0.8 moles (156 grams) of the propianyl diisoamylene material produced according to Example II is added to the methyl lithium solution. After the addition of the propianyl diisoamylene, the reaction mass is maintained at 20°-23° C. for a period of 4 hours. The reaction mass is then admixed with 300 ml water during cooling. The resulting organic phase is then separated from the aqueous phase and the organic phase is stripped of ether and distilled on a microdistillation column yielding the following fractions:

| Fraction Number | Vapor Temp. °C. | Liquid Temp. °C. | Head Vac. mm. Hg | Reflux Ratio R/D | Weight of Fraction |
|---|---|---|---|---|---|
| 1 | 70/70 | 84/84 | 3/3 | 100% | 22 |
| 2 | 68 | 79 | 3 | 100% | 18 |
| 3 | 69 | 82 | 3 | 100% | 48 |
| 4 | 68 | 82 | 3 | 100% | 48 |
| 5 | 72 | 84 | 3 | 100% | 21 |
| 6 | 78 | 105 | 3 | 100% | 11 |
| 7 |  | 163 | 3 | 100% |  |

Fractions 2-6 are bulked and utilized for their organoleptic properties as set forth in the utility examples, infra.

FIG. 18 is the GLC profile of the crude reaction product of Example X containing the compounds defined according to the structure:

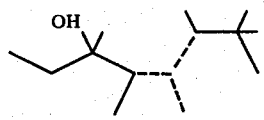

wherein in each of the molecles, one of the dashed lines represents a carbon-carbon single bond and each of the other of the dashed lines represent carbon-carbon double bonds.

FIG. 19 is the GLC profile for fraction 4 of the distillation product of the reaction product of Example X containing the compounds having the structure:

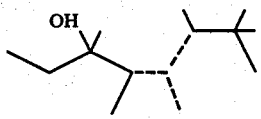

wherein in each of the molecules one of the dashed lines represents a carbon-carbon double bond and each of the other of the dashed lines represent carbon-carbon single bonds.

FIG. 20 is the infra-red spectrum for fraction 4 of the distillation product of the reaction product of Example X containing a mixture of compounds defined according to the structure:

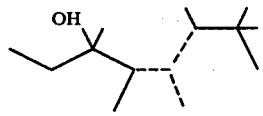

wherein in each of the molecules one of the dashed lines represents a carbon-carbon double bond and each of the other of the dashed lines represent carbon-carbon single bonds.

EXAMPLE XI

Hydrolysis Product of the Reaction Product of Methyl Lithium and Isobutyryl Diisoamylene Reaction:

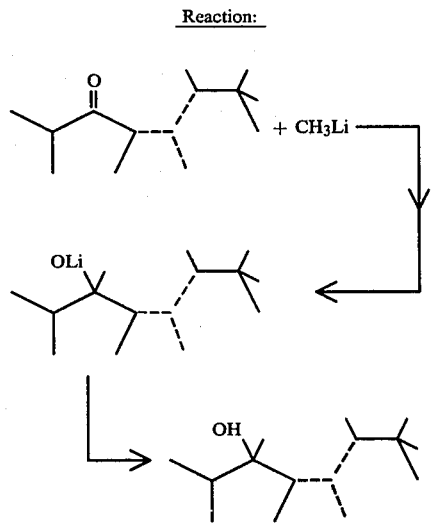

(wherein the reactant and product are mixtures and the mixtures contain molecules wherein one of the dashed lines represents a carbon-carbon double bond and each of the other of the dashed lines represent carbon-carbon single bonds).

Into a 2 liter reaction flask equipped with reflux condenser, addition funnel, thermometer, cooling bath and apparatus for provision of a nitrogen atmosphere is placed 1 mole of methyl lithium dissolved in 1000 ml diethylether. Over a period of 45 minutes while maintaining the reaction temperature at 19°–25° C., 167 grams (0.8 moles) of isobutyryl diisoamylene prepared according to Example III is added. At the end of the addition of the isobutyryl diisoamylene, the reaction mass is admixed with 300 ml water and the temperature of the reaction mass is cooled to 10° C. The reaction mass is then added to a 2 liter separatory funnel and the aqueous layer is separated from the organic layer. The organic layer is then stripped of solvent on a rotary evaporater and the crude product is then distilled on a microdistillation column yielding the following fractions:

| Fraction Number | Vapor Temp. °C. | Liquid Temp. °C. | Head Vac. mm. Hg | Reflux Ratio R/D | Weight of Fraction |
|---|---|---|---|---|---|
| 1 | 75/72 | 81/81 | 3/3 | 100% | 25 |
| 2 | 72 | 81 | 3 |  | 15 |
| 3 | 74 | 83 | 3 | 100% | 44 |
| 4 | 74 | 83 | 3 | 100% | 47 |
| 5 | 84 | 88 | 3 | 100% | 14 |
| 6 | 86 | 95 | 3 | 100% | 20 |
| 7 | 95 | 112 | 3 | 100% | 10 |
| 8 | 160 | 210 | 3 | 100% | 6 |

Fractions 2–6 are bulked and utilized for their organoleptic properties in the utility examples, infra.

FIG. 21 is the GLC profile of the crude reaction product of Example XI containing a mixture of compounds defined according to the structure:

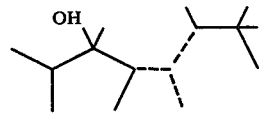

wherein in each of the molecules one of the dashed lines represents a carbon-carbon double bond and each of the other of the dashed lines represent carbon-carbon single bonds.

FIG. 22 is the GLC profile for fraction 7 of the distillation product of the reaction product of Example XI containing a mixture of compounds defined according to the structure:

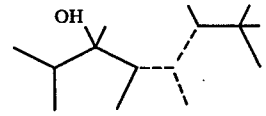

wherein in each of the molecules one of the dashed lines represents a carbon-carbon double bond and each of the other of the dashed lines represent carbon-carbon single bonds.

FIG. 23 is the infra-red spectrum for fraction 7 of the distillation product of the reaction product of Example XI containing a mixture of compounds defined according to the structure:

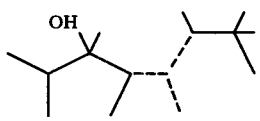

wherein in each of the molecules one of the dashed lines is a carbon-carbon double bond and each of the other of the dashed lines represent carbon-carbon single bonds.

FIG. 24 is the NMR spectrum for fraction 7 of the distillation product of the reaction product of Example XI containing a mixture of compounds defined according to the structure:

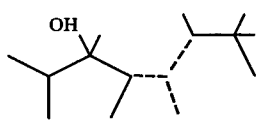

wherein in each of the molecules one of the dashed lines represents a carbon-carbon double bond and each of the other of the dashed lines represent carbon-carbon single bonds.

EXAMPLE XII

Hydrolysis Product of the Reaction Product Of n-Butyl Lithium And Acetyl Diisoamylene Reaction:

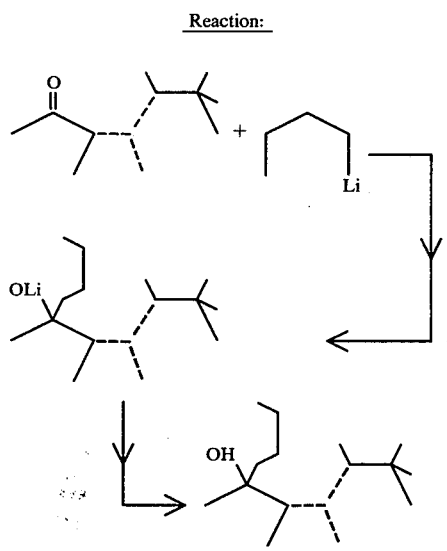

(wherein the reactant and product are mixtures and the mixtures contain molecules wherein one of the dashed lines represents a carbon-carbon double bond and each of the other of the dashed lines represent carbon-carbon single bonds).

Into a 2 liter reaction flask equipped with reflux condenser, addition funnel, thermometer, cooling bath and apparatus for provision of the nitrogen atmosphere is placed 1 mole of n-butyl lithium dissolved in 1000 cc anhydrous diethylether. To the n-butyl lithium solution is added 147 grams (0.8 moles) of acetyl diisoamylene prepared according to Example I over a period of 20 minutes while maintaining the reaction mass at 27°–28° C. The reaction mass is then refluxed at 68°–69° C. for about 5 minutes and then cooled to 27° C. Saturated aqueous ammonium chloride in water is then added to the reaction mass in order to hydrolize the resulting lithium salt. The reaction mass now exists in two phases and is added to a 2 liter separatory funnel. The layers are separated and the organic layer is stripped of solvent and distilled on a microdistillation column yielding the following fractions:

| Fraction Number | Vapor Temp. °C. | Liquid Temp. °C. | Head Vac. mm. Hg | Reflux Ratio R/D | Weight of Fraction |
|---|---|---|---|---|---|
| 1 | 76/83 | 88/90 | 1/3 | 100% | 9 |
| 2 | 87 | 94 | 2 | 100% | 3 |
| 3 | 94 | 102 | 2 | 100% | 5 |
| 4 | 105 | 112 | 2 | 100% | 5 |
| 5 | 108 | 110 | 2 | 100% | 8 |
| 6 | 110 | 120 | 2 | 100% | 2 |
| 7 | 112 | 125 | 2 | 100% | 1 |
| 8 | 116 | 135 | 2 | 100% | 1 |
| 9 | 160 | 220 | 3 | 100% | — |

Fractions 4–8 are bulked and used in the organoleptic utility examples, infra.

FIG. 25 is the GLC profile for the crude reaction product produced according to the procedure of Example XII containing a mixture of compounds defined according to the structure:

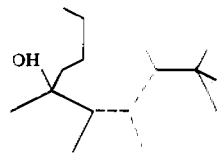

wherein in each of the molecules one of the dashed lines represents a carbon-carbon double bond and each of the other of the dashed lines represent carbon-carbon single bonds.

FIG. 26 is the GLC profile for fraction 8 of the distillation product of the reaction product of Example XII containing a mixture of compounds defined according to the structure:

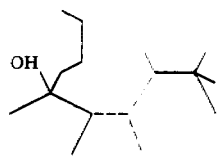

wherein in each of the molecules one of the dashed lines represents a carbon-carbon double bond and each of the other of the dashed lines represent carbon-carbon single bonds.

FIG. 27 is the infra-red spectrum for fraction 8 of the distillation product of the reaction product of Example XII containing a mixture of compounds defined according to the structure:

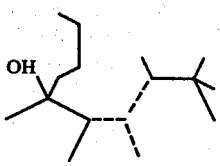

wherein one of the dashed lines is a carbon-carbon double bond and each of the other of the dashed lines represent carbon-carbon single bonds.

FIG. 28 is the NMR spectrum for fraction 8 of the distillation product of the reaction product of Example XII containing the compounds defined according to the structure:

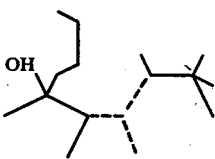

wherein in each of the molecules one of the dashed lines represents a carbon-carbon double bond and each of the other of the dashed lines represent carbon-carbon single bonds.

EXAMPLE XIII

Perfume Formulation

The branched chain unsaturated tertiary alcohols produced according to Examples IX-XII inclusive have intense amber, woody, fruity, floral, orris-like and camphoraceous and patchouli-like notes which may be utilized to a great extent in inexpensive functional products. The following pine fragrance demonstrates the use of these materials in perfume compositions. In this case, it is used in concentrations of 47.9%.

|  | XIIIA | XIIIB | XIIIC | XIIID |
|---|---|---|---|---|
| Isobornyl Acetate | 100 | 100 | 100 | 100 |
| Camphor | 10 | 10 | 10 | 10 |
| Terpineol | 25 | 25 | 25 | 25 |
| Fir Balsam Absolute (50% in Diethyl Phthalate) | 20 | 20 | 20 | 20 |
| Coumarin | 4 | 4 | 4 | 4 |
| Linalool | 30 | 30 | 30 | 30 |
| Anethol | 2 | 2 | 2 | 2 |
| Fenchyl Alcohol | 10 | 10 | 10 | 10 |
| Lemon Terpenes Washed | 50 | 50 | 50 | 50 |
| Borneol | 5 | 5 | 5 | 5 |
| Galbanum Oil | 5 | 5 | 5 | 5 |
| Turpentine Russian | 150 | 150 | 150 | 150 |
| Pinus Pumilionus | 50 | 50 | 50 | 50 |
| Eucalyptol | 50 | 50 | 50 | 50 |
| 2,2,6-trimethyl-1-cyclohexene-1-carboxaldehyde | 5 | 5 | 5 | 5 |
| Maltol 1% in Diethyl Phthalate | 5 | 5 | 5 | 5 |
| Product of Example IX | 479 | 0 | 0 | 0 |
| Product of Example X | 0 | 479 | 0 | 0 |
| Product of Example XI | 0 | 0 | 479 | 0 |
| Product of Example XII | 0 | 0 | 0 | 479 |

The presence of the various unsaturated branched chain tertiary alcohols support the pine notes and produce considerable savings in the cost of the formulation. However, each of the materials of each of the examples gives rise to separate nuances as follows:

TABLE II

| Structure | Organoleptic Properties (in Perfumery and in Perfumed Articles) |
|---|---|
| Mixture prepared according to Example IX supra wherein in each of the molecules of the mixture one of the dashed lines represents a carbon-carbon double bond and each of the other of the dashed lines represent carbon-carbon single bonds (bulked distillation fractions 2–8). | An amber, woody, camphoraceous aroma with patchouli topnotes. |
| Prepared according to Example X, a mixture wherein in each of the molecules of the mixture one of the dashed lines represents a carbon-carbon double bond and each of the other of the dashed lines represent carbon-carbon single bonds (bulked distillation fractions 2–6). | An ambery, woody, fruity aroma. |
| A mixture produced according to Example XI wherein in each of the molecules of the mixture one of the dashed lines is a carbon-carbon double bond and each of the other of the dashed lines represent carbon-carbon single bonds (bulked distillation fractions 2–6). | An orris-like aroma. |
| A mixture produced according to Example XII wherein in each of the molecules of the mixture one of the dashed lines is a carbon-carbon double bond and each of the other of the dashed lines represent carbon-carbon single bonds (bulked distillation fraction 4–8). | A floral, woody aroma. |

EXAMPLE XIV

Preparation of a Cosmetic Powder Composition

Cosmetic powders are prepared by mixing in a ball mill 100 grams of talcum powder with 0.25 grams of each of the substances set forth in Table III below. Each of the substances have aromas as set forth in Table III below:

TABLE III

| Structure | Organoleptic Properties (in Perfumery and in Perfumed Articles) |
|---|---|
| Mixture prepared according to Example IX supra wherein in each of the molecules of the mixture one of the dashed lines represents a carbon-carbon double bond and each of the other of the dashed lines represent carbon-carbon single bonds (bulked distillation fractions 2-8). | An amber, woody, camphoraceous aroma with patchouli topnotes. |
| Prepared according to Example X, a mixture wherein in each of the molecules of the mixture one of the dashed lines represents a carbon-carbon double bond and each of the other of the dashed lines represent carbon-carbon single bonds (bulked distillation fractions 2-6). | An ambery, woody, fruity aroma. |
| A mixture produced according to Example XI wherein in each of the molecules of the mixture one of the dashed lines is a carbon-carbon double bond and each of the other of the dashed lines represent carbon-carbon single bonds (bulked distillation fractions 2-6). | An orris-like aroma. |
| A mixture produced according to Example XII wherein in each of the molecules of the mixture one of the dashed lines is a carbon-carbon double bond and each of the other of the dashed lines represent carbon-carbon single bonds (bulked distillation fractions 4-8). | A floral, woody aroma. |

EXAMPLE XV

Perfumed Liquid Detergents

Concentrated liquid detergents (Lysine salt of n-dodecylbenzene sulfonic acid as more specifically described in U.S. Pat. No. 3,948,818, issued on Apr. 6, 1976) with aroma nuances as indicated in Table IV below are prepared containing 0.10%, 0.15%, 0.20%, 0.25%, 0.30% and 0.35% of the substances as set forth in Table IV below. They are prepared by adding homogeneously mixing the appropriate quantity of such substances in the liquid detergent. The detergents all possess aromas as set forth in Table IV below.

TABLE IV

| Structure | Organoleptic Properties (in Perfumery and in Perfumed Articles) |
|---|---|
| Mixture prepared according to Example IX supra wherein in each of the molecules of the mixture one of the dashed lines represents a carbon-carbon double bond and each of the other of the dashed lines represent carbon-carbon single bonds (bulked distillation fractions 2-8). | An amber, woody, camphoraeous aroma with patchouli topnotes. |
| Prepared according to Example X, a mixture wherein in each of the molecules of the mixture one of the dashed lines represents a carbon-carbon double bond and each of the other of the dashed lines represent carbon-carbon single bonds (bulked distillation fractions 2-6). | An ambery, woody, fruity aroma. |
| A mixture produced according to Example XI wherein in each of the molecules of the mixture one of the dashed lines is a carbon-carbon double bond and each of the other of the dashed lines represent carbon-carbon single bonds (bulked distillation fractions 2-6). | An orris-like aroma. |
| A mixture produced according to Example XII wherein in each of the molecules of the mixture one of the dashed lines is a carbon-carbon double bond and each of the other of the dashed lines represent carbon-carbon single bonds (bulked distillation | A floral, woody aroma. |

TABLE IV-continued

| Structure | Organoleptic Properties (in Perfumery and in Perfumed Articles) |
|---|---|
| fractions 4–8). | |

The intensities of each of the above aromas increases with greater concentrations of substance.

EXAMPLE XVI

Preparation of Colognes And Handkerchief Perfumes

Compositions as set forth in Table V below are incorporated into colognes at concentrations of 2.0%, 2.5%, 3.0%, 3.5%, 4.0%, 4.5% and 5.0% in 75%, 80%, 85% and 90% aqueous food grade ethanol solutions; and into handkerchief perfumes at concentrations of 15%, 20%, 25% and 30% (in 90%, 95% and 96% aqueous food grade ethanol solutions). Distinctive long-lasting pleasant aromas are imparted as set forth in Table V below to the colognes and to the handkerchief perfumes at all levels indicated above:

TABLE V

| Structure | Organoleptic Properties (in Perfumery and in Perfumed Articles) |
|---|---|
| [structure with OH]<br>Mixture prepared according to Example IX supra wherein in each of the molecules of the mixture one of the dashed lines represents a carbon-carbon double bond and each of the other of the dashed lines represent carbon-carbon single bonds (bulked distillation fractions 2–8). | An amber, woody, camphoraceous aroma with patchouli topnotes. |
| [structure with OH]<br>Prepared according to Example X, a mixture wherein in each of the molecules of the mixture one of the dashed lines represents a carbon-carbon double bond and each of the other of the dashed lines represent carbon-carbon single bonds (bulked distillation fractions 2–6). | An ambery, woody, fruity aroma. |
| [structure with OH]<br>A mixture produced according to Example XI wherein in each of the molecules of the mixture one of the dashed lines is a carbon-carbon double bond and each of the other of the dashed lines represent carbon-carbon single bonds (bulked distillation fractions 2–6). | An orris-like aroma. |
| [structure with OH]<br>A mixture produced according to Example XII wherein in each of the molecules of the mixture one of the dashed lines is a carbon-carbon double bond and each of the other of the dashed lines represent carbon-carbon single bonds (bulked distillation fractions 4–8). | A floral, woody aroma. |

EXAMPLE XVII

Preparation of Soap Composition 100 grams of soap chips (IVORY ® produced by the Procter and Gamble Company of Cincinnati, Ohio) are mixed with 1 gram of each of the substances of Table VI below until homogeneous compositions are obtained. In each of the cases the homogeneous compositions are heated under 3 atmospheres pressure at 180° C. for a period of 3 hours and the resulting liquids are then placed into soap molds. The resulting soap cakes, on cooling, manifest aromas as set forth in Table VI below:

TABLE VI

| Structure | Organoleptic Properties (in Perfumery and in Perfumed Articles) |
|---|---|
| [structure with OH]<br>Mixture prepared according to Example IX supra wherein in each of the molecules of the mixture one of the dashed lines represents a carbon-carbon double bond and each of the other of the dashed lines represent carbon-carbon single bonds (bulked distillation fractions 2–8). | An amber, woody, camphoraceous aroma with patchouli topnotes. |
| [structure with OH]<br>Prepared according to Example X, a mixture wherein in each of the molecules of the mixture one of the dashed lines represents a carbon-carbon double bond and each of the other of the dashed lines represent carbon-carbon single bonds (bulked distillation fractions 2–6). | An ambery, woody, fruity aroma. |

TABLE VI-continued

| Structure | Organoleptic Properties (in Perfumery and in Perfumed Articles) |
|---|---|
| [structure with OH] A mixture produced according to Example XI wherein in each of the molecules of the mixture one of the dashed lines is a carbon-carbon double bond and each of the other of the dashed lines represent carbon-carbon single bonds (bulked distillation fractions 2–6). | An orris-like aroma. |
| [structure with OH] A mixture produced according to Example XII wherein in each of the molecules of the mixture one of the dashed lines is a carbon-carbon double bond and each of the other of the dashed lines represent carbon-carbon single bonds (bulked distillation fractions 4–8). | A floral, woody aroma. |

EXAMPLE XVIII

Preparation of Solid Detergent Compositions

Detergents are prepared from the following ingredients according to Example I of Canadian Pat. No. 1,007,948:

| Ingredient | Percent by Weight |
|---|---|
| Neodol ® 45-11 (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate free detergent. A total of 100 grams of said detergent is admixed with 0.10, 0.15, 0.20, and 0.25 grams of each of the substances set forth in Table VII below. Each of the detergent samples has pleasant and long lasting aromas as set forth in Table VII below:

TABLE VII

| Structure | Organoleptic Properties (in Perfumery and in Perfumed Articles) |
|---|---|
| [structure with OH] Mixture prepared according to Example IX supra wherein in each of the molecules of the mixture one of the dashed lines represents a carbon-carbon double bond and each of the other of the dashed lines represent carbon-carbon single bonds (bulked distillation fractions 2–8). | An amber, woody, camphoraceous aroma with patchouli topnotes. |
| [structure with OH] Prepared according to Example X, a mixture wherein in each of the molecules of the mixture one of the dashed lines represents a carbon-carbon double bond and each of the other of the dashed lines represent carbon-carbon single bonds (bulked distillation fractions 2–6). | An ambery, woody, fruity aroma. |
| [structure with OH] A mixture produced according to Example XI wherein in each of the molecules of the mixture one of the dashed lines is a carbon-carbon double bond and each of the other of the dashed lines represent carbon-carbon single bonds (bulked distillation fractions 2–6). | An orris-like aroma. |
| [structure with OH] A mixture produced according to Example XII wherein in each of the molecules of the mixture one of the dashed lines is a carbon-carbon double bond and each of the other of the dashed lines represent carbon-carbon single bonds (bulked distillation fractions 4–8). | A floral, woody aroma. |

EXAMPLE XIX

Dryer-Added Fabric Softener Article

Utilizing the procedure of Example I at column 15 of U.S. Pat. No. 3,632,396, a nonwoven cloth substrate useful as a dryer-added fabric softening article of manufacture is prepared wherein the substrate, the substrate coating and the outer coating as well as the perfuming material are as follows:

1. a water "dissolvable" paper ("Dissolvo Paper").
2. Adogen 448 (m.p. about 140° F.) as the substrate coating; and
3. an outer coating having the following formulation (m.p. about 150° F.):

57% C$_{20-22}$ HAPS,
22% isopropyl alcohol,
20% antistatic agent,
1% of one of the substances set forth in Table VIII below.

Fabric softening compositions prepared according to Example I of U.S. Pat. No. 3,632,396 having aroma characteristics as set forth in Table VIII below essentially consist of a substrate having a weight of about 3 grams per 100 square inches; a substrate coating having a weight of about 1.85 grams per 100 square inches; and an outer coating having a weight of about 1.4 grams per 100 square inches of substrate, thereby providing a total aromatized substrate and outer coating weight ratio of about 1:1 by weight of the substrate. The aroma characteristics are as set forth in Table VIII below are imparted in a pleasant manner to the head space in the dryer on operation thereof, using said dryer-added fabric softening non-woven fabric.

TABLE VIII

| Structure | Organoleptic Properties (in Perfumery and in Perfumed Articles) |
|---|---|
| 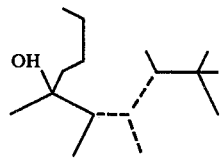 Mixture prepared according to Example IX supra wherein in each of the molecules of the mixture one of the dashed lines represents a carbon-carbon double bond and each of the other of the dashed lines represent carbon-carbon single bonds (bulked distillation fractions 2-8). | An amber, woody, camphoraceous aroma with patchouli topnotes. |
| 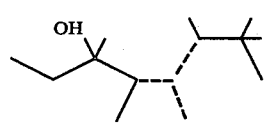 Prepared according to Example X, a mixture wherein in each of the molecules of the mixture one of the dashed lines represents a carbon-carbon double bond and each of the other of the dashed lines represent carbon-carbon single bonds (bulked distillation fractions 2-6). | An ambery, woody, fruity aroma. |
| 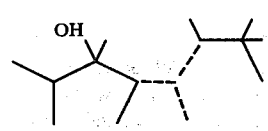 A mixture produced according to Example XI wherein in each of the molecules of the mixture one of the dashed lines is a carbon-carbon double bond and each of the other of the dashed lines represent carbon-carbon single bonds (bulked distillation fractions 2-6). | An orris-like aroma. |

TABLE VIII-continued

| Structure | Organoleptic Properties (in Perfumery and in Perfumed Articles) |
|---|---|
| 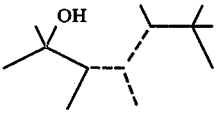 A mixture produced according to Example XII wherein in each of the molecules of the mixture one of the dashed lines is a carbon-carbon double bond and each of the other of the dashed lines represent carbon-carbon single bonds (bulked distillation fractions 4-8). | A floral, woody aroma. |

In the following examples, Aromox ® DMCW and Aromox ® DMMCW are 30% aqueous solutions of dimethyl cocoamine oxide and Aromox ® NCMDW is a 40% aqueous solution of N-cocomorpholine oxide produced by the Armac Division of AKZO of Chicago, Ill.

EXAMPLE XX

Four drops of one of the substances as set forth in Table IX below is added separately to 2 grams of Aromox ® DMCW to produce a clear premix. The clear premix is added to 200 grams of Clorox ® with stirring resulting in a clear stable single phase solution. Sufficient 1 M aqueous NaOH is added to bring the pH of each of the mixtures up to 12.8. The solutions remain substantially stable at 120° F. for a period of 7 days. When the 5% aqueous sodium hypochlorite solutions are used as laundry bleaches, the resulting laundry batches on dry-out in an atmosphere of 65% relative humidity yields substantially no characteristic "hypochlorite" odor but do have pleasant faint aromas as set forth in Table IX below. Furthermore, no such characteristic "hypochlorite" aromas are retained on the hands of the individual handling such laundry batches in both the wet and the dry states.

TABLE IX

| Structure | Organoleptic Properties (in Perfumery and in Perfumed Articles) |
|---|---|
|  Mixture prepared according to Example IX supra wherein in each of the molecules of the mixture one of the dashed lines represents a carbon-carbon double bond and each of the other of the dashed lines represent carbon-carbon single bonds (bulked distillation fractions 2-8). | An amber, woody, camphoraceous aroma with patchouli topnotes. |
|  Prepared according to Example X, a mixture wherein | An ambery, woody, fruity aroma. |

TABLE IX-continued

| Structure | Organoleptic Properties (in Perfumery and in Perfumed Articles) |
|---|---|
| in each of the molecules of the mixture one of the dashed lines represents a carbon-carbon double bond and each of the other of the dashed lines represent carbon-carbon single bonds (bulked distillation fractions 2-6). | |
| [Structure with OH] A mixture produced according to Example XI wherein in each of the molecules of the mixture one of the dashed lines is a carbon-carbon double bond and each of the other of the dashed lines represent carbon-carbon single bonds (bulked distillation fractions 2-6). | An orris-like aroma. |
| [Structure with OH] A mixture produced according to Example XII wherein in each of the molecules of the mixture one of the dashed lines is a carbon-carbon double bond and each of the other of the dashed lines represent carbon-carbon single bonds (bulked distillation fractions 4-8). | A floral, woody aroma. |

EXAMPLE XXI

Aromox ® DMMCW in various quantities is mixed with 1 gram each of one of the substances set forth in Table X below. The resulting premixes are then added to 200 grams of an aqueous 5% sodium hypochlorite solution. Sufficient 12.5 M aqueous NaOH is added to bring the pH of each of the mixtures up to 13. The following results are obtained:

| Percentage Aromox ® DMMCW | Clarity of hypochlorite solution after addition of premix |
|---|---|
| 0.23 | Clear after three days |
| 0.15 | Clear after three days |
| 0.08 | Initially slightly turbid; two phases exist after three days |

When each of the 5% aqueous sodium hypochlorite solutions are used as laundry bleaches, the resulting laundry batches on dry-out in an atmosphere of 65% relative humidity yields substantially no characteristic "hypochlorite" aroma but do have faint, pleasant aromas as set forth in Table X below. Furthermore, no such characteristic "hypochlorite" aroma is retained on the hands of the individuals handling such laundry batches in both the wet and the dry states.

TABLE X

| Structure | Organoleptic Properties (in Perfumery and in Perfumed Articles) |
|---|---|
| [Structure with OH] Mixture prepared according to Example IX supra wherein in each of the molecules of the mixture one of the dashed lines represents a carbon-carbon double bond and each of the other of the dashed lines represent carbon-carbon single bonds (bulked distillation fractions 2-8). | An amber, woody, camphoraceous aroma with patchouli topnotes. |
| [Structure with OH] Prepared according to Example X, a mixture wherein in each of the molecules of the mixture one of the dashed lines represents a carbon-carbon double bond and each of the other of the dashed lines represent carbon-carbon single bonds (bulked distillation fractions 2-6). | An ambery, woody, fruity aroma. |
| [Structure with OH] A mixture produced according to Example XI wherein in each of the molecules of the mixture one of the dashed lines is a carbon-carbon double bond and each of the other of the dashed lines represent carbon-carbon single bonds (bulked distillation fractions 2-6). | An orris-like aroma. |
| [Structure with OH] A mixture produced according to Example XII wherein in each of the molecules of the mixture one of the dashed lines is a carbon-carbon double bond and each of the other of the dashed lines represent carbon-carbon single bonds (bulked distillation fractions 4-8). | A floral, woody aroma. |

EXAMPLE XXII

Two grams of Aromox ® DMMC-W is admixed with eight drops each of one of the substances set forth in Table XI below. The premixes are then added with stirring to 200 grams of 7% aqueous solutions of lithium hypochlorite. Sufficient 3 M aqueous LiOH is added to bring the pH of the solution to 13.4. The mixtures are then heated to 120° F. and maintained at that temperature with stirring for a period of one week. The resulting solutions remain clear in a single phase. When used as laundry bleaches, the resulting bleached laundry on dry-out in an atmosphere of 50% relative humidity retains aromas as set forth in Table XI below; whereas without the use of the substances as set forth in Table XI below, the bleached laundry batches have faint characteristic disagreeable "hypochlorite" aromas.

TABLE XI

| Structure | Organoleptic Properties (in Perfumery and in Perfumed Articles) |
|---|---|
| (OH structure) Mixture prepared according to Example IX supra wherein in each of the molecules of the mixture one of the dashed lines represents a carbon-carbon double bond and each of the other of the dashed lines represent carbon-carbon single bonds (bulked distillation fractions 2-8). | An amber, woody, camphoraceous aroma with patchouli topnotes. |
| (OH structure) Prepared according to Example X, a mixture wherein in each of the molecules of the mixture one of the dashed lines represents a carbon-carbon double bond and each of the other of the dashed lines represent carbon-carbon single bonds (bulked distillation fractions 2-6). | An ambery, woody, fruity aroma. |
| (OH structure) A mixture produced according to Example XI wherein in each of the molecules of the mixture one of the dashed lines is a carbon-carbon double bond and each of the other of the dashed lines represent carbon-carbon single bonds (bulked distillation fractions 2-6). | An orris-like aroma. |
| (OH structure) A mixture produced according to Example XII wherein in each of the molecules of the mixture one of the dashed lines is a carbon-carbon double bond and each of the other of the dashed lines represent carbon-carbon single bonds (bulked distillation fractions 4-8). | A floral, woody aroma. |

EXAMPLE XXIII

Two grams of Aromox ® DMMC-W are admixed with separate quantities (8 drops) of each of the substances set forth in Table XII below. These premixes are then added separately, with stirring, to 200 grams of a mixture containing 4.5% aqueous sodium hypochlorite and 4.5% aqueous lithium hypochlorite. Sufficient 4 M aqueous LiOH is added to bring the pH of each of the solutions to 13.4. The mixtures are then heated to 120° F. and maintained at that temperature for a period of 1 week. The resulting solutions remain clear as a single phase. When used as laundry bleaches, the resulting bleached laundry batches on dry-out in an atmosphere of 50% relative humidity retain aromas as set forth in Table XII below; whereas without the use of the substances as set forth in Table XII below, the bleached laundry batches have faint characteristic disagreeable "hypochlorite" aromas.

TABLE XII

| Structure | Organoleptic Properties (in Perfumery and in Perfumed Articles) |
|---|---|
| (OH structure) Mixture prepared according to Example IX supra wherein in each of the molecules of the mixture one of the dashed lines represents a carbon-carbon double bond and each of the other of the dashed lines represent carbon-carbon single bonds (bulked distillation fractions 2-8). | An amber, woody, camphoraceous aroma with patchouli topnotes. |
| (OH structure) Prepared according to Example X, a mixture wherein in each of the molecules of the mixture one of the dashed lines represents a carbon-carbon double bond and each of the other of the dashed lines represent carbon-carbon single bonds (bulked distillation fractions 2-6). | An ambery, woody, fruity aroma. |
| (OH structure) A mixture produced according to Example XI wherein in each of the molecules of the mixture one of the dashed lines is a carbon-carbon double bond and each of the other of the dashed lines represent carbon-carbon single bonds (bulked distillation fractions 2-6). | An orris-like aroma. |
| (OH structure) A mixture produced according to Example XII wherein in each of the molecules of the mixture one of the dashed lines is a carbon-carbon double bond and each of the other of the dashed lines represent carbon-carbon single bonds (bulked distillation fractions 4-8). | A floral, woody aroma. |

EXAMPLE XXIV

Two grams of Aromox® DMMC-W is admixed with separate batches (8 drops each) of each of the substances set forth in Table XIII below. These premixes are then added, with stirring, separately to 200 gram batches of mixtures containing 4.5% aqueous sodium hypochlorite and 4.5% aqueous lithium hypochlorite. Sufficient 2 M aqueous NaOH is added to bring the pH of each of the solutions to 13.4. The mixtures are then heated to 110° F. and maintained at that temperature with stirring for a period of 2 weeks. The resulting solutions remain clear as a single phase when used as laundry bleaches. The resulting bleached laundry batches on dry-out in an atmosphere of 50% relative humidity retain aromas as set forth in Table XIII below, whereas without the use of such substances as set forth in Table XIII below, the bleached laundry batches have faint characteristic disagreeable "hypochlorite" aromas.

TABLE XIII

| Structure | Organoleptic Properties (in Perfumery and in Perfumed Articles) |
|---|---|
| [OH structure] Mixture prepared according to Example IX supra wherein in each of the molecules of the mixture one of the dashed lines represents a carbon-carbon double bond and each of the other of the dashed lines represent carbon-carbon single bonds (bulked distillation fractions 2–8). | An amber, woody, camphoraceous aroma with patchouli topnotes. |
| [OH structure] Prepared according to Example X, a mixture wherein in each of the molecules of the mixture one of the dashed lines represents a carbon-carbon double bond and each of the other of the dashed lines represent carbon-carbon single bonds (bulked distillation fractions 2–6). | An ambery, woody, fruity aroma. |
| [OH structure] A mixture produced according to Example XI wherein in each of the molecules of the mixture one of the dashed lines is a carbon-carbon double bond and each of the other of the dashed lines represent carbon-carbon single bonds (bulked distillation fractions 2–6). | An orris-like aroma. |
| [OH structure] A mixture produced according to Example XII wherein in each of the molecules of the mixture one of the dashed lines is a carbon-carbon double bond and each of the other of the dashed lines represent carbon-carbon single bonds (bulked distillation fractions 4–8). | A floral, woody aroma. |

EXAMPLE XXV

Four drops of each of the substances (separately) set forth in Table XIV are added to 1.5 gram batches of Aromox® NCMDW to produce clear premixes. The clear premixes are added to 200 grams of Clorox® with stirring resulting in clear, stable single phase solutions. Sufficient 1 M aqueous NaOH is added to each batch to bring the pH of each batch up to 12.8. The solutions remain substantially stable at 120° F. for a period of 7 days. When the 5% aqueous sodium hypochlorite solutions are used as laundry bleaches, the resulting laundry batches on dry-out in atmospheres of 65% relative humidity yield substantially no characteristic "hypochlorite" aroma but do have faint, pleasant aromas as set forth in Table XIV below. Furthermore, no such characteristic "hypochlorite" aroma is retained on the hands of the individual handling such laundry batches in both the wet and the dry states.

TABLE XIV

| Structure | Organoleptic Properties (in Perfumery and in Perfumed Articles) |
|---|---|
| [OH structure] Mixture prepared according to Example IX supra wherein in each of the molecules of the mixture one of the dashed lines represents a carbon-carbon double bond and each of the other of the dashed lines represents carbon-carbon single bonds (bulked distillation fractions 2–8). | An amber, woody, camphoraceous aroma with patchouli topnotes. |
| [OH structure] Prepared according to Example X, a mixture wherein in each of the molecules of the mixture one of the dashed lines represents a carbon-carbon double bond and each of the other of the dashed lines represent carbon-carbon single bonds (bulked distillation fractions 2–6). | An ambery, woody, fruity aroma. |
| [OH structure] A mixture produced according to Example XI wherein in each of the molecules of the mixture one of the dashed lines is a carbon-carbon double bond and each of the other of the dashed lines represent carbon-carbon single bonds (bulked | An orris-like aroma. |

TABLE XIV-continued

| Structure | Organoleptic Properties (in Perfumery and in Perfumed Articles) |
|---|---|
| distillation fractions 2–6). | |
| 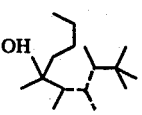 A mixture produced according to Example XII wherein in each of the molecules of the mixture one of the dashed lines is a carbon-carbon double bond and each of the other of the dashed lines represent carbon-carbon single bonds (bulked distillation fractions 4–8). | A floral, woody aroma. |

EXAMPLE XXVI

Four drop quantities of each of the substances set forth in Table XV below are added separately to one gram quantities of n-undecyl dimethyl amine oxide to produce clear premixes. The clear premixes are separately added to 200 gram quantities of Clorox ® with stirring resulting in clear, stable, single phase solutions. Sufficient 1 M aqueous NaOH is added to each of the batches to bring the pH of each of the batches up to 12.8. The solutions remain substantially stable at 120° F. for a period of 7 days. When the 5% aqueous sodium hypochlorite solutions are used as laundry bleaches, the resulting laundry batches on dry-out in an atmosphere of 65% relative humidity yield substantially no characteristic "hypochlorite" aroma but do have faint, pleasant aromas as set forth in Table XV. Furthermore, no such characteristic "hypochlorite" aromas are retained on the hands of the individual handling such laundry in both the wet and the dry states.

TABLE XV

| Structure | Organoleptic Properties (in Perfumery and in Perfumed Articles) |
|---|---|
| 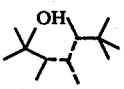 Mixture prepared according to Example IX supra wherein in each of the molecules of the mixture one of the dashed lines represents a carbon-carbon double bond and each of the other of the dashed lines represents carbon-carbon single bonds (bulked distillation fractions 2–8). | An amber, woody, camphoraceous aroma with patchouli topnotes. |
| Prepared according to Example X, a mixture wherein in each of the molecules of the mixture one of the dashed lines represents a carbon-carbon double bond and each of the other of the dashed lines represent carbon-carbon single bonds (bulked distillation fractions 2–6). | An ambery, woody, fruity aroma. |

TABLE XV-continued

| Structure | Organoleptic Properties (in Perfumery and in Perfumed Articles) |
|---|---|
| 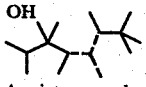 A mixture produced according to Example XI wherein in each of the molecules of the mixture one of the dashed lines is a carbon-carbon double bond and each of the other of the dashed lines represent carbon-carbon single bonds (bulked distillation fractions 2–6). | An orris-like aroma. |
| A mixture produced according to Example XII wherein in each of the molecules of the mixture one of the dashed lines is a carbon-carbon double bond and each of the other of the dashed lines represent carbon-carbon single bonds (bulked distillation fractions 4–8). | A floral, woody aroma. |

EXAMPLE XXVII

Four drop quantities of each of the substances set forth in Table XVI below are added separately to 1 gram quantities of n-dodecyl dimethyl amine oxide to produce clear premixes. The clear premixes are separately added to 200 grams quantities of Clorox ® with stirring resulting in clear, stable, single phase solutions. Sufficient 1 M aqueous NaOH is added to bring the pH of each of the mixtures up to 12.8. The solutions each remain substantially stable at 120° F. for a period of 7 days. When the 5% aqueous sodium hypochlorite solutions are used as laundry bleaches, the resulting laundry batches on dry-out in an atmosphere of 65% relative humidity yield substantially no characteristic "hypochlorite" odor but do have faint, pleasant aromas as set forth in Table XVI below. Furthermore, no such characteristic "hypochlorite" aroma is retained on the hands of the individual handling such laundry batches in both the wet and the dry states.

TABLE XVI

| Structure | Organoleptic Properties (in Perfumery and in Perfumed Articles) |
|---|---|
| 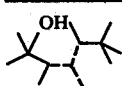 Mixture prepared according to Example IX supra wherein in each of the molecules of the mixture one of the dashed lines represents a carbon-carbon double bond and each of the other of the dashed lines represent carbon-carbon single bonds (bulked distillation fractions 2–8). | An amber, woody, camphoraceous aroma with patchouli topnotes. |
| 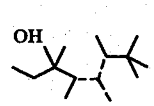 | An ambery, woody, fruity aroma. |

TABLE XVI-continued

| Structure | Organoleptic Properties (in Perfumery and in Perfumed Articles) |
|---|---|
| Prepared according to Example X, a mixture wherein in each of the molecules of the mixture one of the dashed lines represents a carbon-carbon double bond and each of the other of the dashed lines represent carbon-carbon single bonds (bulked distillation fractions 2-6). | |
| 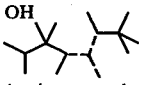 A mixture produced according to Example XI wherein in each of the molecules of the mixture one of the dashed lines is a carbon-carbon double bond and each of the other of the dashed lines represent carbon-carbon single bonds (bulked distillation fractions 2-6). | An orris-like aroma. |
| 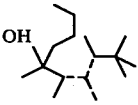 A mixture produced according to Example XII wherein in each of the molecules of the mixture one of the dashed lines is a carbon-carbon double bond and each of the other of the dashed lines represent carbon-carbon single bonds (bulked distillation fractions 4-8). | A floral, woody aroma. |

EXAMPLE XXVIII

One gram quantities of n-tridecyl dimethyl amine oxide is admixed with eight drop quantities of one of the substances set forth in Table XVII below. Each of the premixes is then added separately with stirring to 200 gram quantities of 7% aqueous solutions of lithium hypochlorite. Sufficient 3 M aqueous LiOH is added to bring the pH of each of the solutions to 13.4. The mixtures are then heated to 120° F. and maintained at that temperature with stirring for a period of one week. The resulting solutions remain clear and in a single phase. When used as a laundry bleach, the resulting bleached laundry batches on dry-out in an atmosphere of 50% relative humidity retain aromas as set forth in Table XVII below; whereas without the use of one of the substances of Table XVII below, the bleached laundry batches have faint, characteristic disagreeable "hypochlorite" aromas.

TABLE XVII

| Structure | Organoleptic Properties (in Perfumery and in Perfumed Articles) |
|---|---|
| 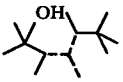 Mixture prepared according to Example IX supra wherein in each of the molecules of the mixture one of the dashed lines represents a carbon-carbon double bond and each of the other of the dashed lines represent carbon-carbon single bonds (bulked distillation fractions 2-8). | An amber, woody, camphoraceous aroma with patchouli topnotes. |
| 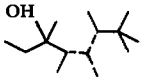 Prepared according to Example X, a mixture wherein in each of the molecules of the mixture one of the dashed lines represents a carbon-carbon double bond and each of the other of the dashed lines represent carbon-carbon single bonds (bulked distillation fractions 2-6). | An ambery, woody, fruity aroma. |
| 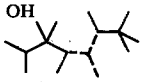 A mixture produced according to Example XI wherein in each of the molecules of the mixture one of the dashed lines is a carbon-carbon double bond and each of the other of the dashed lines represent carbon-carbon single bonds (bulked distillation fractions 2-6). | An orris-like aroma. |
| 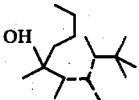 A mixture produced according to Example XII wherein in each of the molecules of the mixture one of the dashed lines is a carbon-carbon double bond and each of the other of the dashed lines represent carbon-carbon single bonds (bulked distillation fractions 4-8). | A floral, woody aroma. |

EXAMPLE XXIX

Flavor Composition

The following basic walnut flavor formulation is prepared:

| Ingredients | Parts by Weight |
|---|---|
| Ethyl-2-methyl butyrate | 10 |
| Vanillin | 40 |
| Butyl valerate | 40 |
| 2,3-Diethyl pyrazine | 5 |
| Methyl cyclopentenolone | 80 |
| Benzaldehyde | 60 |
| Valerian oil Indian (1% in 95% aqueous ethanol alcohol) | 0.5 |
| Propylene Glycol | 764.5 |

The branched chain unsaturated tertiary alcohol prepared according to Example IX is added to the above formulation at the rate of 1.5%. The formulation is compared to the formulation which does not have such branched chain unsaturated tertiary alcohol added thereto at the rate of 20 ppm in water. The formulation containing the branched chain unsaturated tertiary alcohol prepared according to Example IX has a "woody balsamic" fresh walnut kernel and walnut skin-like taste and, in addition, has a fuller mouth feel and longer lasting taste. The flavor that has added to it the branched chain unsaturated tertiary alcohol is preferred by a group of flavor panelists and they consider it to be a substantially improved walnut flavor.

EXAMPLE XXX

Beverage

The addition of the branched chain unsaturated tertiary alcohol prepared according to the process of Example X at the rate of 0.3 ppm is added to a commercial cola beverage and gives the beverage a fuller "woody balsamic" long lasting taste and adds to the pleasant top notes of the beverage. When comparing the cola beverage containing the branched chain unsaturated tertiary alcohol prepared according to Example X, to one having the same formula but not containing such tertiary alcohol, a five member bench panel prefers the beverage containing the branched chain unsaturated alcohol.

EXAMPLE XXXI

Tobacco Flavor Formulation

Cigarettes are produced using the following tobacco formulation:

| Ingredients | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| H$_2$O | 5.3 |

At the rate of 0.2%, the following tobacco flavor formulation is applied to all of the cigarettes produced with the above tobacco formulation.

| Ingredients | Parts by Weight |
| --- | --- |
| Ethyl butyrate | .05 |
| Ethyl valerate | .05 |
| Maltol | 2.00 |
| Cocoa Extract | 26.00 |
| Coffee Extract | 10.00 |
| Ethyl Alcohol (95%) | 20.00 |
| H$_2$O | 41.90 |

To 50% of the cigarettes, 10 and 20 ppm of the branched chain unsaturated tertiary alcohol prepared according to Example XI (bulked distillation fractions 2-6) are added. These cigarettes are hereinafter called "experimental" cigarettes and the cigarettes without the said tertiary alcohol are hereinafter called "control" cigarettes. The control and experimental cigarettes are then evaluated by paired comparison and the results are as follows:

a. In aroma, the experimental cigarettes are found to be more aromatic and more black tobacco-like.

b. In smoke flavor, the experimental cigarettes are found to be more aromatic, more sweet, more bitter, richer, "cigar box-like" and slightly less harsh in the mouth and more cigarette tobacco-like than the control cigarettes . . . and they all have "black tobacco" nuances.

The experimental cigarettes containing 20 ppm of the said tertiary alcohol produced according to Example XI (bulked distillation fractions 2-6) are found to be woody, slightly chemical and mouth-coating in the smoke flavor.

All cigarettes, both experimental and control are evaluated for smoke flavor with 20 mm cellulose acetate filters. The tertiary alcohol prepared to Example XI is very similar to to the tertiary alcohol prepared according to Example XII (bulked distillation fractions 4-8) and Example X (bulked distillation fractions 2-6) and each of these materials enhance the tobacco-like taste of the blended cigarette on smoking in both the main stream and the side stream.

What is claimed is:

1. A branched chain olefinic chalcogen derivative having the formula:

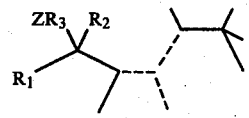

wherein Z represents oxygen or sulfur; wherein one of the dashed lines represents a carbon-carbon double bond and each of the other of the dashed lines represent carbon-carbon single bonds; wherein R$_1$ represents C$_1$-C$_4$ alkyl; R$_2$ represents C$_1$-C$_4$ alkyl; R$_3$ represents hydrogen, MgX, Li, C$_1$-C$_3$ lower alkyl or C$_1$-C$_3$ lower acyl and wherein X represents chloro, bromo or iodo.

2. The compound of claim 1 defined according to the structure:

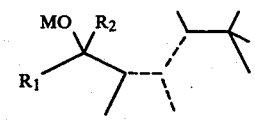

wherein M represents Li or MgX and X represents chloro, bromo or iodo.

3. The compound of claim 2 having the structure:

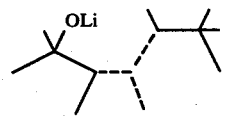

4. The compound of claim 1 having the structure:

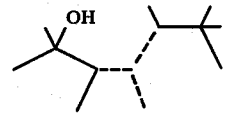

5. The compound of claim 1 having the structure:

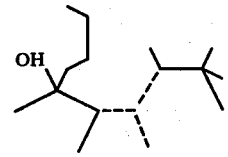

6. The compound of claim 1 having the structure:
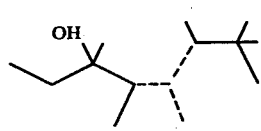
7. The compound of claim 1 having the structure:
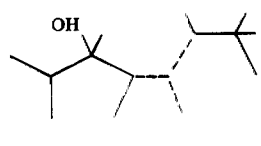
* * * * *